US011605460B2

(12) United States Patent
Calès

(10) Patent No.: US 11,605,460 B2
(45) Date of Patent: Mar. 14, 2023

(54) MULTI-TARGETED FIBROSIS TESTS

(71) Applicants: CENTRE HOSPITALIER UNIVERSITAIRE D'ANGERS, Angers (FR); UNIVERSITÉ D'ANGERS, Angers (FR)

(72) Inventor: Paul Calès, Avrillé (FR)

(73) Assignees: CENTRE HOSPITALIER UNIVERSITAIRE D'ANGERS, Angers (FR); UNIVERSITÉ D'ANGERS, Angers (FR)

( * ) Notice: Subject to any disclaimer, the term of this patent is extended or adjusted under 35 U.S.C. 154(b) by 845 days.

(21) Appl. No.: 16/322,633

(22) PCT Filed: Aug. 1, 2017

(86) PCT No.: PCT/EP2017/069478
§ 371 (c)(1),
(2) Date: Feb. 1, 2019

(87) PCT Pub. No.: WO2018/024748
PCT Pub. Date: Feb. 8, 2018

(65) Prior Publication Data
US 2021/0304890 A1    Sep. 30, 2021

(30) Foreign Application Priority Data
Jan. 8, 2016  (EP) .................................... 16182272

(51) Int. Cl.
*G01N 33/49* (2006.01)
*G16H 50/20* (2018.01)
(Continued)

(52) U.S. Cl.
CPC ............... *G16H 50/20* (2018.01); *G06N 7/00* (2013.01); *G16B 40/00* (2019.02); *G16H 30/20* (2018.01)

(58) Field of Classification Search
None
See application file for complete search history.

(56) References Cited

U.S. PATENT DOCUMENTS 10,622,109 B1 *  4/2020  McNair ................. G16B 20/00
2003/0175686 A1  9/2003  Rose et al.
(Continued)

FOREIGN PATENT DOCUMENTS

EP      2 600 266 A1    6/2013
WO     02/16949 A1    2/2002
(Continued)

OTHER PUBLICATIONS

International Search Report, PCT/EP2017/069478, dated Oct. 12, 2017.
(Continued)

*Primary Examiner* — Sultana M Zalalee
(74) *Attorney, Agent, or Firm* — Nixon & Vanderhye

(57) ABSTRACT

Disclosed is a non-invasive method for assessing in a subject the presence and severity of a liver lesion, or the risk of death or liver-related events, including: 1) performing at least three binary logistic regressions on at least one variable, performed on the same variable(s) but each directed to a different single diagnostic target, thereby obtaining at least three scores; 2) combining the scores from step 1) in a multiple linear regression to obtain a new multi-targeted score; 3) optionally sorting the multi-targeted score obtained in step 2) in a classification of liver lesion stages or grades, thereby determining to which liver lesion stage or grade the subject belongs based on his/her multi-targeted score. Also disclosed is a single multi-targeted non-invasive test obtained by the combination of single-targeted non-invasive
(Continued)

tests providing a unique score and a unique classification with improved accuracy compared to single-targeted diagnostic tests.

14 Claims, 4 Drawing Sheets

(51) Int. Cl.
*G16H 30/20* (2018.01)
*G16B 40/00* (2019.01)
*G06N 7/00* (2023.01)

(56) References Cited

U.S. PATENT DOCUMENTS

| | | | |
|---|---|---|---|
| 2004/0053242 A1 | 3/2004 | Volker et al. | |
| 2005/0112691 A1 | 5/2005 | Callewaert et al. | |
| 2005/0186561 A1 | 8/2005 | Oh et al. | |
| 2006/0253020 A1 | 11/2006 | Ehman et al. | |
| 2007/0037224 A1 | 2/2007 | Hamer et al. | |
| 2007/0072798 A1 | 3/2007 | Salonen et al. | |
| 2007/0111933 A1 | 5/2007 | Kopchick et al. | |
| 2007/0129633 A1 | 6/2007 | Lee et al. | |
| 2007/0178443 A1 | 8/2007 | Wienhues-Thelen et al. | |
| 2007/0247153 A1 | 10/2007 | Yu et al. | |
| 2009/0143993 A1 | 6/2009 | Cales | |
| 2010/0041069 A1 | 2/2010 | Lederkremer | |
| 2010/0049029 A1 | 2/2010 | Li et al. | |
| 2011/0306849 A1 | 12/2011 | Cales et al. | |
| 2012/0010824 A1 | 1/2012 | Cales et al. | |
| 2013/0225428 A1* | 8/2013 | Qin | C12Q 1/6876 506/18 |
| 2014/0005500 A1 | 1/2014 | Cales et al. | |
| 2015/0011424 A1* | 1/2015 | Oresic | G01N 33/492 250/282 |
| 2016/0012583 A1 | 1/2016 | Cales et al. | |
| 2017/0042864 A1* | 2/2017 | Forbes | A61K 45/06 |
| 2017/0082603 A1* | 3/2017 | Cales | G01N 33/49 |

FOREIGN PATENT DOCUMENTS

| | | |
|---|---|---|
| WO | 03/073822 A2 | 9/2003 |
| WO | 2004/063753 A2 | 7/2004 |
| WO | 2008/152070 A1 | 12/2008 |
| WO | 2009/092382 A1 | 7/2009 |
| WO | 2009/147125 A1 | 12/2009 |
| WO | 2010/058295 A2 | 5/2010 |
| WO | 2010/097472 A1 | 9/2010 |
| WO | 2013/045843 A1 | 4/2013 |
| WO | 2014/009569 A1 | 1/2014 |
| WO | 2015/155259 A1 | 10/2015 |

OTHER PUBLICATIONS

Meriden et al., Histologic predictors of fibrosis progression in liver allografts in patients with hepatitis C virus infection. Clinical gastroenterology and hepatology, 2010, 8(3):289-296.
Cales et al., Fibrosis progression under maintenance interferon in hepatitis C is better detected by blood test than liver morphometry. Journal of Viral Hepatitis, Feb. 2012;19(2):e143-53.
Zarski et al., Rate of natural disease progression in patients with chronic hepatitis C. J Hepatol. Mar. 2003;38 (3):307-14.
Baker et al., Metalloproteinase inhibitors: biological actions and therapeutic opportunities. J Cell Sci. Oct. 1, 2002; 115 (Pt 19):3719-27.
Friedrich-Rust et al., Real-time elastography for noninvasive assessment of liver fibrosis in chronic viral hepatitis. AJR Am J Roentgenol. Mar. 2007;188(3):758-64.
Nguyen-Khac et al., Assessment of asymptomatic liver fibrosis in alcoholic patients using fibroscan: prospective comparison with seven non-invasive laboratory tests. Aliment Pharmacol Ther. Nov. 1, 20085;28(10):1188-98.
Cook et al., Chapter 3: Binary response and Logistic Regression Analysis. Part of the Iowa State University NSF/ILI project Beyond Traditional Statistical Methods, 2001, pp. 1-23.
Preiss et al., Non-alcoholic fatty liver disease: an overview of prevalence, diagnosis, pathogenesis and treatment considerations Clin Sci (Lond). Sep. 2008;115(5):141-50.
Krawczyk et al., Nonalcoholic fatty liver disease. Best Pract Res Clin Gastroenterol. Oct. 2010;24(5):695-708.
Bettermann et al., Steatosis and steatohepatitis: complex disorders. Int J Mol Sci. Jun. 3, 2014;15(6):9924-44.
Livraghi, Guidelines for treatment of liver cancer. Eur J Ultrasound. Jun. 2001;13(2): 167-76.
Marinho et al., Hepatitis C, stigma and cure. World J Gastroenterol. Oct. 28, 2013;19(40):6703-9.
Block et al., Chronic hepatitis B: what should be the goal for new therapies? Antiviral Res. Apr. 2013;98(1):27-34.
Pascarella et al., Hepatitis D virus: an update. Liver Int. Jan. 2011;31(1):7 21.
Denzer et al., Non-invasive diagnosis and monitoring of liver fibrosis and cirrhosis. Best Pract Res Clin Gastroenterol. 2009;23(3):453-60.
Rockey, Current and future anti-fibrotic therapies for chronic liver disease. Clin Liver Dis. Nov. 2008;12(4):939-62, xi.
Popov & Schuppan, Targeting liver fibrosis: strategies for development and validation of antifibrotic therapies. Hepatology. Oct. 2009;50(4):1294-306.
Cohen-Naftaly & Friedman, Current status of novel antifibrotic therapies in patients with chronic liver disease. Therap Adv Gastroenterol. Nov. 2011;4(6):391-417.
Boursier et al., A new fibrosis staging method provides very accurate non-invasive diagnosis of liver fibrosis without liver biopsy, 2010, Journal of Hepatology, 52 : S405.
Cales et al., Accuracy of liver fibrosis classifications provided by non-invasive tests. 2010, Journal of Hepatology, 52 : S406.
Boursier et al., The combination of a blood test and Fibroscan improves the non-invasive diagnosis of liver fibrosis. Liver Int. Nov. 2009;29(10):1507 15.
Vergniol et al., Noninvasive tests for fibrosis and liver stiffness predict 5 year outcomes of patients with chronic hepatitis C, Gastroenterology 2011; 140(7):1970-1979.
Adams et al., "Hepascore: an accurate validated predictor of liver fibrosis in chronic hepatitis C infection". Clin Chem 2005;51:1867-1873.
Angulo et al., "The NAFLD fibrosis score: a noninvasive system that identifies liver fibrosis in patients with NAFLD". Hepatology 2007;45:846-854.
Bedossa al, "Intraobserver and interobserver variations in liver biopsy interpretation in patients with chronic hepatitis C". Hepatology 1994;20:15-20.
Bossuyt et al., "The STARD statement for reporting studies of diagnostic accuracy: explanation and elaboration". Clin Chem 2003;49:7-18.
Boursier et al., "Improved diagnostic accuracy of blood tests for severe fibrosis and cirrhosis in chronic hepatitis C". Eur J Gastroenterol Hepatol 2009;21:28-38.
Boursier et al., "A new combination of blood test and fibroscan for accurate non-invasive diagnosis of liver fibrosis stages in chronic hepatitis C". Am J Gastroenterol 2011;106:1255-1263.
Boursier et al., "Comparison of accuracy of fibrosis degree classifications by liver biopsy and non-invasive tests in chronic hepatitis C". BMC Gastroenterol 2011;11:132.
Boursier et al., "Comparison of eight diagnostic algorithms for liver fibrosis in hepatitis C: new algorithms are more precise and entirely noninvasive". Hepatology 2012;55:58-67.
Boursier et al., "Determination of reliability criteria for liver stiffness evaluation by transient elastography". Hepatology 2013;57:1182-1191.
Boursier et al., "Combination of blood tests for significant fibrosis and cirrhosis improves the assessment of liver-prognosis in chronic hepatitis C". Alimentary pharmacology & therapeutics 2014;40:178-88.

(56) References Cited

OTHER PUBLICATIONS

Boursier et al., "An extension of STARD statements for reporting diagnostic accuracy studies on liver fibrosis tests The Liver-FibroSTARD standards". J Hepatol. Apr. 2015;62(4):807-15.
Cales et al., "A novel panel of blood markers to assess the degree of liver fibrosis". Hepatology 2005;42:1373-1381.
Cales et al., "Evaluating the accuracy and increasing the reliable diagnosis rate of blood tests for liver fibrosis in chronic hepatitis C". Liver Int 2008;28:1352-1362.
Cales et al., "FibroMeters: a family of blood tests for liver fibrosis". Gastroenterol Clin Biol 2008;32:40-51.
Cales et al., "Comparison of blood tests for liver fibrosis specific or not to NAFLD". J Hepatol 2009;50:165-173.
Cales et al., "Optimization and robustness of blood tests for liver fibrosis and cirrhosis". Clin Biochem 2010;43:1315-1322.
Cales et al., "Comparison of liver fibrosis blood tests developed for HCV with new specific tests in HIV/HCV confection". J Hepatol 2010;52:238-44.
Cales et al., "Improved fibrosis staging by elastometry and blood test in chronic hepatitis C". Liver Int 2014;34:907-917.
Cales et al., "Cirrhosis Diagnosis and Liver Fibrosis Staging: Transient Elastometry Versus Cirrhosis Blood Test". J Clin Gastroenterol 2015;49:512-519.
Castera et al., "Prospective comparison of transient elastography, Fibrotest, APRI, and liver biopsy for the assessment of fibrosis in chronic hepatitis C". Gastroenterology 2005;128:343-350.
Castera et al., "Non-invasive evaluation of liver fibrosis using transient elastography". J Hepatol 2008;48:835-847.
Chou & Wasson, "Blood tests to diagnose fibrosis or cirrhosis in patients with chronic hepatitis C virus infection: a systematic review". Annals of internal medicine 2013;158:807-820.
Imbert-Bismut et al., "Biochemical markers of liver fibrosis in patients with hepatitis C virus infection: a prospective study" Lancet. Apr. 7, 2001;357(9262):1069-75.
Lambert et al., "How to measure the diagnostic accuracy of non-invasive liver fibrosis indices: the area under the ROC curve revisited" Clin Chem 2008;54:1372-1378.
Leroy et al., "Diagnostic accuracy, reproducibility and robustness of fibrosis blood tests in chronic hepatitis C: a meta-analysis with individual data". Clin Biochem 2008;41:1368-1376.
Leroy et al., "Prospective evaluation of FibroTest(R), FibroMeter(R), and HepaScore(R) for staging liver fibrosis in chronic hepatitis B: comparison with hepatitis C". J Hepatol 2014;61:28-34.
Naveau et al., "Diagnostic and prognostic values of noninvasive biomarkers of fibrosis in patients with alcoholic liver disease". Hepatology 2009;49:97-105.
Oberti et al., "Noninvasive diagnosis of hepatic fibrosis or cirrhosis". Gastroenterology 1997; 113:1609-1616.
Patel et al., "Evaluation of a panel of non-invasive serum markers to differentiate mild from moderate-to-advanced liver fibrosis in chronic hepatitis C patients". J Hepatol. Dec. 2004;41 (6):935-42.
Rosenberg et al., "Serum markers detect the presence of liver fibrosis: a cohort study". Gastroenterology. Dec. 2004;127(6):1704-13.
Sandrini et al., "Quantification of portal-bridging fibrosis area more accurately reflects fibrosis stage and liver stiffness than whole fibrosis or perisinusoidal fibrosis areas in chronic hepatitis C". Mod Pathol 2014;27:1035-45.

Sterling et al., "Development of a simple noninvasive index to predict significant fibrosis in patients with HIV/HCV coinfection" Hepatology 2006;43:1317-1325.
Thein et al., "Estimation of stage-specific fibrosis progression rates in chronic hepatitis C virus infection: a meta-analysis and meta-regression" Hepatology 2008;48:418-431.
Wai et al., "A simple noninvasive index can predict both significant fibrosis and cirrhosis in patients with chronic epatitis C" Hepatology 2003;38:518-526.
Zarski et al., "Comparison of nine blood tests and transient elastography for liver fibrosis in chronic hepatitis C: The ANRS HCEP-23 study". J Hepatol 2012;56:55-62.
Zeng et al., "Prediction of significant fibrosis in HBeAg-positive patients with chronic hepatitis B by a noninvasive model". Hepatology 2005;42:1437-1445.
El-Kamary et al., "Liver Fibrosis Staging through a Stepwise Analysis of Non-invasive Markers (FibroSteps) in Patients with Chronic Hepatitis C Infection". Liver Int. Aug. 2013; 33(7): 982-990.
Myers et al., "Biochemical Markers of Fibrosis in Patients with Chronic Hepatitis C: A Comparison with Prothrombin Time, Platelet Count, and Age-Platelet Index". Digestive diseases and Sciences, 2003, 48(1):146-153.
Michalak et al., "Respective roles of porto-septal fibrosis and centrilobular fibrosis in alcoholic liver disease". Journal of Pathology, 2003, 201(1):55-62.
Croquet et al., "Prothrombin index is an indirect marker of severe liver fibrosis". European Journal of Gastroenterology & Hepatology, 2002, 14(10):1133-1141.
Maor et al., "Improving estimation of liver fibrosis using combination and newer noninvasive biomarker scoring systems in hepatitis C-infected haemophilia patients". Haemophilia, 2007, 13(6):722-9.
Halfon et al., "Non-invasive fibrosis serum markers in chronic hepatitis C virus infection". La revue de médecine interne, 2006,27(10):751-61.
Leroy et al., "Prospective comparison of six non-invasive scores for the diagnosis of liver fibrosis in chronic hepatitis D" Journal of Hepatology, 2007, 46(5):775-82.
Sebastiani et al., "Sequential algorithms combining non-invasive markers and biopsy for the assessment of liver fibrosis in chronic hepatitis B". World journal of gastroenterology, 2007,13(4):525-531.
Bourliere et al., "Optimized stepwise combination algorithms of non-invasive liver fibrosis scores including Hepascore in hepatitis C virus patients". Alimentary Pharmacology & Therapeutics, 2008, 28(4):458-467.
Halfon et al., "Comparison of test performance profile for blood tests of liver fibrosis in chronic hepatitis C". Journal of Hepatology, 2007,46(3):395-402.
Sakaida et al., "Quantitative analysis of liver fibrosis and stellate cell changes in patients with chronic hepatitis C after interferon therapy" The American journal of Gastroentrology, 1999, 94(2):489-496.
Marcellin et al., "Fibrosis and disease progression in hepatitis C." Hepatology. Nov. 2002;36(5 Suppl 1):S47-56.
Leroy et al., "Changes in histological lesions and serum fibrogenesis markers in chronic hepatitis C patients non-responders to interferon alpha". Journal of Hepatology, 2001,35(1): 120-126.
Ghany et al., "Progression of fibrosis in chronic hepatitis C". Gastroenterology, 2003,124(1):97-104.

\* cited by examiner

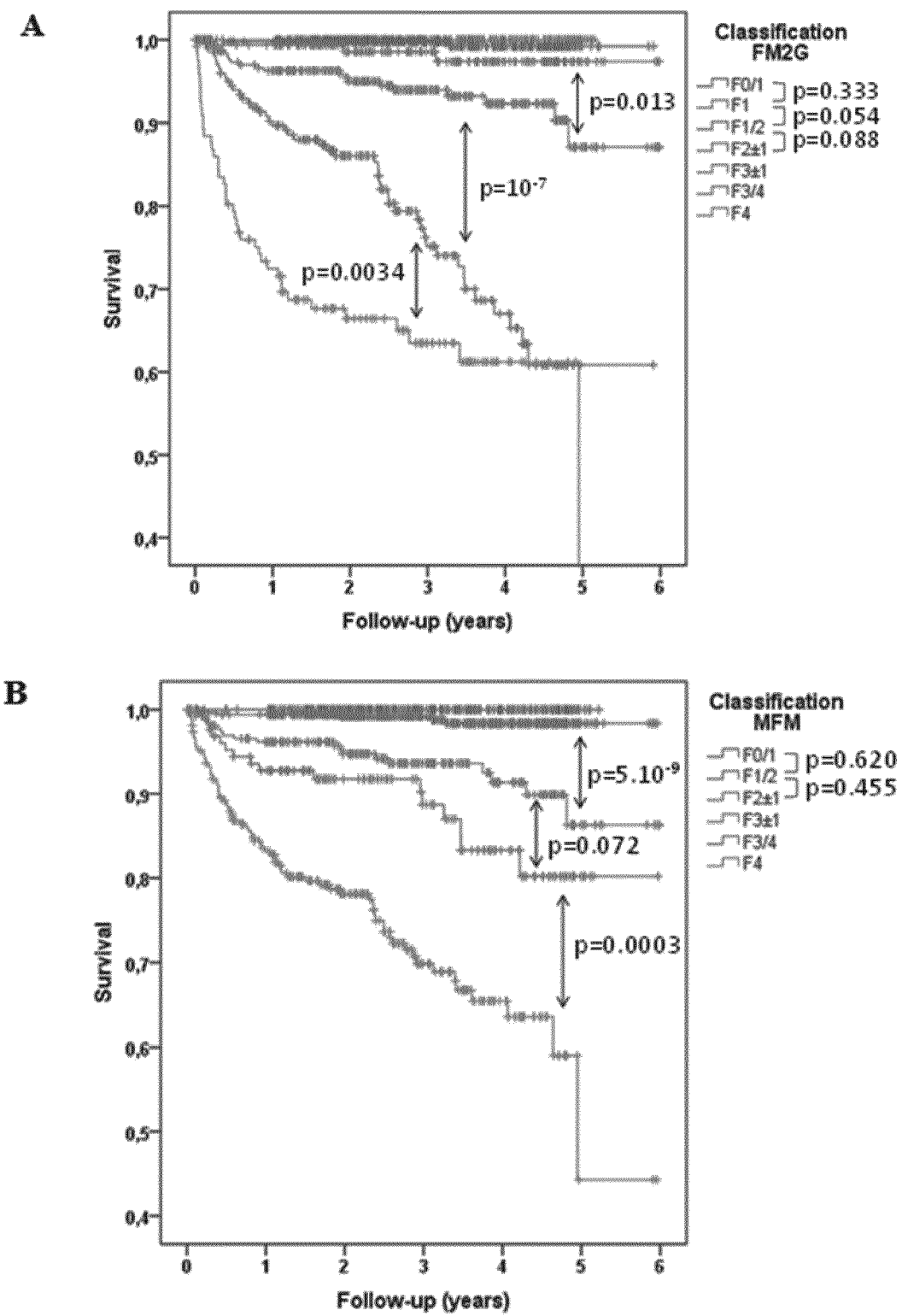
FIG. 3A-B

MULTI-TARGETED FIBROSIS TESTS

FIELD OF INVENTION

The present invention relates to the field of diagnosis in hepatology and more precisely to non-invasive methods for diagnosing a liver lesion, preferably liver fibrosis or cirrhosis, with a multi-targeted test. The present invention also relates to non-invasive prognostic methods for assessing, in a subject suffering from a liver condition, the risk of death or liver-related events with a multi-targeted test.

BACKGROUND OF INVENTION

Chronic liver diseases are characterized by the development of liver lesions such as liver fibrosis. Liver fibrosis is a scarring process that will progressively replace the damaged liver cells and thus modify the liver architecture. The extent of the fibrosis can vary, and it is usually described in stages. When diagnosed early, fibrosis is usually reversible.

Historically, liver fibrosis has been diagnosed through the microscopic examination by an expert liver pathologist of a liver sample obtained by a biopsy. The expert liver pathologist determines the stage of fibrosis according to an established fibrosis classification. The Metavir classification is the most used classification of fibrosis. It discriminates liver fibrosis into five stages from F0 to F4, with the F0 stage corresponding to the absence of fibrosis and the F4 stage to the ultimate stage of cirrhosis.

In clinical practice, patients with Metavir stage F≥2 are considered to suffer from clinically significant fibrosis. This cut-off is particularly relevant, notably for patient with hepatitis C, since treatment is usually recommended when clinically significant fibrosis is diagnosed. By contrast patients with Metavir stage F0 or F1 do not usually receive any treatment but are monitored for fibrosis progression. Patients with Metavir stage F2 considered to suffer from significant fibrosis, patients with Metavir stage F3 from severe fibrosis, and patients with Metavir stage F4 from cirrhosis.

In recent years, many non-invasive diagnostic tests have been developed to offer an alternative to liver biopsies. While liver biopsy is still considered the gold standard to assess the presence and/or the severity of a liver condition in a subject, it does have limitations, notably due to a poor inter- or intra-observer reproducibility and a possible sample bias linked to the small size of the sample. Furthermore, liver biopsy is an invasive medical procedure and as such remains associated with a risk of complication and a significant cost.

By contrast, non-invasive diagnostic tests require at most a blood sample from the subject to be implemented. Such tests are thus often referred to as "blood tests" or "fibrosis tests" as they aim to determine the presence and/or severity of liver fibrosis in the subject. The non-invasive blood tests of first generation involve the measurement of common indirect biomarkers, and optionally of clinical markers, and the calculation of ratios of these markers. Examples of such simple blood tests include the APRI (Wai et al. Hepatology 2003) and FIB-4 (Sterling et al. Hepatology 2006). The non-invasive blood tests of second generation comprise the statistic combination of independent direct and/or indirect biomarkers and clinical markers. Fibrotest (Imbert-Bismut et al. Lancet 2001), ELF score (Rosenberg et al. Gastroenterology 2004), FibroMeter (Cales et al. Hepatology 2005), Fibrospect (Patel et al. J Hepatology 2004) and Hepascore (Adams et al. Clin Chem 2005) are examples of these more elaborated blood tests. Another type of non-invasive tests consists in collecting and interpreting physical data useful for the diagnostic of liver fibrosis, such as for example conducting a liver stiffness evaluation by Vibration Controlled Transient Elastography (VCTE), also known as Fibroscan. Finally, a score resulting from a blood test can be combined in a logistic regression with physical data to obtain a new score. US20110306849 describes such a combination and in particular the combination of FibroMeter with Fibroscan.

Non-invasive diagnostic tests are usually binary single-targeted tests resulting in a test result, or test score, which is a continuous figure ranging from 0 to 1. They have been constructed to assess whether a targeted clinical feature, i.e., the diagnostic target, is absent (0) or present (1). Thus, most non-invasive fibrosis tests have been constructed with the diagnostic target of significant fibrosis (Metavir F≥2) and aim to discriminate between Metavir F0/1 vs. F2/3/4. Because the blood tests results are well correlated with the ordinal scale of Metavir stages, some fibrosis classifications have been developed to provide an estimation of the fibrosis stage from the blood test result. However, this approach is limited since the blood tests are calibrated for a precise diagnostic target (usually F≥2) and thus their performance for the diagnostic of clinical features distant from their diagnostic target, like cirrhosis (F=4), is less accurate. To palliate this deficiency, a non-invasive test, the CirrhoMeter, has been developed with the diagnostic target of cirrhosis, rather than significant fibrosis (Boursier et al. Eur J Gastroenterol Hepatol, 2009).

In clinical practice, physicians have to select which one of the existing non-invasive blood tests they need to implement. Indeed, for a given patient, a test with the diagnostic target F=4 might ensure more reliable results than a test with the diagnostic target F≥2, or vice-versa. If little information is available on a patient, it may prove difficult to know a priori which test to prescribe to said patient.

Thus, there remains a need for a single and unique test addressing multiple diagnostic targets, allowing the diagnosis of the different stages of fibrosis, including cirrhosis (F=4), with a good reliability and accuracy for all diagnostic targets. A single and unique test would indeed represent the easiest and most convenient solution, especially for physicians who may not have enough information to otherwise know which single-targeted test to implement. The present invention thus relates to multi-targeted diagnostic tests which can diagnose both clinically significant fibrosis and cirrhosis with high accuracy. Another object of the present invention is the use of multi-targeted diagnostic tests for assessing the risk of death or of liver-related event in a subject.

SUMMARY

This invention thus relates to a non-invasive method for assessing the presence and severity of a liver lesion in a subject, comprising:
1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression to obtain a new multi-targeted score useful for assessing the presence and severity of a liver lesion in the subject; and 3) optionally sorting the multi-targeted score obtained in step 2) in a classification of liver lesion stages or grades, thereby determining to which liver lesion stage or grade the subject belongs based on his/her multi-targeted score.

According to one embodiment, the non-invasive method of the invention for assessing the presence and severity of a liver lesion in a subject comprises:

1) performing at least 3 binary logistic regressions on at least one variable, wherein the binary logistic regressions are performed on the same variable(s) but are each directed to a different single diagnostic target, thereby obtaining at least 3 scores;

1a) performing at least another binary logistic regression including the at least 3 scores obtained at step 1), wherein the diagnostic target of said binary logistic regression is a clinically relevant binary target, thereby identifying the significant single-targeted scores among those obtained by the binary logistic regressions of step 1), said significant single-targeted scores being independently associated with said clinically relevant binary diagnostic target;

1b) deriving a classification of liver lesion stages or grades for each of the single-targeted binary logistic regressions found significant in step 1a);

1c) combining the classifications of step 1b) into a multi-targeted classification of liver lesion stages or grades; and 2) combining the significant scores identified in step 1a) in a multiple linear regression to obtain a single multi-targeted score, thereby assessing the presence and severity of a liver lesion in the subject.

In a particular embodiment, the non-invasive method of the invention is for assessing the presence and severity of liver fibrosis, including cirrhosis, in a subject.

In one embodiment, step 1) of the non-invasive method of the invention comprises performing 4 binary logistic regressions, each targeting a different Metavir fibrosis stage corresponding to F1, F2, F3 and F4 stages.

In another embodiment, step 1) of the non-invasive method of the invention comprises performing 7 binary logistic regressions, each with a different fibrosis target corresponding to Metavir fibrosis stages F≥1 (F≥1 vs. F0), F≥2 (F≥2 vs. F≤1), F≥3 (F≥3 vs. F≤2), F4 (F4 vs. F≤3), F1 vs. F0+F2+F3+F4, F2 vs. F0+F1+F3+F4, and F3 vs. F0+F1+F2+F4.

In another embodiment, step 1) of the non-invasive method of the invention comprises performing 10 binary logistic regressions, each with a different fibrosis target corresponding to Metavir fibrosis stages F≥1 vs. F=0, F≥2 vs. F≤1, F≥3 vs. F≤2, F=4 vs. F≤3, F1 vs. F0+F2+F3+F4, F2 vs. F0+F1+F3+F4, F3 vs. F0+F1+F2+F4, F1+F2 vs. F0+F3+F4, F2+F3 vs. F0+F1+F4 and F1+F2+F3 vs. F0+F4.

According to one embodiment, in the non-invasive method of the invention, the binary logistic regressions of step 1) are performed on at least one, preferably at least two, variables selected from biomarkers, clinical markers, qualitative markers, data obtained by a physical method of diagnosis, scores of fibrosis tests, descriptors of at least one image of the liver tissue of the subject previously obtained by an imaging method, and mathematical combinations thereof.

In one embodiment, in the non-invasive method of the invention, the binary logistic regressions of step 1) are performed on at least two descriptors of at least one image of the liver tissue of the subject previously obtained by an imaging method, said descriptors being selected from the group comprising linearity percentage of the edges, mean of percentage of fibrosis around areas (i.e., nodularity percentage), area of stellar fibrosis among the total surface of the liver biopsy specimen, number of bridges, bridges thickness, mean area of porto-septal regions, bridges perimeter, ratio of bridges among the porto-septal areas, area of fibrosis in the bridges, fractal dimension of peri-sinusoidal fibrosis, perimeter of the organ, tissue or fragment thereof, fractal dimension of porto-septal fibrosis, ratio of peri-sinusoidal fibrosis among the whole fibrosis, length of the organ, tissue or fragment thereof, anfractuosity descriptors (native perimeter, smoothed perimeter and ratio between both perimeters), fractal dimension of fibrosis, interquartile range of total density, Arantius furrow thickness, mean native liver perimeter, mean total spleen perimeter, ratio spleen surface to liver surface and mathematic combinations thereof.

In another embodiment, in the non-invasive method of the invention, the binary logistic regressions of step 1) are performed on at least one data obtained by a physical method of diagnosis, said physical method of diagnosis being an elastography method selected from Vibration Controlled Transient Elastography (VCTE) also known as Fibroscan, Acoustic Radiation Force Impulse (ARFI), supersonic shear imaging (SSI) elastometry, and MNR/MRI elastography.

In another embodiment, in the non-invasive method of the invention, the binary logistic regressions of step 1) are performed on at least one data obtained by a physical method of diagnosis, said physical method of diagnosis being a radiography method selected from X-ray, ultrasonography, computerized scanner, magnetic resonance imaging (MRI), functional magnetic resonance imaging, tomography, computed axial tomography, proton emission tomography (PET), single photon emission computed tomography and tomodensitometry.

In another embodiment, in the non-invasive method of the invention, the binary logistic regressions of step 1) are performed on at least one score of fibrosis test obtained with a fibrosis test selected from APRI, FIB4, Fibrotest, ELF score, FibroMeter, Fibrospect, Hepascore, Zeng score, and NAFLD fibrosis score, wherein said fibrosis test comprises the combination in a simple mathematical function or a binary logistic regression of markers selected from biological markers and/or clinical markers.

In another embodiment, in the non-invasive method of the invention, the binary logistic regressions of step 1) correspond to a fibrosis test selected from the FibroMeter family of fibrosis tests and combinations thereof with Vibration Controlled Transient Elastography (VCTE) also known as Fibroscan.

According to one embodiment, in the non-invasive method of the invention, the binary logistic regressions of step 1) are replaced by another statistical analysis selected from linear discriminant analysis and multivariate analysis.

In one embodiment, the non-invasive method of the invention is for assessing the presence and severity of a liver lesion in a subject suffering from a liver condition selected from the group comprising a liver impairment, a chronic liver disease, a hepatitis viral infection especially an infection caused by hepatitis B, C or D virus, a hepatoxicity, a liver cancer, a steatosis, a non-alcoholic fatty liver disease (NAFLD), a non-alcoholic steato-hepatitis (NASH), an autoimmune disease, a metabolic liver disease and a disease with secondary involvement of the liver.

The invention also relates to a microprocessor implementing the non-invasive method of the invention.

The invention also relates to a non-invasive method for assessing the risk of death, including non liver-related death and/or liver-related death, or liver-related events, especially complications, in a subject, comprising:

1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression to obtain a new multi-targeted score; and
3) optionally sorting the multi-targeted score obtained in step 2) in a classification of liver lesion stages or grades, thereby assessing the risk of death, including non liver-related death and/or liver-related death, or liver-related events in the subject.

Definitions

In the present invention, the following terms have the following meanings:

"About", preceding a figure means plus or minus 10% of the value of said figure.

"Accuracy" of a diagnostic test refers to the proportion of correctly diagnosed patients, i.e., the proportion of patients with correctly determined fibrosis stage (e.g., based on the Metavir staging of liver fibrosis) by said diagnostic test.

"AUROC" stands for area under the ROC curve, and is an indicator of the accuracy of a diagnostic test. In statistics, a receiver operating characteristic (ROC), or ROC curve, is a graphical plot that illustrates the performance of a binary classifier system as its discrimination threshold is varied. The curve is created by plotting the sensitivity against the specificity (usually 1-specificity) at successive values from 0 to 1. ROC curve and AUROC are well-known in the field of statistics.

"Biomarker" or "biological marker" refers to a variable that may be measured in a sample from the subject, said sample being a bodily fluid sample, such as, for example, a blood, serum or urine sample, preferably a blood or serum sample.

"Blood test", as used in the present invention, refers to a test comprising non-invasively measuring at least one variable, and, when at least two variables are measured, mathematically combining said at least two variables within a score. In the present invention, said variables may be a biomarker, a clinical marker, a qualitative marker, a data obtained by a physical method of diagnosis or any combination thereof (such as, for example, any mathematical combination within a score).

"Cirrhosis" refers to the ultimate stage of fibrosis according to the Metavir classification (F=4).

"Classification", in the present invention, refers to a system developed for a non-invasive diagnosis test aiming to sort out lesion stages or grades (e.g., liver fibrosis stages) into different classes. A subject is assigned to a class according to his/her score at the non-invasive test, thereby allowing a more precise diagnosis than a simple binary answer (yes/no) to the diagnostic target of the non-invasive test.

"Clinical data" refers to a data recovered from external observation of the subject, without the use of laboratory tests. Age, sex and body weight are examples of clinical data.

"Descriptor" refers to any computer-generated data associated with or derived from an image of an organ or tissue, such as, for example, an image obtained by microscopy or a radiological image. In an embodiment, the descriptor is a morphological descriptor. In an embodiment, the descriptor is an anatomic or physiological descriptor. Examples of computer-generated data include, but are not limited to, data regarding structural properties of the organ or tissue (such as, for example, its length), spectral properties of the organ or tissue image (such as, for example, contrast or luminosity), fractal properties of the organ or tissue, shape of the organ or tissue, and other image data transforms.

"Diagnostic cut-off" refers to the diagnostic cut-off of a test score. The cut-off is usually provided by binary logistic regression and distinguishes patients with or without the diagnostic target (yes/no). It can be fixed in two ways: a priori to 0.5 according to statistical convention, and a posteriori according to specific choice, usually the highest Youden index (Se+Spe−1) or the maximum overall accuracy to optimize test performance.

"Diagnostic target" refers to the main objective of a non-invasive diagnostic test. Most non-invasive fibrosis tests are binary tests constructed for a single diagnostic target (single-targeted tests), i.e., for determining the presence or absence (yes/no) of a targeted clinical feature. Thus, in one embodiment, the diagnostic target of fibrosis tests may be defined by two ranges of Metavir fibrosis stages with a diagnostic cut-off between them (e.g., F0/1 vs. F2/3/4 for the diagnosis of the presence or absence of significant fibrosis defined as F≥2).

"Fibrosis", refers to a pathological lesion of the liver made of scar tissue including fibrillary proteins or glycoproteins (collagens, proteoglycans . . . ).

"Fibrosis test" refers to a non-invasive diagnostic test with the aim to assess the presence and/or severity of liver fibrosis in a subject.

"Histology activity index or HAI system", also known as Knodell score, refers to a classification system of liver fibrosis based on a histological description of a liver tissue sample. The HAI system scores necro-inflammatory activity from 0 to 18 and fibrosis in 4 stages (0, 1, 3 or 4).

"Ishak scoring system" refers to a classification system of liver fibrosis based on a histological description of a liver tissue sample. The Ishak system scores necro-inflammatory activity changes on a scale from 0 to 18 and fibrosis on a scale from 0 to 6.

"Kleiner grading/staging" refers to a classification system devoted to NAFLD (non-alcoholic fatty liver disease) and based on a morphological description in different classes either for steatosis (conventionally referred as grading) or fibrosis (conventionally referred as staging). This semi-quantitative (ordinal in statistics) system is the most recent and conventional histological classification. This system is also known as the NASH Clinical Research Network (NASH-CRN) system.

"Liver lesion" refers to any abnormality in the liver. In one embodiment of the invention, a liver lesion may be caused by a disease, and may consequently be referred to as a "pathological lesion". Liver lesions include, but are not limited to, liver fibrosis, cirrhosis, liver steatosis, fragmentation, necrotico-inflammatory activity or non-alcoholic steato-hepatitis (NASH).

"Metavir" refers to a pathological semi-quantitative classification of liver fibrosis in 5 stages (F0-F4) based on a histological description of a liver tissue sample. The Metavir system also classifies necro-inflammatory activity in 4 grades (A0-A3).

"Multi-targeted test", in the present invention, refers to a non-invasive diagnostic test constructed to address simultaneously various, preferably at least two, preferably 3, 4, 5, 6, 7, 8, 9, 10 diagnostic targets, more preferably all diagnostic targets of a pathology.

"Multi-FibroMeter" refers to a multi-targeted FibroMeter (MFM) test. One construction is aimed primarily at providing a fibrosis test classification; this test is called MFMc. Another construction is aimed primarily at providing a test score; this test is called MFMs. When constructed in viral etiology ("virus"), MFM is called $MFM^V$. Likewise, as single-targeted FibroMeters include as biomarkers, among others, either hyaluronate (FibroMeter virus of second generation or $FM^{V2G}$) or GGT (FibroMeter virus of third generation or $FM^{V3G}$), corresponding MFM are called $MFM^{V2G}$ or $MFM^{V3G}$. Thus, at least four MFM are available:

|  |  | Construction aim | |
|---|---|---|---|
|  |  | Classification | Score |
| Marker | Hyaluronate | $MFMc^{V2G}$ | $MFMs^{V2G}$ |
| Composition | GGT | $MFMc^{V3G}$ | $MFMs^{V3G}$ |

However, it should be noticed that each MFM is available with the two expressions, i.e., score (range: 0 to 1) and fibrosis classification (e.g., F0 to F4).

"Non-invasive", when referring to a test in the present invention, means that no tissue is taken from the body of an individual to carry out said test (blood is not considered as a tissue).

"Percentile", corresponds to an interval in which a certain percent of observations falls. For example, when dividing a population in 10 percentiles of 10%, each percentile contains 10% of the population.

"Physical data" refers to a variable obtained by a physical method such as, for example, the liver stiffness evaluation conducted by Vibration Controlled Transient Elastography (VCTE).

"Qualitative marker" refers to a marker determined for a subject having the value 0 or the value 1 (or yes or no). Treatment data, etiology, SVR (wherein SVR stands for sustained virologic response) are examples of qualitative markers.

"Reliable diagnosis intervals (RDIs)" correspond to the intervals of diagnostic test values (such as, for example, for fibrosis and/or necrotico-inflammatory activity) wherein the diagnostic accuracy is considered sufficiently reliable for clinical practice.

"Sensitivity", for a non-invasive test, measures the patient proportion of true positives, for the diagnostic target of the non-invasive test, which are correctly identified as such.

"Specificity", for a non-invasive test, measures the patient proportion of true negatives, for the diagnostic target of the non-invasive test, which are correctly identified as such.

"Single-targeted test", or mono-targeted test, refers to a binary test constructed for a single diagnostic target. In one embodiment, single-targeted fibrosis tests address a diagnostic target usually defined by two ranges of Metavir fibrosis stages with a diagnostic cut-off between them (e.g., F0/1 vs. F2/3/4, i.e., F0+F1 vs. F2+F3+F4, for the diagnosis of significant fibrosis defined as F≥2).

"Score", as in test score (that may also be referred to as test value) or score value, refers to any digit value obtained by the mathematical combination of at least one biomarker and/or at least one clinical data and/or at least one physical data and/or at least one blood test result. In one embodiment, a score is a bound digit value, obtained by a mathematical function. Preferably, the score may range from 0 to 1.

"Steatosis" is defined as the accumulation of lipids, usually triglycerides, within vacuoles of cells. It mainly concerns liver and muscle in metabolic syndrome.

"Subject" refers to a mammal, preferably a human. In one embodiment, a subject may be a "patient", i.e., a warm-blooded animal, more preferably a human, who/which is awaiting the receipt of, or is receiving, medical care or was/is/will be the subject of a medical procedure, or is monitored for the development or progression of a disease. In one embodiment, the subject is an adult (for example a subject above the age of 18). In another embodiment, the subject is a child (for example a subject below the age of 18). In one embodiment, the subject is a male. In another embodiment, the subject is a female.

"Variable" refers to measures, obtained from a patient, that can be combined in a binary logistic regression in the method of the invention. Variables in the present invention include biological markers, clinical markers, qualitative markers, physical data, fibrosis test scores, indexes, and descriptors of images.

"Youden index" is defined as sensitivity+specificity−1, where sensitivity and specificity are calculated as proportions. The Youden index has minimum and maximum values of −1 and +1, respectively, with a value of +1 representing the optimal value for an algorithm.

DETAILED DESCRIPTION

The invention relates to a non-invasive method for assessing the presence and severity of a liver lesion in a subject comprising carrying out a multi-targeted test. Liver lesions include, but are not limited to, liver fibrosis, cirrhosis, liver steatosis, fragmentation, necrotico-inflammatory activity or non-alcoholic steato-hepatitis (NASH).

In one embodiment, the invention relates to a non-invasive method for assessing the presence and severity of liver fibrosis, including cirrhosis, in a subject comprising carrying out a multi-targeted test.

Another object of the invention is a non-invasive method for assessing the risk of death, non liver-related death or liver-related death, or liver-related events, especially complications, in a subject comprising carrying out a multi-targeted test. The present invention also relates to non-invasive methods for determining an increased risk of mortality or of liver-related event in a subject comprising carrying out a multi-targeted test.

In one embodiment, the non-invasive methods of the invention are in vitro methods.

Preferably, the multi-targeted test of the invention is constructed with a multiple linear regression.

The table below provides an overview of the constructions of the multi-targeted tests of the invention.

| Statistical methods | | Variables handled | | Tests | |
| --- | --- | --- | --- | --- | --- |
| Type | Technique | Input | Output | MFMs | MFMc |
| Binary logistic regression | several possible targets | Biomarkers | Single-targeted scores | Step 1 | Step 1 |
| | two usual targets | Single-targeted scores | Significant single-targeted scores | — | Step 1a |
| Multiple linear regression | targeted for normalized classification | Single-targeted scores (MFMs) | MULTI-TARGETED SCORE [a] | Step 2 | Step 2 |
| Segmentation by | percentiles | Significant single-targeted scores (MFMc) or multi-targeted score (MFMs) | Classification(s): single final in MFMs, several intermediate in MFMc | Optional Step 3 | Step 1b |
| | maximum accuracy by pairwise comparison | Intermediate classifications (MFMc) | MULTI-TARGETED CLASSIFICATION [b] | — | Step 1c |

[a] Primary objective for MFMs (variable in capitals)
[b] Primary objective for MFMc (variable in capitals)

The method of the invention describes a single multi-targeted diagnostic or prognostic test based on the combination of single-targeted binary logistic regressions, thereby providing a unique score and a unique classification with improved accuracy compared to single-targeted tests.

In one embodiment, the method of the invention describes a single multi-targeted diagnostic test based on the combination of single-targeted diagnostic tests, thereby providing a unique score and a unique classification with improved accuracy compared to single-targeted diagnostic tests.

Thus, in one embodiment, the invention relates to a non-invasive method for assessing the presence and severity of a liver lesion in a subject, comprising:
1) performing at least 3 binary logistic regressions on at least one variable, wherein the binary logistic regressions are performed on the same variable(s) but are each directed to a different single diagnostic target, thereby obtaining at least 3 scores; and
2) combining the at least 3 scores obtained in step 1) in a multiple linear regression to obtain a new multi-targeted score useful for assessing the presence and severity of a liver lesion in the subject.

In this embodiment, the method of the invention thus comprises carrying out a multi-targeted test addressed to at least 3 diagnostic targets.

In a preferred embodiment, the multiple linear regression is a stepwise multiple linear regression, i.e., a multiple linear regression with a stepwise selection of independent variables.

In one embodiment, the method of the invention optionally comprises sorting the multi-targeted score obtained in step 2) in a classification of liver lesion stages or grades, thereby determining to which liver lesion stage or grade the subject belongs based on their multi-targeted score.

Therefore, in one embodiment, the non-invasive method for assessing the presence and severity of a liver lesion in a subject comprises:
1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression, preferably a multiple linear regression with a stepwise selection of independent variables, to obtain a new multi-targeted score; and
3) positioning the multi-targeted score obtained in step 2) in a classification of liver lesion stages or grades, thereby determining to which lesion stage or grade the subject belongs based on his/her multi-targeted score.

In one particular embodiment, the invention relates to a non-invasive method for assessing the presence and severity of liver fibrosis, including cirrhosis, in a subject, comprising:
1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression to obtain a new multi-targeted score; and
3) optionally positioning the multi-targeted score obtained in step 2) in a classification of fibrosis stages, thereby determining to which fibrosis stages (or class of fibrosis stages) the subject belongs based on his/her multi-targeted score.

In one particular embodiment, the invention relates to a non-invasive method for assessing the presence and severity of liver fibrosis, including cirrhosis, in a subject, comprising:
1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression targeted to the Metavir score of said subject to obtain a new multi-targeted score; and
3) optionally positioning the multi-targeted score obtained in step 2) in a classification of fibrosis stages, thereby determining to which fibrosis stages (or class of fibrosis stages) the subject belongs based on his/her multi-targeted score.

In another embodiment, the invention relates to a non-invasive method for assessing the risk of death, including non liver-related death and/or liver-related death, or liver-related events, especially complications, in a subject, comprising:

1) performing at least 3 binary logistic regressions on at least one variable, wherein the binary logistic regressions are performed on the same variable(s) but are each directed to a different single diagnostic target, thereby obtaining at least 3 scores; and
2) combining the at least 3 scores obtained in step 1) in a multiple linear regression, preferably a multiple linear regression with a stepwise selection of independent variables, to obtain a new multi-targeted score useful for assessing the risk of death, including non liver-related death or liver-related death, or liver-related events in the subject.

In one embodiment, the method of the invention optionally comprises sorting the multi-targeted score obtained in step 2) in a classification of liver lesion stages or grades, thereby assessing the risk of death, including non liver-related death and/or liver-related death, or liver-related events in the subject.

Therefore, in one embodiment, the non-invasive method for assessing the risk of death, including non liver-related death and/or liver-related death, or liver-related events, especially complications, in a subject comprises:
1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression to obtain a new multi-targeted score; and
3) positioning the multi-targeted score obtained in step 2) in a classification of liver lesion stages or grades, thereby assessing the risk of death, including non liver-related death and/or liver-related death, or liver-related events in the subject.

In one embodiment, the multiple linear regression, preferably a multiple linear regression with a stepwise selection of independent variables, of step 2) of the method of the invention is targeted to Metavir F stage(s).

Thus, in one embodiment, the multi-targeted test of the invention comprises the optional step of sorting the multi-targeted score in a classification of liver lesion stages or grades, for example fibrosis stages, thereby determining to which liver lesion stage or grade (or class of lesion stages or grades), for example fibrosis stage (or class of fibrosis stages) the subject belongs based on his/her multi-targeted score.

In one embodiment, the classification used in the optional step 3) of the method of the invention is previously obtained.

According to one embodiment, the classification of the method of the invention is based on the Metavir classification of fibrosis stages. Thus, in one embodiment, said classification is obtained from a reference population by deriving the correspondence between the score obtained at step 2) and the fibrosis Metavir stages. In one embodiment, the classification comprises 4, 5, 6, 7, 8, 9, or 10 classes based on fibrosis Metavir stages, preferably 5, 6, 7 or 8 classes based on fibrosis Metavir stages.

In one embodiment, the classification comprises 5 classes based on fibrosis Metavir stages. In on embodiment, said 5 classes based on fibrosis Metavir stages are: 0/1 (F0/1), 1/2 (F1/2), 2/3 (F2/3), 3/4 (F3/4) and 4 (F4). In another embodiment, the classification comprises 6 classes based on fibrosis Metavir stages. In one embodiment, said 6 classes based on fibrosis Metavir stages are: F0/1, 1/2 (F1/2), 2 (F2±1), 3 (F3±1), 3/4 (F3/4) and 4 (F4).

According to another embodiment, the classification of the method of the invention is based on the histological activity index (HAI) classification including fibrosis stages. Thus, in one embodiment, said classification is obtained from a reference population by deriving the correspondence between the score obtained at step 2) and the fibrosis stages as defined according to the HAI system.

According to another embodiment, the classification of the method of the invention is based on the Ishak classification of fibrosis stages. Thus, in one embodiment, said classification is obtained from a reference population by deriving the correspondence between the score obtained at step 2) and the fibrosis stages as defined according to the Ishak system.

According to another embodiment, the classification of the method of the invention is based on the Metavir classification of necrotico-inflammatory activity grades. Thus, in one embodiment, said classification is obtained from a reference population by deriving the correspondence between the score obtained at step 2) and the Metavir necrotico-inflammatory activity grades.

According to another embodiment, the classification of the method of the invention is based on the Kleiner grading/staging devoted to NAFLD, also known as the NASH Clinical Research Network (NASH-CRN) system. Thus, in one embodiment, said classification is obtained from a reference population by deriving the correspondence between the score obtained at step 2) and the Kleiner grading/staging or NASH-CRN system.

According to one embodiment, the classification of the method of the invention is obtained by the method assigning lesion stages or grades into classes according to percentiles, as described in US 2014005500 which is hereby incorporated by reference. Briefly, the patients of a reference population are classified into percentiles according to their score result. Then, for each population percentile the associated gold standard lesion stage(s) or grade(s), as defined according to one reference system (e.g., Metavir, Ishak, Kleiner), are determined according to a high fixed minimum correct classification rate (e.g., 80%). The maximum number of gold standard stages or grades that can be associated to each percentile is limited (e.g., to 3). The association of a limited number of gold standard lesion stages or grades to each population percentile according to a fixed minimum correct classification rate thus allows the grouping of lesion stages or grades into new classes.

According to another embodiment, the classification of the method of the invention is obtained according to the reliable diagnostic intervals (RDIs) method as described in US 2014005500 which is hereby incorporated by reference.

According to one embodiment, in order to obtain the classification in the method of the invention, a reference population of patients with chronic liver disease is required. In one embodiment, the reference population may be a population of patients affected with a hepatitis virus, preferably with the hepatitis C virus. In one embodiment, the reference population contains at least about 500 patients, preferably at least about 700 patients, more preferably at least about 1000 patients.

The invention also relates to a non-invasive method for assessing the presence and severity of a liver lesion in a subject, comprising:
1) performing at least 3 binary logistic regressions on at least one variable, wherein the binary logistic regressions are performed on the same variable(s) but are each directed to a different single diagnostic target, thereby obtaining at least 3 scores;

1a) performing at least another binary logistic regression including the at least 3 scores obtained at step 1), wherein the diagnostic target of said binary logistic regression is a clinically relevant binary target, thereby identifying the significant single-targeted scores among those obtained by the binary logistic regressions of step 1), said significant single-targeted scores being independently associated with said clinically relevant binary diagnostic target;

1b) deriving a classification of liver lesion stages or grades for each of the single-targeted binary logistic regressions found significant in step 1a);

1c) combining the classifications of step 1b) into a multi-targeted classification of liver lesion stages or grades; and 2) combining the significant scores identified in step 1a) in a multiple linear regression, preferably a multiple linear regression with a stepwise selection of independent variables, to obtain a single multi-targeted score, thereby assessing the presence and severity of a liver lesion in the subject.

In one particular embodiment, the invention relates to a non-invasive method for assessing the presence and severity of liver fibrosis, including cirrhosis, in a subject, comprising:

1) performing at least 3 binary logistic regressions on at least one variable, wherein the binary logistic regressions are performed on the same variable(s) but are each directed to a different single diagnostic target, thereby obtaining at least 3 scores;

1a) performing at least another binary logistic regression including the at least 3 scores obtained at step 1), wherein the diagnostic target of said binary logistic regression is a clinically relevant binary target, thereby identifying the significant single-targeted scores among those obtained by the binary logistic regressions of step 1), said significant single-targeted scores being independently associated with said clinically relevant binary diagnostic target;

1b) deriving a classification of fibrosis stages for each of the single-targeted binary logistic regressions found significant in step 1a);

1c) combining the classifications of step 1b) into a multi-targeted classification of fibrosis stages; and 2) combining the significant scores identified in step 1a) in a multiple linear regression to obtain a single multi-targeted score, thereby assessing the presence and severity of liver fibrosis, including cirrhosis, in the subject.

In another embodiment, the invention relates to a non-invasive method for assessing the risk of death, including non liver-related death and/or liver-related death, or liver-related events, especially complications, in a subject, comprising:

1) performing at least 3 binary logistic regressions on at least one variable, wherein the binary logistic regressions are performed on the same variable(s) but are each directed to a different single diagnostic target, thereby obtaining at least 3 scores;

1a) performing at least another binary logistic regression including the at least 3 scores obtained at step 1), wherein the diagnostic target of said binary logistic regression is a clinically relevant binary target, thereby identifying the significant single-targeted scores among those obtained by the binary logistic regressions of step 1), said significant single-targeted scores being independently associated with said clinically relevant binary diagnostic target;

1b) deriving a classification of liver lesion stages or grades for each of the single-targeted binary logistic regressions found significant in step 1a);

1c) combining the classifications of step 1b) into a multi-targeted classification of liver lesion stages or grades; and 2) combining the significant scores identified in step 1a) in a multiple linear regression, preferably a multiple linear regression with a stepwise selection of independent variables, to obtain a single multi-targeted score, thereby assessing the risk of death, including non liver-related death and/or liver-related death, or liver-related events in the subject.

Thus, in one embodiment, the method of the invention comprises combining the classifications derived from each of the single-targeted binary logistic regression into a multi-targeted classification thereby determining to which liver lesion stages or grades (or class of lesion stages or grades) the subject belongs.

In one embodiment, the clinically relevant binary target of the at least another binary logistic regression performed in step 1a) is significant fibrosis and/or cirrhosis.

In one embodiment, the multi-targeted score obtained in step 2) is bounded and ranges from 0 to 1.

In one embodiment, the multiple linear regression of step 2) of the method of the invention is targeted to normalized Metavir F. In another embodiment, the multiple linear regression of step 2) of the method of the invention is targeted to the normalized (bounds: 0 and 1) multi-targeted test classification of step 1c).

Thus, in one embodiment, the multi-targeted test of the invention comprises a step of deriving a classification for each of the single-targeted score obtained by binary logistic regression and a step of combining the "single-targeted" classifications obtained into a multi-targeted classification.

In one embodiment, the "single-targeted" classifications are obtained by the classification method assigning lesion stages or grades into classes according to percentiles, as described in US 2014005500 which is hereby incorporated by reference.

In another embodiment, the "single-targeted" classifications are obtained by the classification method based on the reliable diagnostic intervals (RDIs) as described in US 2014005500 which is hereby incorporated by reference.

In the present invention, combining the classifications derived for each significant single-targeted score obtained by binary logistic regression into a multi-targeted classification is implemented with a specific original statistical technique described briefly below and illustrated in Example 3. In one embodiment, the multi-targeted classification of the invention is obtained with a segmentation method based on maximum accuracy by pairwise comparison of single-targeted classifications.

The objective is to select and combine the most accurate parts of the classifications obtained for the single-targeted binary logistic regressions (BLR) identified as significant in step 1a). The binary logistic regressions (BLR) found significant are expressed either in score (for cut-off determination) or in classification (for accuracy determination).

Intermediate classifications are generated (the number depending on the number of binary logistic regressions considered) before the final multi-targeted classification is obtained. For example, if three binary logistic regressions (BLR1, BLR2, BLR3) are found significant in step 1a), one intermediate classification is generated (BLR1/BLR2 or BLR2/BLR3 or BLR1/BLR3), before the final multi-targeted classification is obtained (BLR1/BLR2/BLR3).

First, the rate of correctly classified patients (or accuracy) is compared between two adjacent significant binary logistic regressions (BLR1 and BLR2, or BLR2 and BLR3, or BLR1 and BLR3). The aim is to determine the best cut-off maximizing the global accuracy rate including these two binary logistic regressions. The limits of the lesion classes or grades retained is determined by those of the corresponding scores.

For example, the accuracy is the sum of correctly classified patients by the BLR1 classification below the cut-off of BLR1 score and by the BLR2 classification beyond this cut-off; this calculation is repeated, from low to high score values, to find the best cut-off among increasing values of BLR1 score maximizing the global accuracy, with "global accuracy" meaning the sum of two accuracies. The same calculation is then repeated to determine the best cut-off of BLR2 score. Two combined classifications BLR1/BLR2 are thus obtained with cut-offs determined either by the first or the second BLR. The choice between the two combined classifications is determined mainly by the maximum global accuracy obtained and then by the maximum population size remaining available with BLR2 for the next calculation including BLR3.

The same calculations are then carried out to compare the BLR1/BLR2 classification to the BLR3 classification or the BLR2/BLR3 classification to the BLR1 classification or the BLR1/BLR3 classification to the BLR2 classification and the best combined BLR1/BLR2/BLR3 classification is determined.

If there are more than three binary logistic regressions, the same process is repeated until a final classification is obtained, said final classification combining parts of each of the classifications derived for the binary logistic regressions identified as significant in step 1a).

In one embodiment, the multi-targeted classification combining the classification obtained for each significant single-targeted binary logistic regression is obtained with a statistical method based on maximum accuracy by pairwise comparison.

In one embodiment, the method of the invention comprises performing at least 3, at least 4, at least 5, at least 6, at least 7, at least 8, at least 9, or at least 10 binary logistic regressions on at least one variable.

In one embodiment, the method of the invention comprises performing 3, 4, 5, 6, 7, 8, 9, or 10 binary logistic regressions on at least one variable.

In one embodiment, other suitable statistical analyses or combinations may substitute the binary logistic regressions of step 1). Examples of statistical analyses that may be used in step 1) of the multi-targeted test of the invention include, without being limited to, linear discriminant analysis or multivariate analysis.

In one embodiment, the method of the invention comprises performing at least 3 linear discriminant analyses on at least one variable.

In one embodiment, the method test of the invention comprises performing at least 3 multivariate analyses on at least one variable.

In one embodiment, the method of the invention comprises performing at least 3 binary logistic regressions on at least 1, at least 2, at least 3, at least 4, at least 5, at least 6, at least 7, at least 8, at least 9, or at least 10 variable(s).

In another embodiment, the method of the invention comprises performing at least 3 binary logistic regressions on 1, 2, 3, 4, 5, 6, 7, 8, 9, 10, 11, 12, 13, 14, or 15 variable(s).

According to one embodiment, said at least one variable may be selected from the group comprising biomarkers, clinical markers, qualitative markers, data obtained by a physical method of diagnosis, scores of fibrosis tests, descriptors of images of the liver tissue previously obtained by an imaging method, and mathematical combinations thereof.

In one embodiment, said at least one variable is a biomarker, also called sometimes biological marker.

In another embodiment, the multi-targeted test of the invention comprises performing at least 3 binary logistic regressions on a least two variables, at least one variable being a biomarker and the at least one other variable being selected from the group comprising biomarkers, clinical markers, qualitative markers, data obtained by a physical method of diagnosis, scores of fibrosis tests, descriptors of images of the liver tissue previously obtained by an imaging method, and mathematical combinations thereof.

In one embodiment, the sample obtained from a subject is a blood sample.

Thus, in one embodiment, the method of the invention comprises measuring biomarkers to carry out the binary logistic regressions of step 1).

In one embodiment, the method of the invention may also comprise obtaining a blood sample from the subject to measure biomarkers.

Examples of such biological markers include, without being limited to total cholesterol, HDL cholesterol (HDL), LDL cholesterol (LDL), AST (aspartate aminotransferase), ALT (alanine aminotransferase), platelets (PLT), prothrombin time (PT) or prothrombin index (PI) or INR (International Normalized Ratio), hyaluronic acid (HA or hyaluronate), hemoglobin, triglycerides, alpha-2 macroglobulin (A2M), gamma-glutamyl transpeptidase (GGT), urea, bilirubin (such as, for example, total bilirubin), apolipoprotein A1 (ApoA1), type III procollagen N-terminal propeptide (P3NP or P3P), gamma-globulins (GBL), sodium (Na), albumin (ALB) (such as, for example, serum albumin), ferritin (Fer), glucose (Glu), alkaline phosphatases (ALP), YKL-40 (human cartilage glycoprotein 39), tissue inhibitor of matrix metalloproteinase 1 (TIMP-1), TGF, cytokeratin 18, matrix metalloproteinase 2 (MMP-2) to 9 (MMP-9), haptoglobin, alpha-fetoprotein, creatinine, leukocytes, neutrophils, segmented leukocytes, segmented neutrophils, monocytes, ratios and mathematical combinations thereof, such as, for example AST/ALT (ratio), AST.ALT (product), AST/ALT+prothrombin, AST/ALT+hyaluronate.

In one embodiment, the biological markers are selected from the group comprising alpha-2 macroglobulin (A2M), hyaluronic acid (HA or hyaluronate), prothrombin index (PI), platelets (PLT), aspartate aminotransferase (AST), urea, gamma-glutamyl transpeptidase (GGT), alanine aminotransferase (ALT), ferritin (Fer), and glucose (Glu).

The biological markers may be measured in a blood sample obtained from the subject. Thus measuring the biological markers may consist in: the counting of cells in the blood (e.g., platelet count); the measuring of a protein concentration in the blood (e.g., alpha2-macroglogulin, haptoglobin, apolipoprotein A1, ferritin, albumin); the measuring of a compound concentration in the blood (e.g., urea, bilirubin, hyaluronic acid, glucose); the measuring of an enzyme activity in the blood (e.g., gamma-glutamyl transpeptidase, aspartate aminotransferase, alanine aminotransferase); or the assessment of the clotting ability of the blood (prothrombin index). Methods for carrying out such assays or counts are commonly used in biomedical laboratories and very well known in the field of diagnostics in hepatology.

These methods may use one or more monoclonal or polyclonal antibodies that recognize said protein in immunoassay techniques (such as, for example, radioimmunoassay or RIA, ELISA assays, Western blot, etc.), the analysis of the amounts of mRNA for said protein using the techniques of Northern blot, slot blot or PCR type, techniques such as an HPLC optionally combined with mass spectrometry, etc. The abovementioned enzyme activity assays use assays carried out on at least one substrate specific for each of these enzymes. International patent application WO 03/073822 lists methods that can be used to quantify alpha2 macroglobulin (A2M) and hyaluronic acid (HA or hyaluronate).

By way of examples, and in a non-exhaustive manner, a list of commercial kits or assays that can be used for the measurements of biomarkers carried out in the method of the invention, on blood samples, is given hereinafter:

- prothrombin time: the Quick time (QT) is determined by adding calcium thromboplastin (for example, Neoplastin CI plus, Diagnostica Stago, Asnieres, France) to the plasma and the clotting time is measured in seconds. To obtain the prothrombin time (PT), a calibration straight line is plotted from various dilutions of a pool of normal plasmas estimated at 100%. The results obtained for the plasmas of patients are expressed as a percentage relative to the pool of normal plasmas. The upper value of the PT is not limited and may exceed 100%;
- A2M: the assaying thereof is carried out by laser immunonephelometry using, for example, a Behring nephelometer analyzer. The reagent may be a rabbit antiserum against human A2M;
- HA: the serum concentrations are determined with an ELISA (for example: Corgenix, Inc. Biogenic SA 34130 Mauguio France) that uses specific HA-binding proteins isolated from bovine cartilage;
- PLT: blood samples are collected in vacutainers containing EDTA (ethylenediaminetetraacetic acid) (for example, Becton Dickinson, France) and can be analyzed on an Advia 120 counter (Bayer Diagnostic);
- Urea: assaying, for example, by means of a "Kinetic UV assay for urea" (Roche Diagnostics);
- GGT: assaying, for example, by means of a "gamma-glutamyl transferase assay standardized against Szasz" (Roche Diagnostics);
- Bilirubin: assaying, for example, by means of a "Bilirubin assay" (Jendrassik-Grof method) (Roche Diagnostics);
- ALT: assaying, for example, by "ALT IFCC" (Roche Diagnostics);
- AST: assaying, for example, by means of "AST IFCC" (Roche Diagnostics);
- Glucose: assaying, for example, by means of "glucose GOD-PAP" (Roche Diagnostics);
- Urea, GGT, bilirubin, alkaline phosphatases, sodium, glucose, ALT and AST can be assayed on an analyzer, for example, a Hitachi 917, Roche Diagnostics GmbH, D-68298 Mannheim, Germany;
- Gamma-globulins, albumin and alpha-2 globulins: assaying on protein electrophoresis, for example: capillary electrophoresis (Capillarys), SEBIA 23, rue M Robespierre, 92130 Issy Les Moulineaux, France.

For the biomarkers measured in the method of the present invention, the values obtained may be expressed in:

- mg/dl, such as, for example, for alpha2-macroglobulin (A2M);
- µg/l, such as, for example, for hyaluronic acid (HA or hyaluronate), or ferritin;
- g/l, such as, for example, for apolipoprotein A1 (ApoA1), gamma-globulins (GLB) or albumin (ALB);
- U/ml, such as, for example, for type III procollagen N-terminal propeptide (P3P);
- IU/l, such as, for example, for gamma-glutamyl transpeptidase (GGT), aspartate aminotransferases (AST), alanine aminotransferases (ALT) or alkaline phosphatases (ALP);
- µmol/l, such as, for example, for bilirubin;
- Giga/l, such as, for example, for platelets (PLT);
- %, such as, for example, for prothrombin time (PT);
- mmol/l, such as, for example, for triglycerides, urea, sodium (NA), glucose; or
- ng/ml, such as, for example, for TIMP1, MMP2, or YKL-40.

In one embodiment, said at least one variable being is a clinical marker.

In another embodiment, the method of the invention comprises performing at least 3 binary logistic regressions on a least two variables, at least one variable being a clinical marker and the at least one other variable being selected from the group comprising biomarkers, clinical markers, qualitative markers, data obtained by a physical method of diagnosis, scores of fibrosis tests, descriptors of images of the liver tissue previously obtained by an imaging method, and mathematical combinations thereof.

In one embodiment, the method of the invention thus comprises determining clinical markers to carry out the binary logistic regressions of step 1).

Examples of clinical markers include, without being limited to, body weight, body mass index, age, sex, hip perimeter, abdominal perimeter and the ratio thereof, such as for example hip perimeter/abdominal perimeter.

In one embodiment, the clinical markers are selected among body weight, age and sex.

In one embodiment, said at least one variable being is a qualitative marker.

In another embodiment, the multi-targeted test of the invention comprises performing at least 3 binary logistic regressions on a least two variables, at least one variable being a qualitative marker and the at least one other variable being selected from the group comprising biomarkers, clinical markers, qualitative markers, treatment data, data obtained by a physical method of diagnosis, scores of fibrosis tests, descriptors of images of the liver tissue previously obtained by an imaging method, and mathematical combinations thereof.

In one embodiment, the method of the invention thus comprises determining qualitative markers to carry out the binary logistic regressions of step 1).

Examples of qualitative markers include, without being limited to, diabetes, treatment data such as diabetes treatment or antiviral treatment, SVR (wherein SVR stands for sustained virologic response, and is defined as aviremia 6 weeks, preferably 12 weeks, more preferably 24 weeks after completion of antiviral therapy for chronic hepatitis C virus (HCV) infection), etiology, and NAFLD.

Regarding the qualitative marker "etiology", the person skilled in the art knows that said variable is a single or multiple qualitative marker, and that for liver disorders, etiology may be NAFLD, alcohol, virus or other. Thus, the qualitative marker might be expressed as NAFLD vs. others (single qualitative marker) or as NAFLD vs. reference etiology plus virus vs. reference etiology and so on (multiple qualitative marker).

In one embodiment, said at least one variable is a data obtained by a physical method of diagnosis, also sometimes called physical data.

In another embodiment, the method comprises performing at least 3 binary logistic regressions on a least two variables, at least one variable being a data obtained by a physical method of diagnosis and the at least one other variable being selected from the group comprising biomarkers, qualitative markers, data obtained by a physical method of diagnosis, scores of fibrosis tests, descriptors of images of the liver tissue previously obtained by an imaging method, and mathematical combinations thereof.

In the present invention, data obtained by a physical method of diagnosis include imaging data.

Thus, in one embodiment, the data obtained by a physical method of diagnosis are imaging data. Examples of imaging data include, without being limited to, data obtained by ultrasonography, especially Doppler-ultrasonography, by IRM, MNR or velocimetry.

In another embodiment, the data obtained by a physical method of diagnosis are elastometry data, also sometimes called elastography data. Examples of elastometry data include, without being limited to, Liver Stiffness Evaluation (LSE) or Spleen Stiffness Evaluation, which may be for example obtained by VCTE (Vibration Controlled Transient Elastography) also known as Fibroscan™, or by ARFI (Acoustic Radiation Force Impulse), SSI (Supersonic Shear Imaging), MNR elastometry or any other elastography technique.

In one embodiment, the method of the invention thus comprises performing at least 3 binary logistic regressions on at least one, preferably at least two, data obtained by Vibration Controlled Transient Elastography (VCTE) also known as Fibroscan, Acoustic Radiation Force Impulse (ARFI), supersonic shear imaging (SSI) elastometry, or MNR/MRI elastography.

In another embodiment, the multi-targeted test of the invention comprises performing at least 3 binary logistic regressions on a least two variables, at least one variable being a data obtained by Vibration Controlled Transient Elastography (VCTE) also known as Fibroscan, Acoustic Radiation Force Impulse (ARFI), supersonic shear imaging (SSI) elastometry, or MNR/MRI elastography and the at least one other variable being selected from the group comprising biomarkers, qualitative markers, data obtained by a physical method of diagnosis, scores of fibrosis tests, descriptors of images of the liver tissue previously obtained by an imaging method, and mathematical combinations thereof.

In a particular embodiment, the physical data is liver stiffness measurement (LSM), sometimes also called liver stiffness evaluation (LSE) preferably measured by VCTE (also known as Fibroscan™, Paris, France). In one embodiment, the measure by VCTE is performed with the M probe. Preferably, examination conditions are those recommended by the manufacturer, with the objective of obtaining at least 3 and preferably 10 valid measurements. Results may be expressed as the median (kilopascals) of all valid measurements, and as IQR (interquartile range) or as the ratio (IQR/median).

Thus, in one embodiment, the method of the invention comprises performing at least 3 binary logistic regressions on a least one variable, said at least one variable being obtained by VCTE (also known as Fibroscan™). In another embodiment, the method of the invention comprises performing at least 3 binary logistic regressions on a least two variables, with at least one variable being liver stiffness measurement (LSM) obtained by VCTE and the other variable being selected from the group comprising biomarkers, qualitative markers, data obtained by a physical method of diagnosis, scores of fibrosis tests, descriptors of images of the liver tissue previously obtained by an imaging method, and mathematical combinations thereof.

In another embodiment, the data obtained by a physical method of diagnosis are radiography data.

According to one embodiment, the data obtained by a physical method of diagnosis are obtained by a radiography method selected from X-ray, ultrasonography, computerized scanner, magnetic resonance imaging (MRI), functional magnetic resonance imaging, tomography, computed axial tomography, proton emission tomography (PET), single photon emission computed tomography or tomodensitometry.

In one embodiment, the method of the invention comprises performing at least 3 binary logistic regressions on a least one, preferably at least two, data obtained by X-ray, ultrasonography, computerized scanner, magnetic resonance imaging (MRI), functional magnetic resonance imaging, tomography, computed axial tomography, proton emission tomography (PET), single photon emission computed tomography or tomodensitometry.

In one embodiment, said at least one variable is a score of a non-invasive test, preferably a score of fibrosis test or steatosis test.

In another embodiment, the multi-targeted test of the invention comprises performing at least 3 binary logistic regressions on a least two variables, at least one variable being a score of non-invasive test, preferably a score of fibrosis test or steatosis test, and the at least one other variable being selected from the group comprising biomarkers, clinical markers, qualitative markers, data obtained by a physical method of diagnosis, scores of fibrosis tests, descriptors of images of the liver tissue previously obtained by an imaging method, and mathematical combinations thereof.

In one embodiment, the method of the invention thus comprises obtaining a score of fibrosis test, also sometimes called a fibrosis score, to carry out the binary logistic regressions of step 1).

In the present invention, a score of fibrosis test is obtained for a subject by carrying out a fibrosis test.

Fibrosis tests comprise determining markers in a subject and mathematically combining said markers to obtain a score, said score usually being a value ranging from 0 to 1. Examples of fibrosis tests (and related tests) include, without being limited to APRI, ELF score, Fibrospect, FIB-4, Hepascore, Fibrotest, Zeng score, NAFLD fibrosis score, FibroMeter™, CirrhoMeter™, CombiMeter™ (or Elasto-FibroMeter™ or FibrOMeter$^{VCTE}$™), InflaMeter™, Actitest, QuantiMeter™, P2/MS, and Elasto-Fibrotest.

In one embodiment, the multi-targeted test of the invention comprises performing at least 3 binary logistic regressions on at least one fibrosis score obtained with a fibrosis test selected from APRI, FIB4, Fibrotest, ELF score, FibroMeter™, Fibrospect or Hepascore, Zeng score, NAFLD fibrosis score, wherein said fibrosis test comprises the combination in a simple mathematical function such as an arithmetic operation, for example division, or a binary logistic regression of markers selected from biological markers and/or clinical markers.

In the present invention, fibrosis tests comprising combining biomarkers measured in a blood sample obtained from a subject are also referred to as "blood tests".

APRI is a blood test based on platelet and AST.

ELF (Enhanced Liver Fibrosis) score is a blood test based on hyaluronic acid, P3P, and TIMP-1.

Fibrospect is a blood test based on hyaluronic acid, TIMP-1 and A2M.

FIB-4 is a blood test based on platelet, AST, ALT and age.

Hepascore is a blood test based on hyaluronic acid, bilirubin, alpha2-macroglobulin, GGT, age and sex.

Fibrotest is a blood test based on alpha2-macroglobulin, haptoglobin, apolipoprotein A1, total bilirubin, GGT, age and sex.

Zeng score is a blood test based on GGT, A2M, HA and age.

NAFLD fibrosis score is a blood test based on AST, ALT, platelets, glucose, albumin, age and weight.

FibroMeter™ and CirrhoMeter™ together form a family of blood tests, the content of which depends on the cause of chronic liver disease and the diagnostic target. This blood test family is called FM family and detailed in Table 1 below.

blood test based on A2M, HA, and PI. The FibroMeter (FM S) recommended when the etiology of the suspected fibrosis is NAFLD (steatosis) is a blood test based on PLT, AST, ALT, ferritin, glucose, age and weight. CirrhoMeters are blood tests based on (i) at least six biological markers selected from A2M, HA, PI, PLT, AST, urea, and GGT; and (ii) the two clinical markers age and sex. The CirrhoMeter of the second generation (2G) recommended when the etiology of the suspected fibrosis is a viral infection (CM V 2G) is a blood test based on A2M, HA, PI, PLT, AST, urea, age and sex. The CirrhoMeter of the third generation (3G) recommended when the etiology of the suspected fibrosis is a viral infection (CM V 3G) is a blood test based on A2M, GGT, PI, PLT, AST, urea, age and sex.

In one embodiment, the tests of the FibroMeter and the CirrhoMeter family do not include the biological marker urea.

In one embodiment, markers combined in the tests of the FibroMeter and the CirrhoMeter family are used as single markers, e.g., A2M, HA or GGT, PI, PLT, AST, urea; or as

TABLE 1

Markers combined in the FibroMeter family of fibrosis tests.

| | Variables | | | | | | | | | | | | |
|---|---|---|---|---|---|---|---|---|---|---|---|---|---|
| | Age | Sex | Weight | A2M | HA | PI | PLT | AST | Urea | GGT | ALT | Fer | Glu |
| Cause: Virus | | | | | | | | | | | | | |
| FM V 1G | x | | | x | x | x | x | x | x | | | | |
| FM V 2G | x | x | | x | x | x | x | x | x | | | | |
| CM V 2G | x | x | | x | x | x | x | x | x | | | | |
| FM V 3G[a] | x | x | | x | | x | x | x | x | x | | | |
| CM V 3G[a] | x | x | | x | | x | x | x | x | x | | | |
| Cause: Alcohol | | | | | | | | | | | | | |
| FM A 1G | x | | | x | x | x | | | | | | | |
| FM A 2G | | | | x | x | x | | | | | | | |
| Cause: NAFLD (steatosis) | | | | | | | | | | | | | |
| FM S | x | | x | | | | x | x | | | x | x | x |

FM: FibroMeter, CM: CirrhoMeter, FM A: FibroMeter ALD (alcoholic liver disease, FM S: FibroMeter NAFLD
A2M: alpha-2 macroglobulin, HA: hyaluronic acid, PI: prothrombin index, PLT: platelets, Fer: ferritin, Glu: glucose
[a]HA is replaced by GGT FibroMeters are blood tests based on (i) at least three biological markers selected from A2M, HA, PI, PLT, AST, urea, GGT, ALT, ferritin and glucose; and (ii) optionally at least one clinical marker selected from age, sex and weight. The FibroMeter of the first generation (1G) recommended when the etiology of the suspected fibrosis is a viral infection (FM V 1G) is a blood test based on A2M, HA, PI, PLT, AST, urea and age. The FibroMeter of the second generation (2G) recommended when the etiology of the suspected fibrosis is a viral infection (FM V 2G) is a blood test based on A2M, HA, PI, PLT, AST, urea, age and sex. The FibroMeter of the third generation (3G) recommended when the etiology of the suspected fibrosis is a viral infection (FM V 3G) is a blood test based on A2M, GGT, PI, PLT, AST, urea, age and sex. The FibroMeter of the first generation (1G) recommended when the etiology of the suspected fibrosis is alcohol consumption (FM A 1G) is a blood test based on A2M, HA, PI and age. The FibroMeter of the second generation (2G) recommended when the etiology of the suspected fibrosis is alcohol consumption (FM A 2G) is a ratios of markers, such as, for example, AST/PLT or AST/ALT; or as arithmetic combinations, such as, for example, ((AST/ULN (e.g., 45))/platelets)×100 or (age×AST)/(platelets×ALT$^{0.5}$), wherein ULN is upper limit of normal.

CombiMeter™ or Elasto-FibroMeter or FibroMeter$^{VCTE}$™ is a family of tests based on the mathematical combination of variables of the FM family (as detailed in the Table 1 hereinabove) or of the result of a test of the FM family with VCTE (FIBROSCAN™) result. In one embodiment, said mathematical combination is a binary logistic regression.

InflaMeter™ is a companion test of FM family reflecting necro-inflammatory activity including ALT, A2M, PI, and platelets.

Actitest is a blood test, companion test of Fibrotest family, based on alpha-macroglobulin, haptoglobin, apolipoprotein A1, total bilirubin, GGT, ALT, age and sex.

QuantiMeter is a blood test targeted on area of fibrosis and based on (i) alpha2-macroglobulin, hyaluronic acid, prothrombin time, platelets when designed for alcoholic liver diseases, (ii) hyaluronic acid, prothrombin index, platelets, AST, ALT and glucose when designed for NAFLD, or (iii) alpha2-macroglobulin, hyaluronic acid, platelets, urea, GGT and bilirubin when designed for chronic viral hepatitis.

P2/MS is a blood test based on platelet count, monocyte fraction and segmented neutrophil fraction.

Elasto-Fibrotest is a test based on the mathematical combination of variables of Fibrotest or of the result of a Fibrotest, with LSM measurement, measured for example by Fibroscan™.

In one embodiment, the method of the invention comprises performing at least 3 binary logistic regressions combining at least two variables.

Many of the non-invasive fibrosis tests recently developed to assess the presence and/or severity of a liver lesion consists in the combination of at least two variables in a binary logistic regression.

Thus, in one embodiment, the method of the invention comprises performing at least 3 single-targeted fibrosis tests, wherein the fibrosis tests comprise:
  i. measuring variables selected from the group comprising biomarkers, clinical markers, qualitative markers, data obtained by a physical method of diagnosis, scores of fibrosis tests, descriptors of images of the liver tissue previously obtained by an imaging method, and mathematical combinations thereof; and
  ii. combining the variables in a binary logistic regression, thereby obtaining a score.

In one embodiment, the method of the invention comprises performing at least 3 single-targeted fibrosis tests, wherein the fibrosis tests comprise:
  i. measuring biological markers, also called biomarkers, and optionally clinical markers and optionally data obtained by a physical method of diagnosis; and
  ii. combining the markers in a binary logistic regression, thereby obtaining a score.

Examples of biological markers, also called biomarkers, and methods to measure said biological makers are presented hereinabove. Examples of clinical markers are presented hereinabove. Examples of data obtained by a physical method of diagnosis are presented hereinabove.

Examples of blood tests comprising measuring markers and combining said markers in a binary logistic regression include, without being limited to, ELF score, Fibrospect, Hepascore, Fibrotest, Zeng score, FibroMeter™, CirrhoMeter™, CombiMeter™ (or Elasto-FibroMeter or FibroMeterVCTE™) and Elasto-Fibrotest.

In one embodiment, the single-targeted fibrosis test comprises measuring at least two biomarkers and combining said markers in a binary logistic regression. Examples of such single-targeted fibrosis tests include, without being limited to, Fibrospect.

In another embodiment, the single-targeted fibrosis test comprises measuring at least one biomarker and at least one clinical marker and combining said markers in a binary logistic regression. Examples of such single-targeted fibrosis tests include, without being limited to, Hepascore, Fibrotest, FibroMeter™, and CirrhoMeter™.

In another embodiment, the single-targeted fibrosis test comprises determining at least one fibrosis score, or the markers combined in said fibrosis test, and at least one data obtained by a physical method of diagnosis. Examples of such single-targeted fibrosis tests include, without being limited to, CombiMeter™ (or Elasto-FibroMeter or FibroMeterVCTE™) and Elasto-Fibrotest.

According to one embodiment, the single-targeted fibrosis tests carried in step 1) of the method of the invention are FibroMeters™, each with a different single diagnostic target. In one embodiment, said FibroMeters™ are FibroMeters™ virus of second generation (FibroMeter$^{V2G}$). In another embodiment, said FibroMeters™ are FibroMeters™ virus of third generation (FibroMeter$^{V3G}$).

Thus, in one embodiment, the binary logistic regressions of step (1) of the non-invasive method of the invention combine the variables of FibroMeter™ (or CirrhoMeter™) as defined in the Table 1 hereinabove.

In one embodiment, the non-invasive method for assessing the severity of liver fibrosis, including cirrhosis, in a subject comprises:
  1) performing at least 3, at least 4, at least 5, at least 6 or at least 7 FibroMeters, each with a different single diagnostic target, thereby obtaining at least 3 scores;
  2) combining the at least 3 scores obtained in step 1) in a multiple linear regression, preferably a multiple linear regression with a stepwise selection of independent variables, to obtain a new multi-targeted score; and optionally;
  3) sorting the multi-targeted score obtained in step 2) in a classification of fibrosis, thereby determining to which fibrosis stage (or class of fibrosis stages) the subject belongs based on his/her multi-targeted score.

In one embodiment, the binary logistic regressions of step 1) correspond to a fibrosis test selected from the FibroMeter family of fibrosis tests or combinations thereof with Vibration Controlled Transient Elastography (VCTE) also known as Fibroscan.

In one embodiment, the method of the invention comprises performing at least 3 binary logistic regressions combining a score of fibrosis test and a data obtained by a physical method of diagnosis.

By score of fibrosis test, it is understood the score obtained when performing said fibrosis test.

Examples of fibrosis tests are presented hereinabove. Examples of data obtained by a physical method of diagnosing fibrosis are presented hereinabove.

US 2011/0306849 describes the combination of a blood test and physical data useful for the diagnostic of fibrosis or cirrhosis. US 2011/0306849 thus describes the combination of FibroMeter or CirrhoMeter with Fibroscan, resulting in a new score called "index". In particular US 2011/0306849 describes the combination of FibroMeter or CirrhoMeter with Fibroscan in a binary logistic regression.

The combination of FibroMeter or CirrhoMeter with Fibroscan is also known as CombiMeter or Elasto-FibroMeter or FibroMeter$^{VCTE}$ ™, as stated hereinabove. Elasto-FibroMeter is a family of tests based on the mathematical combination of variables of the FibroMeter family (as detailed in the Table 1 hereinabove) or of the result of a test of the FibroMeter family with Fibroscan result.

Thus, in one embodiment, the method of the invention comprises performing at least three binary logistic regressions combining FibroMeter or CirrhoMeter with Fibroscan. In other words, the method of the invention comprises determining at least three indexes, each addressing a different single target.

In one embodiment, said at least one variable is a descriptor of at least one image of the liver tissue previously obtained by an imaging method.

In another embodiment, the method of the invention comprises performing at least 3 binary logistic regressions on a least two variables, at least one variable being a descriptor of at least one image of the liver tissue previously obtained by an imaging method and the at least one other variable being selected from the group comprising biomarkers, clinical markers, qualitative markers, data obtained by a physical method of diagnosing fibrosis, scores of fibrosis tests, descriptors of images of the liver tissue previously obtained by an imaging method, and mathematical combinations thereof.

In the present invention, a descriptor of images of the liver tissue previously obtained by an imaging method refers to any computer-generated data associated with or derived from an image of the liver, such as, for example, an image obtained by microscopy or a radiological image. The image of the liver may be an electronic or digital image. The image of the liver may be recovered directly after the medical examination or may be a scanned image of the medical examination result. For example, the image of the liver may have been obtained from a liver biopsy sample.

US 2016/012583 describes an automated method for assessing the presence and/or the severity of lesions in an organ, based on the computerized analysis of a medical image of this organ. In particular US 2016/012583, which is hereby incorporated by reference, describes descriptors of images that may be useful for assessing the presence and/or the severity of a lesion in the liver through their combination to calculate a score.

In one embodiment, the at least one descriptor of images of the liver tissue combined in the binary logistic regressions of step 1) results from the analysis of an image obtained by an optical technique. In one embodiment, the optical technique may be microscopic physical imaging, such as, for example electron microscopy, second harmonic generation (SHG), multiphoton imaging, coherent anti-Stokes Raman scattering—CARS), two-photon excitation fluorescence (TPEF), diffuse optical imaging or event-related optical signal.

Examples of descriptors of images of the liver tissue that can be observed with optical or electronic microscopy include, but are not limited to (a) fractal dimension of the edges of the organ or fragment thereof, (b) linearity percentage of the edges, (c) nodularity of the curved and irregular edges of the organ (nodularity of the edges), (d) angularity, (e) length of the organ or fragment thereof, (f) length of a biopsy, such as, for example, (g) length of a liver biopsy, (h) length of numeric specimen, (i) height of the organ, (j) perimeter of the organ or fragment thereof, (k) mean and (l) total native perimeter of the organ, (m) smoothed perimeter of the organ, (n) ratio between the native and smoothed perimeters, also referred as anfractuosity, (o) largest perimeter of the organ, (p) indentation of the organ, (q) area of the organ or fragment thereof, (r) granularity percentage, (s) fragmentation, (t) mean intensity of the image on the red component, (u) mean intensity of the image on the green component, (v) mean intensity of the image on the blue component, (w) area of fibrosis, (x) fractal dimension of fibrosis, (y) mean of percentage of fibrosis around areas (i.e., nodularity percentage), (z) number of nodules, (aa) number of nodules with more than 30% of fibrosis around, (ab) area of steatosis, (ac) relative area of steatosis, (ad) fractal dimension of steatosis, (ae) area of porto-septal fibrosis, (af) fractal dimension of porto-septal fibrosis, (ag) area of peri-sinusoidal fibrosis, (ah) fractal dimension of peri-sinusoidal fibrosis, (ai) area of lobular peri-sinusoidal fibrosis, (aj) ratio of peri-sinusoidal fibrosis among the whole fibrosis (i.e., ratio of peri-sinusoidal fibrosis area), (ak) luminosity of fibrosis staining in the red, (al) green and/or (am) blue components, (an) luminosity of the parenchyma staining in the red, (ao) green and/or (ap) blue components, (aq) luminosity contrast between fibrosis and parenchyma, (ar) luminosity contrast between fibrosis and the organ or fragment thereof, (as) area of stellar fibrosis among the total surface of the liver biopsy specimen (i.e., whole area of stellar fibrosis), (at) area of stellar fibrosis among the surface of porto-septal regions (i.e., portal area of stellar fibrosis), (au) area of stellar fibrosis among the surface of lobular regions (i.e., lobular area of stellar fibrosis), (av) number of porto-septal regions; (aw) mean area of stellar fibrosis, (ax) mean area of porto-septal regions, (ay) number of bridges, (az) ratio of bridges among the porto-septal areas (i.e., portal ratio of bridges), (ba) area of fibrosis in the bridges, (bb) bridges thickness, (bc) bridges perimeter, (bd) bridges surface (i.e., bridge area), (be) portal distance, and (cm) number of fragments. The definitions of the above listed descriptors of images and the methods to obtain the above listed descriptors of images are enclosed in US 2016/012583.

In another embodiment of the invention, the at least one descriptor of images of the liver tissue combined in the binary logistic regressions of step 1) results from the analysis of an image obtained by a non-optical technique. In one embodiment, the non-optical technique may be radiography, such as, for example, X-ray, ultrasonography, computerized scanner, magnetic resonance imaging (MRI), functional magnetic resonance imaging, tomography, computed axial tomography, proton emission tomography (PET) or single photon emission computed tomography; nuclear medicine, such as, for example, scintigraphy; photoacoustic methods; thermal methods; or magnetoencephalography.

Examples of descriptors of images of the liver tissue that can be observed with radiology include, but are not limited to (a) fractal dimension of the edges of the organ or fragment thereof, (b) linearity percentage of the edges, (c) nodularity of the curved and irregular edges of the organ (nodularity of the edges), (d) angularity, (e) length of the organ or fragment thereof, (f) length of a biopsy, such as, for example, (g) length of a liver biopsy, (h) length of numeric specimen, (i) height of the organ, (j) perimeter of the organ or fragment thereof, (k) mean and (l) total native perimeter of the organ, (m) smoothed perimeter of the organ, (n) ratio between the native and smoothed perimeters, also referred as anfractuosity, (o) largest perimeter of the organ, (p) indentation of the organ, (q) area of the organ or fragment thereof, (r) granularity percentage, (t) mean intensity of the image on the red component, (u) mean intensity of the image on the green component, (v) mean intensity of the image on the blue component, (ak) luminosity of fibrosis staining in the red, (al) green and/or (am) blue components, (an) luminosity of the parenchyma staining in the red, (ao) green and/or (ap) blue components, (bf) organ fat ratio, (bg) abdominal fat ratio, (bh) hypertrophy of liver segment I, (bi) surface of the segment I, (bj) width of the liver segment IV, (bk) ratio between segment I and segment IV dimensions, (bl) furrow thickness, (bm) surface of the furrow I, (bn) internal nodularity in the liver, (bo) diameter of the portal vein, (bp) heterogeneity of the density intensity, (bq) fractal organization of the organ, (br) mean total density of the image, (bs) standard deviation of total density of the image, (bt) coefficient of variation of total density of the image, (bu) median total density of the image, (bv) interquartile range of total density of the image, (bw) ratio between interquartile range of total density and median of total density of the image, (bx) mean density of a region of interest (ROI) on the image, (by) standard deviation of ROI density on the image, (bz) coefficient of variation of ROI density on the image, (ca) median ROI density on the image, (cb) interquartile range of ROI density on the image, (cc) ratio between interquartile range of ROI density and median of ROI density on the image, (cd)

mean surface of the organ or fragment thereof, (ce) total surface of the organ or fragment thereof, total mean surface of the organ or fragment thereof, (cf) ratio between the organ perimeter and the organ surface, (cg) ratio between spleen surface and liver surface, (ch) ratio between spleen perimeter and liver perimeter, (ci) ratio between segment I surface and liver surface, (cj) Arantius furrow thickness, (ck) Arantius furrow surface, and (cl) portal furrow thickness. The definitions of the above listed descriptors of images and the methods to obtain the above listed descriptors of images are enclosed in US 2016/012583.

In one embodiment, the at least one descriptor of images of the liver tissue combined in the binary logistic regressions of step 1) results from the analysis of an image obtained by CT scan, also called tomodensitometry (TDM).

In one embodiment, the method of the invention comprises performing at least 3 binary logistic regressions on a least two descriptors of images of the liver tissue.

In one embodiment, the method of the invention comprises performing at least 3 binary logistic regressions on a least 3, at least 4, at least 5, at least 6, at least 7, at least 8, at least 9 or at least 10 descriptors of images of liver tissue.

In one embodiment, the method of the invention comprises performing at least 3 binary logistic regressions on at least one, preferably at least two, descriptor(s) of images of liver tissue selected from fractal dimension of porto-septal fibrosis, fractal dimension of peri-sinusoidal fibrosis, ratio of peri-sinusoidal fibrosis area (expressed in %), whole area of stellar fibrosis (expressed in %), portal area of stellar fibrosis (expressed in %), mean portal distance (expressed in µm), number of bridges, portal ratio of bridges (expressed in %), mean bridge thickness (expressed in µm), mean granularity percentage (expressed in %), mean nodularity percentage (expressed in %), fragmentation index (expressed in %), and edge linearity percentage (expressed in %).

In another embodiment, the method of the invention comprises performing at least 3 binary logistic regressions on at least one, preferably at least two, more preferably all, of the following descriptors of images of liver tissue selected from linearity percentage of the edges, mean of percentage of fibrosis around areas (i.e., nodularity percentage), area of stellar fibrosis among the total surface of the tissue specimen, number of bridges and bridges thickness.

In another embodiment, the method of the invention comprises performing at least 3 binary logistic regressions on at least one, preferably at least two, more preferably all, of the following descriptors of images of liver tissue selected from mean area of porto-septal regions, bridges perimeter, ratio of bridges among the porto-septal areas, mean of percentage of fibrosis around areas (i.e., nodularity percentage), area of fibrosis in the bridges and fractal dimension of peri-sinusoidal fibrosis.

In another embodiment, the method of the invention comprises performing at least 3 binary logistic regressions on at least one, preferably at least two, more preferably all, of the following descriptors of images of liver tissue selected from perimeter of the liver organ, tissue or fragment thereof, area of fibrosis in the bridges, fractal dimension of porto-septal fibrosis, ratio of peri-sinusoidal fibrosis among the whole fibrosis, length of the liver organ, tissue or fragment thereof, fractal dimension of peri-sinusoidal fibrosis and anfractuosity descriptors (native perimeter, smoothed perimeter and ratio between both perimeters).

In another embodiment, the method of the invention comprises performing at least 3 binary logistic regressions on at least one, preferably at least two, more preferably all, of the following descriptors of images of liver tissue selected from interquartile range of total density, Arantius furrow thickness, mean native liver perimeter, mean total spleen perimeter, and ratio spleen surface to liver surface.

In another embodiment, the method of the invention comprises performing at least 3 binary logistic regressions on at least one, preferably at least two, variables selected from interquartile range of total density, Arantius furrow thickness, mean native liver perimeter, mean total spleen perimeter, ratio spleen surface to liver surface, VCTE also known as Fibroscan, prothrombin time (PI), alpha2-macroglobulin (A2M) and aspartate aminotransferases (AST).

In another embodiment, the method of the invention comprises performing at least 3 binary logistic regressions on at least 1, at least 2, at least 3, at least 4, at least 5, at least 6, at least 7, at least 8, at least 9 or at least 10 descriptor(s) of images of liver tissue selected from linearity percentage of the edges, mean of percentage of fibrosis around areas (i.e., nodularity percentage), area of stellar fibrosis among the total surface of the liver biopsy specimen, number of bridges, bridges thickness, mean area of porto-septal regions, bridges perimeter, ratio of bridges among the porto-septal areas, area of fibrosis in the bridges and fractal dimension of peri-sinusoidal fibrosis, perimeter of the organ, tissue or fragment thereof, fractal dimension of porto-septal fibrosis, ratio of peri-sinusoidal fibrosis among the whole fibrosis, length of the organ, tissue or fragment thereof, anfractuosity descriptors (native perimeter, smoothed perimeter and ratio between both perimeters), fractal dimension of fibrosis, interquartile range of total density, Arantius furrow thickness, mean native liver perimeter, mean total spleen perimeter, ratio spleen surface to liver surface and mathematic combination thereof.

In another embodiment, the method of the invention comprises performing at least 3 binary logistic regressions on at least two descriptors of at least one image of the liver tissue of the subject previously obtained by an imaging method, said descriptors being selected from the group comprising linearity percentage of the edges, mean of percentage of fibrosis around areas (i.e., nodularity percentage), area of stellar fibrosis among the total surface of the LB specimen, number of bridges, bridges thickness, mean area of porto-septal regions, bridges perimeter, ratio of bridges among the porto-septal areas, area of fibrosis in the bridges and fractal dimension of peri-sinusoidal fibrosis, perimeter of the organ, tissue or fragment thereof, fractal dimension of porto-septal fibrosis, ratio of peri-sinusoidal fibrosis among the whole fibrosis, length of the organ, tissue or fragment thereof, anfractuosity descriptors (native perimeter, smoothed perimeter and ratio between both perimeters), fractal dimension of fibrosis, interquartile range of total density, Arantius furrow thickness, mean native liver perimeter, mean total spleen perimeter, ratio spleen surface to liver surface and mathematic combination thereof.

The invention relates to a non-invasive method for diagnosing a liver lesion, preferably liver fibrosis or cirrhosis, in a subject with a multi-targeted diagnostic test as described hereinabove.

The invention also relates to a non-invasive method for assessing the risk of death, especially liver-related death, or liver-related events, especially complications, in a subject with a multi-targeted diagnostic test as described hereinabove.

According to one embodiment, the subject is a human patient. In one embodiment, the subject is a male. In another embodiment, the subject is a female. In one embodiment, the subject is an adult. According to the present invention, an adult is a subject above the age of 18, 19, 20 or 21 years. In another embodiment, the subject is a child. According to the present invention, a child is a subject below 21, 20, 19 or 18 years.

In one embodiment, the subject is at risk of suffering or is suffering from a condition selected from the group comprising a liver impairment, a chronic liver disease, a hepatitis viral infection especially an infection caused by hepatitis B, C or D virus, an hepatoxicity, a liver cancer, a steatosis, a non-alcoholic fatty liver disease (NAFLD), a non-alcoholic steato-hepatitis (NASH), an autoimmune disease, a metabolic liver disease and a disease with secondary involvement of the liver.

According to an embodiment, hepatoxicity is alcohol induced hepatoxicity and/or drug-induced hepatoxicity (i.e., any xenobiotic compound like alcohol or drug).

According to an embodiment, autoimmune disease is selected from the group consisting of autoimmune hepatitis (AIH), primary biliary cirrhosis or cholangitis (PBC) and primary sclerosing cholangitis (PSC).

According to an embodiment, metabolic liver disease is selected from the group consisting of hemochromatosis, Wilson's disease and alpha 1 anti-trypsin deficiency.

According to an embodiment, said disease with a secondary involvement of the liver is celiac disease or amyloidosis.

The method of the invention comprises carrying out at least 3 binary logistic regressions on at least one variable, wherein the binary logistic regressions are performed on the same variable(s) but are each directed to a different single diagnostic target.

Within the present invention, the term "diagnostic target" refers to the main objective of a diagnostic test. According to the method of the invention, the binary logistic regressions of step 1) are single-targeted binary tests and thus their main objective is to assess the presence/absence (yes/no) of the targeted lesion.

According to one embodiment, the diagnostic target corresponds to a stage of the reference system or reference classification. According to another embodiment, the diagnostic target corresponds to a combination of stages of the reference system or reference classification.

According to one embodiment, the diagnostic target corresponds to a stage of the Metavir classification. In one embodiment, each of the at least 3 binary logistic regressions are directed to a different Metavir stage. In another embodiment, the method of the invention comprises carrying out 4 binary logistic regressions directed to the Metavir stages F1, F2, F3, and F4, i.e., F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4).

According to another embodiment, the diagnostic target of at least one of the binary logistic regression of step 1) is a combination of the type one stage versus the others, e.g., F2 vs. F0+F1+F3+F4. In one embodiment, the method of the invention comprises carrying out 7 binary logistic regressions, directed to F≥1 (F≥1 vs. F0, i.e., F0 vs. F1+F2+F3+F4), F≥2 (F≥2 vs. F≤1, i.e., F0+F1 vs. F2+F3+F4), F≥3 (F≥3 vs. F≤2, i.e., F0+F1+F2 vs. F3+F4), F4 (F4 vs. F≤3, i.e., F0+F1+F2+F3 vs. F4), F1 vs. F0+F2+F3+F4, F2 vs. F0+F1+F3+F4, and F3 vs. F0+F1+F2+F4. In another embodiment, the method of the invention comprises carrying out 10 binary logistic regressions, directed to F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4), F1 vs. F0+F2+F3+F4, F2 vs. F0+F1+F3+F4, F3 vs. F0+F1+F2+F4, F1+F2 vs. F0+F3+F4, F2+F3 vs. F0+F1+F4 and F1+F2+F3 vs. F0+F4.

According to another embodiment, the diagnostic target corresponds to a grade of necrotico-inflammatory activity of the Metavir classification (Metavir A). In one embodiment, each of the at least 3 binary logistic regressions are directed to a different Metavir A grade.

According to another embodiment, the diagnostic target corresponds to a grade or stage of the histological activity index (HAI). In one embodiment, each of the at least 3 binary logistic regressions are directed to a different HAI grade or stage.

According to another embodiment, the diagnostic target corresponds to a grade or stage of the Ishak system. In one embodiment, each of the at least 3 binary logistic regressions are directed to a different Ishak grade or stage.

According to another embodiment, the diagnostic target corresponds to a grade or a stage of the Kleiner grading/staging devoted to NAFLD, also known as the NASH Clinical Research Network (NASH-CRN) system. In one embodiment, each of the at least 3 binary logistic regressions are directed to a different NASH-CRN grade or stage.

Another object of the invention is a non-invasive method for assessing the risk of death, especially liver-related death, or liver-related events, especially complications, in a subject with a multi-targeted diagnostic test as described hereinabove.

In one embodiment, the method of the invention comprising carrying out a multi-targeted test is for assessing the risk of death and/or liver-related death, in a subject.

In another embodiment, the method of the invention comprising carrying out a multi-targeted test is for assessing the liver-related events, especially complications, in a subject.

In one particular embodiment, the multi-targeted classification obtained at step 1c) of the multi-targeted test of the invention is used for assessing the risk of liver-related death in a subject.

In one embodiment, the terms "death" and "mortality" both refer to overall death or mortality (which may also be referred as all-cause death or mortality) and/or to liver-related death or mortality. Examples of causes of liver-related deaths include, but are not limited to, deaths consecutive to a portal hypertension related hemorrhage, deaths consecutive to an esophageal or gastric varice-related hemorrhage, a hepatocellular carcinoma, ascites, encephalopathy, liver failure with sepsis, acute on chronic liver failure, hepato-renal syndrome, hepato-pulmonary syndrome or other liver decompensation.

In one embodiment, the term "liver-related event, especially complications" refers to a liver-related event or complication requiring specific therapy or care, such as, for example, ascites, encephalopathy, jaundice (which may be defined as serum bilirubin >50 µmol/l), occurrence of large esophageal varices (preferably having a diameter ≥5 mm, and/or preferably a diameter ≥25% of esophageal circumference), variceal bleeding, gastro-intestinal hemorrhage (such as, for example, due to portal hypertension), hepato-renal syndrome, hepato-pulmonary syndrome, hepatocellular carcinoma, hepatic transplantation, esophageal varices, portal hypertension superior or equal to a predetermined threshold (such as, for example, hepatic vein pressure gradient superior or equal to 10 mm Hg or superior or equal to 12 mm Hg), severe infection (such as, for example, septic shock).

In one embodiment, the term "liver-related event, especially complication" refers to the progression of the liver disease or disorder in a patient, such as, for example, the appearance of cirrhosis in a fibrotic non-cirrhotic patient, or the fact, for a patient, to cross a predetermined threshold (such as, for example, FibroMeter result superior or equal to 0.982, or Fibroscan result superior or equal to 14 kPa).

According to the invention, death (including all-cause death and liver-related death) does not refer to a liver-related event, especially complication.

In one embodiment, the method of the invention is for predicting the first liver-related event, especially complication, in a patient.

In one embodiment of the invention, the prognostic method of the invention is for assessing the risk of death or of a liver-related event within a period of at least 3 months, preferably 3 months, 6 months, 9 months, 1, 2, 3, 4, 5, 6, 7, 8, 9, or 10 years as of date of assessment.

Advantageously, in one embodiment, the invention relates to a non-invasive method for assessing the presence and severity of liver fibrosis, including cirrhosis, in a subject, comprising:
1) performing 4 binary logistic regressions on the variables of the FibroMeter family of fibrosis tests, said 4 binary logistic regressions targeting the Metavir stage F1, F2, F3 and F4, thereby obtaining 4 scores;
2) combining the 4 scores in a multiple linear regression, preferably a multiple linear regression with a stepwise selection of independent variables, to obtain a single multi-targeted score; and
3) optionally positioning the multi-targeted score obtained in step 2) in a classification of fibrosis, thereby determining to which class of fibrosis stages the subject belongs based on their multi-targeted score.

Thus, advantageously, in one embodiment, the invention relates to a non-invasive method for diagnosing liver fibrosis, including cirrhosis, in a subject comprising:
1) performing 4 FibroMeters, targeting the Metavir stage F1, F2, F3 and F4, i.e., F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4), thereby obtaining 4 scores;
2) combining the 4 scores in a multiple linear regression, preferably a multiple linear regression with a stepwise selection of independent variables, to obtain a single multi-targeted score; and
3) optionally positioning the multi-targeted score obtained in step 2) in a classification of fibrosis, thereby determining to which fibrosis stage (or class of fibrosis stages) the subject belongs based on his/her multi-targeted score.

In one embodiment, the invention relates to a non-invasive method for diagnosing liver fibrosis, including cirrhosis, in a subject comprising:
1) performing 7 FibroMeters, targeting the combinations of Metavir stages: F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4), F1 vs. F0+F2+F3+F4, F2 vs. F0+F1+F3+F4, F3 vs. F0+F1+F2+F4, thereby obtaining 7 scores;
2) combining the 7 scores in a multiple linear regression, preferably a multiple linear regression with a stepwise selection of independent variables, to obtain a single multi-targeted score; and
3) optionally positioning the multi-targeted score obtained in step 2) in a classification of fibrosis, thereby determining to which fibrosis stage (or class of fibrosis stages) the subject belongs based on his/her multi-targeted score.

In one embodiment, the invention relates to a non-invasive method for diagnosing liver fibrosis, including cirrhosis, in a subject comprising:
1) performing 10 FibroMeters, targeting the combinations of Metavir stages: F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4), F1 vs. F0+F2+F3+F4, F2 vs. F0+F1+F3+F4, F3 vs. F0+F1+F2+F4, F1+F2 vs. F0+F3+F4, F2+F3 vs. F0+F1+F4 and F1+F2+F3 vs. F0+F4, thereby obtaining 10 scores;
2) combining the 10 scores in a multiple linear regression, preferably a multiple linear regression with a stepwise selection of independent variables, to obtain a single multi-targeted score; and
3) optionally positioning the multi-targeted score obtained in step 2) in a classification of fibrosis, thereby determining to which fibrosis stage (or class of fibrosis stages) the subject belongs based on his/her multi-targeted score.

In another embodiment, the invention relates to a non-invasive method for assessing the presence and severity of liver fibrosis, including cirrhosis, in a subject comprising:
1) performing 4 binary logistic regressions on at least one liver stiffness measurement obtained by VCTE (also known as Fibroscan™), said 4 binary logistic regressions targeting the Metavir stage F1, F2, F3 and F4, i.e., F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4), thereby obtaining 4 scores;
2) combining the 4 scores in a multiple linear regression, preferably a multiple linear regression with a stepwise selection of independent variables, to obtain a single multi-targeted score;
3) optionally positioning the multi-targeted score obtained in step 2) in a classification of fibrosis, thereby determining to which fibrosis stage (or class of fibrosis stages) the subject belongs based on his/her multi-targeted score.

In one embodiment, the invention relates to a non-invasive method for diagnosing liver fibrosis, including cirrhosis, in a subject, with a multi-targeted diagnostic test comprising:
1) performing 7 binary logistic regressions on at least one liver stiffness measurement obtained by VCTE (also known as Fibroscan™), each binary logistic regression being directed to a different single diagnostic target, wherein the diagnostic targets are the combinations of Metavir stages: F≥1 vs. F=0 (corresponding to F0 vs. F1+F2+F3+F4), F≥2 vs. F≤1 (corresponding to F0+F1 vs. F2+F3+F4), F≥3 vs. F≤2 (corresponding to F0+F1+F2 vs. F3+F4), F=4 vs. F≤3 (corresponding to F0+F1+F2+F3 vs. F4), F1 vs. F0+F2+F3+F4, F2 vs. F0+F1+F3+F4, F3 vs. F0+F1+F2+F4, thereby obtaining 7 scores;
2) combining the 7 scores in a multiple linear regression, preferably a multiple linear regression with a stepwise selection of independent variables, to obtain a single multi-targeted score;

3) optionally positioning the multi-targeted score obtained in step 2) in a classification of fibrosis, thereby determining to which fibrosis stage (or class of fibrosis stages) the subject belongs based on his/her multi-targeted score.

In one embodiment, the invention relates to a non-invasive method for diagnosing liver fibrosis, including cirrhosis, in a subject comprising:

1) performing 10 binary logistic regressions on at least one liver stiffness measurement obtained by VCTE (also known as Fibroscan™), each binary logistic regression being directed to a different single diagnostic target, wherein the diagnostic targets are the combinations of Metavir stages: $F \geq 1$ vs. $F=0$ (corresponding to F0 vs. F1+F2+F3+F4), $F \geq 2$ vs. $F \leq 1$ (corresponding to F0+F1 vs. F2+F3+F4), $F \geq 3$ vs. $F \leq 2$ (corresponding to F0+F1+F2 vs. F3+F4), $F=4$ vs. $F \leq 3$ (corresponding to F0+F1+F2+F3 vs. F4), F1 vs. F0+F2+F3+F4, F2 vs. F0+F1+F3+F4, F3 vs. F0+F1+F2+F4, F1+F2 vs. F0+F3+F4, F2+F3 vs. F0+F1+F4 and F1+F2+F3 vs. F0+F4, thereby obtaining 10 scores;
2) combining the 10 scores in a multiple linear regression, preferably a multiple linear regression with a stepwise selection of independent variables, to obtain a single multi-targeted score; and
3) optionally positioning the multi-targeted score obtained in step 2) in a classification of fibrosis, thereby determining to which fibrosis stage (or class of fibrosis stages) the subject belongs based on his/her multi-targeted score.

In one embodiment, the method of the invention is computer implemented.

In one embodiment, the method of the invention is implemented with a microprocessor comprising a software configured to calculate a single multi-targeted score value resulting from the combination, in a multiple linear regression, of at least 3 scores obtained from at least 3 binary logistic regressions on at least one variable, wherein the binary logistic regressions are performed on the same variable(s) but are each directed to a different single diagnostic target.

Another object of the present invention is thus a computer software for implementing the method of the invention.

Thus, the invention also relates to a microprocessor to implement a non-invasive method for diagnosing liver fibrosis or cirrhosis in a subject with a multi-targeted diagnostic test as described hereinabove.

The present invention also relates to a method for monitoring a patient, wherein said method comprises implementing at time intervals the non-invasive method of the invention, thereby assessing the evolution of said patient by comparing the values of the multi-targeted scores obtained at time intervals by the patient.

In one embodiment, the non-invasive method of the invention is carried out every 3 months, every 6 months, every 9 months, every 12 months, every 15 months, every 18 months, every 24 months, or every 36 months.

The present invention also relates to a tool for helping in medical decisions regarding a patient suffering from a liver disease or condition, wherein said method comprises (i) implementing the non-invasive method of the invention and (ii) selecting in a database the pharmaceutical compositions which could be suitable for the patient according to the value of the multi-targeted score obtained by the patient.

In one embodiment, the method of the invention is implemented before the administration of a treatment to a patient and at least once during or after the administration of a treatment to said patient.

In another embodiment, the method of the invention is implemented before the administration of a treatment to a patient and at regular time intervals during the administration of a treatment to said patient.

In one embodiment, the method of the invention is implemented yearly for a single patient. In another embodiment, the method of the invention is repeated every 3 months, every 6 months, every 9 months, every 12 months, every 15 months, every 18 months, every 24 months, or every 36 months for a single patient.

The present invention also relates to a method for implementing an adapted patient care for an individual identified as suffering from a liver lesion, such as for example, liver fibrosis or cirrhosis.

Thus, the present invention relates to a method for treating an individual suffering from a liver lesion, preferably liver fibrosis or cirrhosis, comprising:

determining in the individual the presence and severity of a liver lesion, preferably liver fibrosis or cirrhosis, as described hereinabove by:
1) performing at least 3 binary logistic regressions on at least one variable, wherein the binary logistic regressions are performed on the same variable(s) but are each directed to a different single diagnostic target, thereby obtaining at least 3 scores; and
2) combining the at least 3 scores obtained in step 1) in a multiple linear regression to obtain a new multi-targeted score useful for assessing the presence and severity of a liver lesion in the subject; and
implementing an adapted patient care depending on the severity of the liver lesion, preferably liver fibrosis or cirrhosis.

In one embodiment, the method of the invention comprises:

determining in the individual the presence and severity of a liver lesion, preferably liver fibrosis or cirrhosis, as described hereinabove by:
1) performing at least 3 binary logistic regressions on at least one variable, wherein the binary logistic regressions are performed on the same variable(s) but are each directed to a different single diagnostic target, thereby obtaining at least 3 scores;
2) combining the at least 3 scores obtained in step 1) in a multiple linear regression, preferably a multiple linear regression with a stepwise selection of independent variables, to obtain a new multi-targeted score; and
3) positioning the multi-targeted score obtained in step 2) in a classification of liver lesion stages or grades, thereby determining to which lesion stage or grade the subject belongs based on his/her multi-targeted score; and
implementing an adapted patient care depending on the severity of the liver lesion, preferably liver fibrosis or cirrhosis.

In one embodiment, the method of the invention comprises:

determining in the individual the presence and severity of a liver lesion, preferably liver fibrosis or cirrhosis, as described hereinabove by:
1) performing at least 3 binary logistic regressions on at least one variable, wherein the binary logistic regressions are performed on the same variable(s) but are each directed to a different single diagnostic target, thereby obtaining at least 3 scores;

1a) performing at least another binary logistic regression including the at least 3 scores obtained at step 1), wherein the diagnostic target of said binary logistic regression is a clinically relevant binary target, thereby identifying the significant single-targeted scores among those obtained by the binary logistic regressions of step 1), said significant single-targeted scores being independently associated with said clinically relevant binary diagnostic target;

1b) deriving a classification of liver lesion stages or grades for each of the single-targeted binary logistic regressions found significant in step 1a);

1c) combining the classifications of step 1b) into a multi-targeted classification of liver lesion stages or grades; and 2) combining the significant scores identified in step 1a) in a multiple linear regression, preferably a multiple linear regression with a stepwise selection of independent variables, to obtain a single multi-targeted score, thereby assessing the presence and severity of a liver lesion in the subject; and implementing an adapted patient care depending on the severity of the liver lesion, preferably liver fibrosis or cirrhosis.

In one embodiment, the individual is determined to suffer from liver fibrosis at Metavir stage F1 and the adapted patient care consists in monitoring said individual by assessing the fibrosis severity at regular intervals.

In one embodiment, the fibrosis severity is assessed every 3 months, every 6 months, every 9 months, every 12 months, every 15 months, every 18 months, every 24 months, or every 36 months.

In one embodiment, the individual is determined to suffer from liver fibrosis at Metavir stage F≥2 and the adapted patient care consists in administering without delay at least one therapeutic agent or starting a complication screening program for applying early prophylactic or curative treatment.

In one embodiment, the individual is determined to suffer from severe liver fibrosis at Metavir stage F≥3 and the adapted patient care consists in administering without delay at least one therapeutic agent and optionally starting a complication screening program for applying early prophylactic or curative treatment.

In one embodiment, the individual is determined to suffer from cirrhosis, i.e., liver fibrosis at Metavir stage F4 (F=4), and the adapted patient care consists in administering without delay at least one therapeutic agent and starting a complication screening program for applying curative treatment.

Examples of therapeutic agents include, but are not limited to, bezafibrate, S-adenosyl-L-methionine, S-nitrosol-N-acetylcystein, silymarin, phosphatidylcholine, N-acetylcysteine, resveratrol, vitamin E, pentoxyphilline (or pentoxyfilline) alone or in combination with tocopherol, pioglitazone alone or in combination with vitamin E, lovaza (fish oil), PPC alone or in combination with an antiviral therapy (e.g., IFN), INT747, peginterferon 2b (pegylated IFNalpha-2b), a combination of infliximab, and ribavirin, stem cell transplantation (in particular MSC transplantation), candesartan, losartan, telmisartan, irbesartan, ambrisentan, FG-3019, *Phyllanthus urinaria*, Fuzheng Huayu, warfarin, insulin, colchicine, corticosteroids, naltrexone, RF260330, sorafenib, imatinib mesylate, nilotinib, pirfenidone, halofuginone, polaorezin, gliotoxin, sulfasalazine, rimonabant, simtuzumab, GR-MD-02, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32, topiramate, disulfiram, naltrexone, acamprosate, baclofen, methadone, buprenorphine, orlistat, metformin, atorvastatin, ezetimine, ARBs, EPL, EPA-E, multistrain biotic (*L. rhamnosus, L. bulgaricus*), obeticholic acid, elafibranor (GFT505), DUR-928, GR-MD, 02, aramchol, RG-125, cenicriviroc CVC, rosiglitazone, MSDC-0602K, GS-9674, LJN452, LMB763, EDP-305, elafibranor, saroglitazar, IVA337, NGM282, PF-05231023, BMS-986036, aramchol, volixibat, GS-0976, liraglutide, semaglutide exenatide, taspoglutide, taurine, polyenephosphatidylcholine, MGL-3196, vitamin C, GS-4997, sitagliptin, alogliptin, vildagliptin, saxagliptin, linagliptin, PXS-4728A, VLX-103, hyperimmune bovine clostrum, nalmefene, emricasan, milk thistle; and probiotics and combinations thereof.

In one embodiment, the at least one therapeutic agent is an antifibrotic agent selected from the group consisting of simtuzumab, GR-MD-02, stem cell transplantation (in particular MSC transplantation), *Phyllanthus urinaria*, Fuzheng Huayu, S-adenosyl-L-methionine, S-nitrosol-N-acetylcystein, silyrnarin, phosphatidylcholine, N-acetylcysteine, resveratrol, vitamin E, losartan, telmisartan, naltrexone, RF260330, sorafenib, imatinib mesylate, nilotinib, INT747, FG-3019, oltipraz, pirfenidone, halofuginone, polaorezin, gliotoxin, sulfasalazine, rimonabant and combinations thereof.

In one embodiment, the at least one therapeutic agent is for treating the underlying cause responsible for liver fibrosis, and/or ameliorating or alleviating the symptoms associated with the underlying cause responsible for liver fibrosis, including liver fibrosis.

In one embodiment, the underlying cause responsible for liver fibrosis is selected from the group consisting of a hepatitis viral infection, a hepatotoxicity, a non-alcoholic fatty liver disease (NAFLD), an autoimmune disease, a metabolic liver disease and a disease with secondary involvement of the liver.

In one embodiment, the underlying cause responsible for liver fibrosis is a viral infection and the at least one therapeutic agent is selected from the group consisting of interferon, peginterferon 2b (pegylated IFNalpha-2b), infliximab, ribavirin, boceprevir, telaprevir, simeprevir, sofosbuvir, daclatasvir, elbasvir, grazoprevir, velpatasvir, lamivudine, adefovir dipivoxil, entecavir, telbivudine, tenofovir, clevudine, ANA380, zadaxin, CMX 157, ARB-1467, ARB-1740, ALN-HBV, BB-HB-331, Lunar-HBV, ARO-HBV, Myrcludex B, GLS4, NVR 3-778, AIC 649, JNJ56136379, ABI-H0731, AB-423, REP 2139, REP 2165, GSK3228836, GSK33389404, RNaseH Inhibitor, GS 4774, INO-1800, HB-110, TG1050, HepTcell, TomegaVax HBV, RG7795, SB9200, EYP001, CPI 431-32 and combinations thereof.

In one embodiment, the underlying cause responsible for liver fibrosis is excessive alcohol consumption and the at least one therapeutic agent is selected from the group consisting of topiramate, disulfiram, naltrexone, acamprosate and baclofen.

In one embodiment, the underlying cause responsible for liver fibrosis is a non-alcoholic fatty liver disease (NAFLD) and the at least one therapeutic agent is selected from the group consisting of telmisartan, orlistat, metformin, pioglitazone, atorvastatin, ezetimine, vitamin E, sylimarine, pentoxyfylline, ARBs, EPL, EPA-E, multistrain biotic (*L. rhamnosus, L. bulgaricus*), simtuzumab, obeticholic acid, elafibranor (GFT505), DUR-928, GR-MD, 02, aramchol, RG-125, cenicriviroc CVC and combinations thereof.

In one embodiment, the underlying cause responsible for liver fibrosis is a nonalcoholic steatohepatitis (NASH), preferably fibrotic NASH, and the at least one therapeutic agent is selected from the group consisting of insulin sensitizers (such as rosiglitazone, pioglitazone and MSDC-0602K); farnesoid X receptor (FXR) agonists (such as obeticholic acid (also referred to as OCA), GS-9674, LJN452, LMB763 and EDP-305); Peroxisome Proliferator-Activated Receptor a/6 (PPAR a/6) agonists (such as elafibranor, saroglitazar and IVA337); fibroblast growth factor 19 (FGF19) analogs (such as NGM282); fibroblast growth factor 21 (FGF21) analogs (such as PF-05231023); recombinant FGF21 (such as BMS-986036); stearoyl-coenzyme A desaturase 1 (SCD1) inhibitors (such as aramchol); apical sodium-dependent bile acid transporter (ASBT) inhibitors (such as volixibat); acetyl-coA carboxylase (ACC) inhibitors (such as GS-0976); glucagon-like peptide-1 (GLP-1) analogs (such as liraglutide, semaglutide exenatide and taspoglutide); ursodeoxycholic acid and norursodeoxycholic acid (NorUDCA); taurine; polyenephosphatidylcholine; thyroid hormone receptor (THR) β-agonists (such as MGL-3196); antioxidant agents (such as vitamin E and vitamin C); apoptosis signal-regulating kinase 1 (ASK1) inhibitors (such as GS-4997); DPP-4 inhibitors (such as sitagliptin, alogliptin, vildagliptin, saxagliptin, and linagliptin); vascular adhesion protein-1 (VAP-1) inhibitors (such as PXS-4728A); phosphodiesterase-4 (PDE-4) inhibitors; angiotensin II-1 type receptor antagonists (such as losartan and telmisartan); anti-inflammatory compounds (such as cenicriviroc, VLX-103 (oral pentamidine) and hyperimmune bovine clostrum); Toll-like receptor 4 antagonists (such as nalmefene); caspase inhibitors (such as emricasan); pentoxifylline; S-adenosyl-methionine; milk thistle; and probiotics.

Another object of the invention is at least one therapeutic agent for use in the treatment of liver fibrosis, including cirrhosis, in a subject, wherein the subject to be treated is identified as described hereinabove, and wherein the treatment is adapted to the subject as described hereinabove, depending on the severity of the liver fibrosis in said subject and/or on the underlying cause responsible for liver fibrosis in said subject.

Multi-targeted tests comprise performing several single-targeted tests (i.e., binary logistic regressions) and combining these complementary single-targeted tests. They are thus constructed to address several diagnostic targets, i.e., several fibrosis stages.

The main advantage of multi-targeted tests is the significant increase in their diagnostic performance, and in particular the significant increase in overall accuracy.

The multi-targeted combination derived from the multi-targeted test of the invention can also be used for assessing the risk of liver-related death of a subject, non liver related death of a subject or the risk of liver-related events, such as complications, in a subject.

In Example 1, the Applicant demonstrates that AUROC for cirrhosis of Multi-FibroMeters (MFMs$^{V2G}$) is significantly increased compared to corresponding FibroMeters. For cirrhosis diagnosis, the comparator of MFM is FibroMeter and not CirrhoMeter since FibroMeter was the previous reference for a multi-target diagnostic. In other words, when constructing the MFMs, the objective was that MFMs adds the diagnostic performance for cirrhosis of CirrhoMeter to FibroMeter. Considering all Metavir fibrosis stages, the performance, evaluated by Obuchowski index, is significantly increased for MFMs compared to most published mono-targeted tests (FibroMeter and CirrhoMeter) especially of third generation. Regarding fibrosis classification in multiple classes, a 92.3% accuracy was obtained with the new MFMs$^{V2G}$ test vs. 87.6% with the published FibroMeter$^{V2G}$ test as reference. This corresponds to a statistically significant 4.7% gain in correct classification which was sustained in the chronic hepatitis C validation population (4.4%). These gains were more marked with the MFMs$^{V3G}$ test: 5.9% and 7.1%, respectively. This accuracy gain was furthermore observed in other validation population representing different liver disease etiologies (chronic hepatitis B, HIV/chronic hepatitis C, nonalcoholic fatty liver disease, alcoholic liver disease).

Furthermore, the Applicant shows that when compared with other blood tests, the MFMs is significantly superior to all tests evaluated in chronic hepatitis C for cirrhosis diagnosis which is a new proper advantage (with regards to previous corresponding mono-targeted tests) versus APRT, Fibrotest, Zeng score and Hepascore (except with MFMs$^{V3G}$ but MFMs$^{V3G}$ remained advantageous since it acquired a significant gain in Obuchowski index vs. Hepascore). In other etiologies, MFMs is also significantly superior to all blood tests evaluated in chronic hepatitis C for cirrhosis diagnosis and/or Obuchowski index (except vs. Hepascore). This means a new advantage with respect to the comparison between Fibrotest and FibroMeter$^{V2G}$ and between Hepascore and FibroMeter$^{V3G}$. Indeed, FibroMeter$^{V3G}$ was significantly inferior to Hepascore and MFMs$^{V3G}$ became not significantly different from Hepascore.

Importantly, the construction of a multi-targeted diagnostic test, as illustrated in Example 1, can be applied to any non-invasive diagnostic test based on a semi-quantitative (ordinal) reference, e.g., a severity score in radiology.

In Example 2, the Applicant describes a 92.7% accuracy obtained with the new MFMc test vs. 87.6% with the published FibroMeter$^{V2G}$ test as reference. The 5.1% gain in correct classification corresponds to a 41.1% decrease in the 12.3% rate of misclassified patients with FibroMeter$^{V2G}$. This 5% accuracy gain is furthermore observed in three validation populations representing different liver disease etiologies (chronic hepatitis C, HIV/chronic hepatitis C, chronic hepatitis B).

Another advantage is that multi-targeting is an automated means to combine previously published complementary mono-targeted tests like FibroMeter$^{V2G}$ and CirrhoMeter$^{V2G}$. In this way, multi-targeting provides higher accuracy for important diagnostic targets like cirrhosis. Thus, MFMc is better adapted to the individual patient fibrosis stage.

Concerning cirrhosis diagnosis, the reference for non-invasive tests is liver elastometry, such as VCTE. The results presented in Example 1 show that VCTE is indeed superior to a cirrhosis-dedicated blood test (CirrhoMeter$^{V2G}$) with a significant difference over CirrhoMeter$^{V3G}$. MFMc eliminates this disadvantage, providing an accuracy superior, but not significantly, to that of VCTE in all etiologies evaluated.

When the main clinical diagnostic target is cirrhosis, it could be argued that a binary diagnosis with a single-targeted test using a single cut-off would be sufficient. However, using a binary diagnosis approach with a single cut-off has two main limits. First, VCTE (also known as Fibroscan), a reference for non-invasive diagnosis of cirrhosis, has a positive predictive value (PPV) for cirrhosis of only 57% in chronic hepatitis C (Cales P. et al. Cirrhosis Diagnosis and Liver Fibrosis Staging: Transient Elastometry Versus Cirrhosis Blood Test. J Clin Gastroenterol 2015; 49:512-519) with the usual cut-off of 14 kPa used by clinicians. The interest of the MFMc classification presented in the Examples is that it provides three categories of cirrhosis diagnosis: two firm classes for definitive cirrhosis (F4, positive predictive value (PPV) for cirrhosis of MFMc$^{V2G}$: 96%, result not shown) or early cirrhosis (F3/4, cirrhosis PPV: 67%) and a remaining class for doubtful cirrhosis (F3±1, cirrhosis PPV: 21%) where test results will need to be considered in the light of other available examinations such as VCTE or imaging and closer follow-up. The second limit to binary cirrhosis diagnosis is that non-cirrhosis results leave clinicians with great uncertainties. In particular, they cannot easily distinguish patients with severe fibrosis, who will require close follow-up or more active intervention, from patients without significant fibrosis. In that respect, a detailed and performant classification as can be obtained with the multi-targeted tests is far more informative.

In Example 2, the Applicant also demonstrates that the MFMc classification offers good prognostic discrimination, especially between four fibrosis classes: F2±1, F3±1, F3/4 and F4. The prognostic discrimination between the F3/4 and F4 classes is improved compared to FibroMeter$^{V2G}$. The MFMc classification is a simplified classification, with a maximum of two F stages per class. An exhaustive classification (up to three F per class) has the apparent advantage of better accuracy compared to a simplified classification (up to two F per class). However, the latter offers better precision and prognostication. Thus, a simplified classification seems sufficient for clinical practice. The lack of interest of an exhaustive classification can be attributed to the sources of misclassification by histological staging (sample size and observer reading). This is reinforced by the better prognostication by non-invasive tests than by histological staging (Naveau S. et al. Diagnostic and prognostic values of noninvasive biomarkers of fibrosis in patients with alcoholic liver disease. Hepatology 2009; 49:97-105). Finally, prognostication is significantly altered only by F2±1 or even F2/3 class, and thus the minimal classification can be described into four classes: F0/1 (non-significant fibrosis), F2/3 (significant fibrosis), F3/4 (early cirrhosis) and F4 (definitive cirrhosis).

EXAMPLES

Figure 1:
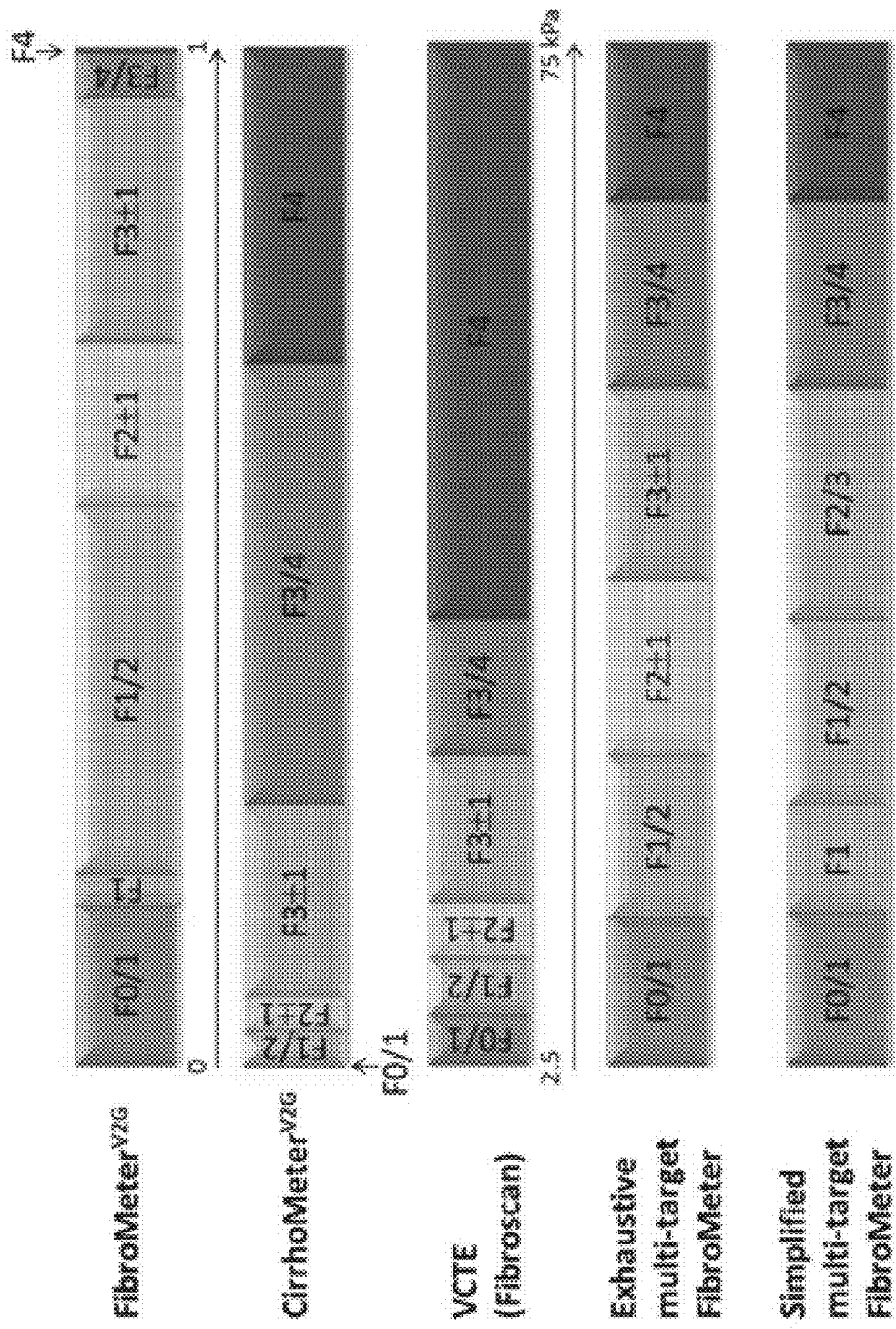
FIG. 1 is a diagram showing the fibrosis classifications of non-invasive tests. FibroMeter$^{V2G}$ and CirrhoMeter$^{V2G}$ are derived from corresponding test values ranging from 0 to 1. The VCTE scale ranges from 2.5 to 75 kPa. Multi-target FibroMeter (MFMc) classifications have schematic limits (i.e., without corresponding numerical scale) since they are not derived from a unique test score. Fibrosis classes are depicted by the corresponding Metavir F stage(s) within each rectangle.

The present invention is further illustrated by the following examples.

Example 1: Multi-Targeted FibroMeter Constructed for Multi-Target Score (MFMs)

Patients and Methods
Populations

A total of 2589 patients were initially included in the present study. The multi-target diagnostic test was developed using data from 1012 patients (derivation population), and an external validation was performed in 1577 patients (validation populations #1 to #5). Additional data were obtained with a validation population comprising 1220 patients suffering from chronic liver diseases with different etiologies (validation population #6). The overall population thus included 3809 patients.

Derivation Population

The derivation population included 1012 patients with CHC [4]. Thus, individual patient data were available from five centers, independent for study design, patient recruitment, blood marker determination and liver histology interpretation by an expert pathologist.

Validation Populations

Diagnostic populations—The validation population #1 included 641 patients with chronic hepatitis C (CHC) [5, 6]. The validation population #2 for chronic hepatitis B (CHB) was extracted from a previously published database [7] and included 152 patients all with chronic hepatitis (30.4% HBe Ag positive); inactive carriers of HBs Ag were excluded. The validation population #3 included 444 patients with CHC and (HIV) infection prospectively included from April 1997 to August 2007 if they had anti-HCV (hepatitis C virus) and anti-HIV (human immunodeficiency virus) antibodies, and HCV RNA in serum [8]. Population #4 comprised 225 patients with biopsy-proven nonalcoholic fatty liver disease (NAFLD) consecutively included in the study from January 2002 to March 2013 at Angers University Hospital and from September 2005 to July 2011 at Pessac University Hospital. NAFLD was defined as liver steatosis on liver biopsy after exclusion of concomitant steatosis-inducing drugs (such as corticosteroids, tamoxifen, amiodarone or methotrexate), excessive alcohol consumption (>210 g/week in men or >140 g/week in women), chronic hepatitis B or C infection, and histological evidence of other concomitant chronic liver disease (CLD). Patients were excluded if they had cirrhosis complications (ascites, variceal bleeding, systemic infection, or hepatocellular carcinoma). Population #5 included 115 patients with alcoholic liver disease (ALD) extracted from a database used in previously published works [9]. Population #6 included 1220 patients with different chronic liver disease (CLD) etiologies: CHC: 41.3%, NAFLD: 31.3%, alcohol, pure (ALD): 8.1% or mixed: 11.7%, CHB: 5.7%, co-infections (HIV/CHC, HIV/CHB, CHB/VHD, others): 1.2%, others combinations of previous etiologies: 0.7%. These patients were consecutively included between 2011 and 2016 in Angers and Pessac centers and represent a more recent population of clinical practice where liver biopsy is more often indicated when blood tests and VCTE are discordant. Therefore, this population was separately considered.

Diagnostic Methods
Histological Assessment

Liver biopsies were performed using Menghini's technique with a 1.4-1.6 mm diameter needle. Biopsy specimens were fixed in a formalin-alcohol-acetic solution and embedded in paraffin; 5 μm thick sections were then cut and stained with hematoxylin-eosin-saffron. Liver fibrosis was evaluated according to Metavir fibrosis (F) stages [10] by two senior experts with a consensus reading in case of discordance in Angers and in the Fibrostar study [11] (part of validation population #1), and by a senior expert in other centers. These liver specimen findings served as a reference for the liver fibrosis evaluation by non-invasive tests.

FibroMeter Variables

Biological markers were those previously used in blood tests carried out to diagnose different lesions in chronic viral hepatitis [9, 12]. The following biological markers were included: platelets, aspartate aminotransferase, hyaluronate, urea, prothrombin index, alpha2-macroglobulin as used in FibroMeter$^{V2G}$ [4, 9] plus gamma-glutamyl transpeptidase (GGT) used in FibroMeter$^{V3G}$ [12] and alanine aminotransferase used in InflaMeter targeted for liver activity [13]. Clinical markers were also included (age and sex as used in FibroMeter$^{V2G}$). Thus, 10 variables were available. The new tests were constructed by including hyaluronate (second generation as for FibroMeter$^{V2G}$) or not (third generation as for FibroMeter$^{V3G}$). Reference blood tests for comparison with the new test were FibroMeter$^{V2G}$ or FibroMeter$^{V3G}$, targeted for significant fibrosis (F≥2), and CirrhoMeter$^{V2G}$ or CirrhoMeter$^{V3G}$, targeted for cirrhosis, with previously calculated classifications [14, 15].

Non-Invasive Tests

A total of 19 variables (4 clinical markers and 15 biological markers) were used in 17 tests (14 blood tests, 1 elastometry technique and 2 combined). Eleven tests had been constructed in CHC populations and five in other CLD causes (two in NAFLD and one each in ALD, CHB or HIV-HCV).

Blood tests—Fibrotest [16], Hepascore [17], Fib-4 [18] and APRI [19] were calculated according to published or patented formulas. FibroMeter$^{V2G}$ [20], CirrhoMeter$^{V2G}$ [3], FibroMeter$^{V3G}$ [12] and CirrhoMeter$^{V3G}$ [12] were constructed for Metavir fibrosis staging in CHC. FibroMeter/CirrhoMeter$^{V2G}$ differs from FibroMeter/CirrhoMeter$^{V3G}$ in that the hyaluronate included in the former is replaced by GGT in the latter. CirrhoMeters were constructed for cirrhosis diagnosis and include all of the FibroMeter biomarkers [3]. The Zeng score was constructed in CHB [21]. FibroMeter$^{ALD2G}$ (second generation) [13] and FibroMeter$^{NAFLD}$ [22] were constructed for Metavir fibrosis staging respectively in ALD and NAFLD. NAFLD fibrosis score was constructed for NASH-CRN (or Kleiner) fibrosis staging in NAFLD [23]. This body of tests provided at least one test specific to each etiology. All blood assays were performed in the same laboratories of each center except for the Fibrostar study (part of population #1) where they were centralized. Tests were used as raw data with no correction rules (e.g., expert systems).

Liver elastometry—Vibration-controlled transient elastometry or VCTE (Fibroscan, Echosens, Paris, France) was performed by an experienced observer (>50 examinations before the study), blinded for patient data. Examination conditions were those recommended by the manufacturer [24]. VCTE examination was stopped when 10 valid measurements were recorded. Results (kPa) were expressed as the median and the interquartile range of all valid measurements.

Test Construction

The primary objective of the study was to construct multi-targeted FibroMeters displaying a significant increase in diagnostic performance when compared to mono-targeted tests of the FibroMeter family. In particular, the aim was to obtain a multi-targeted test with Obuchowski index and area under the receiver operating characteristics (AUROC) for cirrhosis significantly superior to those of FibroMeter, and with AUROC for cirrhosis superior or equal to that of CirrhoMeter.

The second objective of the study was to obtain multi-targeted FibroMeters displaying an improved diagnostic performance when compared to other fibrosis tests not belonging to the FibroMeter family, in particular Fibrotest, Hepascore, Zeng score and VCTE (also known as Fibroscan).

The construction of the multi-target classification system was performed in 3 successive steps.

Step 1: Single-target test construction—The single tests correspond to binary logistic regressions on the markers of the FibroMeter family of tests, in which said markers are combined as single markers, or as ratios of markers, or as arithmetic combinations of markers. These tests were built using a conventional binary logistic regression approach using as many diagnostic targets as possible by the five Metavir F stages. These targets were: fibrosis (F≥1), significant fibrosis (F≥2), severe fibrosis (F≥3), and cirrhosis (F=4). Four single-target tests were thus obtained. Six additional targets were obtained by binary targets using two cut-offs: e.g., F1 or F1+F2 or F1+F2+3 vs. other stages. The 6 additional targets were: F1 vs. F0+F2+F3+F4, F2 vs. F0+F1+F3+F4, F3 vs. F0+F1+F2+F4, F1+F2 vs. F0+F3+F4, F2+F3 vs. F0+F1+F4 and F1+F2+F3 vs. F0+F4. In total, ten single-target tests could thus be obtained.

Step 2: Single-target test selection—Previous mono-targeted tests were included in stepwise multiple linear regression targeted for the five Metavir stages. Metavir stages were normalized to 1, i.e., divided by 4, to obtain a score between 0 and 1. This new score was called multi-targeted FibroMeter (MFM).

Step 3: Multi-target test classification—Briefly, the correspondence between the previous MFM score and Metavir stages was derived according to the published method [20].

This optional step resulted in a classification including 6 fibrosis classes: 0/1 (corresponding to Metavir F0/1, 1/2 (F1/2), 2 (F2±1), 3 (F3±1), 3/4 (F3/4) and 4 (F4).

Statistics

Accuracy—The diagnostic accuracy of each test score was expressed with two descriptors. The main descriptor was the Obuchowski index (OI) [25] to better take into account differences in fibrosis stage prevalence between populations and thus limit spectrum bias. This index is a multinomial version of the AUROC adapted to ordinal references such as pathological fibrosis staging. With N (=5: F0 to F4) categories of the gold standard outcome and AUROCst, it estimates the AUROC of diagnostic tests differentiating between categories s and t. The OI is a weighted average of the N(N−1)/2 (=10) different AUROCst corresponding to all the pair-wise comparisons between two of the N categories. Additionally, the OI was assessed using a penalty function proportional to the difference in fibrosis stages, i.e., a penalty of 1 when the difference between stages was one, 2 when the difference was two, and so on. The reference prevalence was standardized according to the largest series of CHC with liver biopsies [26] to facilitate comparisons between etiologies. Thus, the result can be interpreted as the probability that the non-invasive test will correctly rank two randomly chosen patients with different fibrosis stages.

The second descriptor for the diagnostic accuracy of test score was the AUROC, i.e., the classical index for binary diagnostic targets.

The overall accuracy of classification tests was assessed by the rate of well-classified patients according to Metavir F.

Optimism bias—By definition, optimism bias maximizes performance in the population where tests are constructed: this affected FibroMeter, CirrhoMeter and MFM in the derivation population and VCTE in the validation population #1 for its fibrosis classification. Thus, external validation was performed outside these populations.

Sample size calculation—The size of the main populations (derivation and validation #1) was that necessary to detect a significant difference between two tests for the diagnosis of cirrhosis. With an a risk of 0.05, a β risk of 0.05, a cirrhosis prevalence of 0.12, an AUROC correlation of 0.82 and bilateral testing, the required sample size was 659 patients for the following expected AUROC values for cirrhosis: first test: 0.92, second test: 0.90 [3].

Miscellaneous—Quantitative variables were expressed as mean±standard deviation. Data were reported according to STARD [27] and Liver FibroSTARD statements [28], and analyzed on an intention to diagnose basis. The main statistical analyses were performed under the control of professional statisticians (SB, GH) using SPSS version 18.0 (IBM, Armonk, N.Y., USA) and SAS 9.2 (SAS Institute Inc., Cary, N.C., USA).

Results

Population Characteristics

The main characteristics of the studied populations are depicted in Table 2.

TABLE 2

Population characteristics.

| | | Validation | | | | | |
|---|---|---|---|---|---|---|---|
| Populations | Derivation | #1 | #2 | #3 | #4 | #5 | #6 |
| Etiology | CHC | CHC | CHB | HIV/CHC | NAFLD | Alcohol | Miscellaneous |
| Patients (n) | 1012 | 641 | 152 | 444 | 225 | 115 | 1220 |
| Male (%) | 59.6 | 60.5 | 81.5 | 68.7 | 65.3 | 64.3 | 67.3 |
| Age (years) | 45.4 ± 12.5 | 51.4 ± 11.2 | 40.0 ± 11.3 | 40.5 ± 5.8 | 56.5 ± 12.0 | 50.8 ± 23.9 | 50.7 ± 13.3 |
| Body mass index (kg/m$^2$) | NA | 24.8 ± 4.0 | NA | NA | 31.3 ± 5.0 | 23.9 ± 4.2 | 29.2 ± 6.3 |
| Metavir (%): | | | | | | | |
| F0 | 4.3 | 3.7 | 15.1 | 5.9 | 25.3 | 11.3 | 10.1 |
| F1 | 43.3 | 38.7 | 44.1 | 24.3 | 37.3 | 14.8 | 32.5 |
| F2 | 27.0 | 25.4 | 25.7 | 38.5 | 16.9 | 14.8 | 25.0 |
| F3 | 13.9 | 18.4 | 6.6 | 19.6 | 15.6 | 7.0 | 17.5 |
| F4 | 11.4 | 13.7 | 8.6 | 13.7 | 4.9 | 52.2 | 14.8 |
| Score | 1.85 ± 1.08 | 2.00 ± 1.13 | 1.49 ± 1.10 | 2.11 ± 1.10 | 1.37 ± 1.16 | 2.74 ± 1.49 | 1.94 ± 1.22 |
| Significant fibrosis (%) | 52.3 | 57.6 | 40.8 | 69.8 | 37.3 | 73.9 | 57.4 |
| Biopsy length (mm) | 21.2 ± 7.9 | 24.4 ± 8.7 | 21.6 ± 7.4 | 21 ± 10 | 30.8 ± 12.0 | NA | 27.6 ± 11.4 |

NA: not available

Diagnostic Performance

Derivation Population

Multi-FibroMeters were only compared to mono-targeted FibroMeters in this population of 1012 CHC since performance was optimized due to optimism bias for all these tests and not for others. Main diagnostic indices are reported in Table 3 (see below). These diagnostic indices were similar between Multi-FibroMeter$^{V2G}$ and FibroMeter$^{V2G}$ (diagnostic target: significant fibrosis) for significant fibrosis or CirrhoMeter$^{V2G}$ (diagnostic target: cirrhosis) for cirrhosis, especially accuracies were not significantly different (details not shown). AUROCs for all diagnostic targets and Obuchowski indexes are listed in Table 4 below. As expected, Multi-FibroMeter$^{V2G}$ ranked first for all diagnostic targets (Table 4). Pairwise comparisons are detailed in Table 5 below for cirrhosis AUROC since this is the main binary diagnostic target and for Obuchowski indexes in Table 6 below since this reflects overall performance. Cirrhosis AUROCs of Multi-FibroMeters were higher than FibroMeters and CirrhoMeters: this improvement was significant vs. FibroMeters but not vs. CirrhoMeters so the objective was reached. Obuchowski indexes of Multi-FibroMeters were significantly improved vs. FibroMeters (objective reached) and CirrhoMeters (beyond the objective).

TABLE 4

AUROCs for all diagnostic targets and Obuchowski indices for Metavir fibrosis (F) stages of multi-targeted FibroMeters vs. published mono-targeted FibroMeters in the CHC derivation population (1012 patients).

|  | AUROC | | | | Obuchowski index | |
| --- | --- | --- | --- | --- | --- | --- |
|  | F ≥ 1 | F ≥ 2 | F ≥ 3 | F = 4 | Value | Rank |
| FibroMeter$^{V2G}$ | 0.854 | 0.853 | 0.884 | 0.907 | 0.843 | 3 |
| CirrhoMeter$^{V2G}$ | 0.825 | 0.811 | 0.874 | 0.919 | 0.819 | 5 |
| Multi-FibroMeter$^{V2G}$ | 0.862 | 0.856 | 0.897 | 0.929 | 0.853 | 1 |
| FibroMeter$^{V3G}$ | 0.852 | 0.851 | 0.880 | 0.893 | 0.838 | 4 |
| CirrhoMeter$^{V3G}$ | 0.821 | 0.814 | 0.874 | 0.911 | 0.818 | 6 |
| Multi-FibroMeter$^{V3G}$ | 0.861 | 0.855 | 0.892 | 0.919 | 0.850 | 2 |

Best result per diagnostic target is indicated in bold.

TABLE 3

Diagnostic indices of blood tests for significant fibrosis or cirrhosis in the CHC derivation population (1012 patients). 95% confidence intervals in parentheses.

| Test | Cut-off$^a$ | Kappa index$^b$ | Sensitivity (%) | Specificity (%) | Predictive value % Positive | Predictive value % Negative | Likelihood ratio Positive | Likelihood ratio Negative | Diagnostic odds ratio | Accuracy (%) | AUROC$^c$ |
| --- | --- | --- | --- | --- | --- | --- | --- | --- | --- | --- | --- |
| Significant fibrosis: | | | | | | | | | | | |
| FibroMeter$^{V2G}$ | 0.4115 | 0.560 (0.507-0.609) | 80.4 (77.0-83.8) | 75.6 (71.7-79.4) | 78.3 (74.8-81.8) | 77.8 (74.1-81.6) | 3.29 | 0.26 | 12.7 (9.4-17.3) | 78.1 (75.5-80.6) | 0.853 (0.830-0.876) |
| Multi-FibroMeter$^{V2G}$ | 0.399 | 0.567 (0.515-0.616) | 81.9 (78.6-85.1) | 74.7 (70.9-78.6) | 78.0 (74.6-81.5) | 79.0 (75.3-82.7) | 3.24 | 0.24 | 13.3 (9.9-18.3) | 78.5 (75.9-81.0) | 0.85 (0.834-0.879) |
| Cirrhosis: | | | | | | | | | | | |
| CirrhoMeter$^{V2G}$ | 0.442 | 0.602 (0.502-0.684) | 54.8 (45.7-63.9) | 97.9 (96.9-98.8) | 76.8 (67.7-86.0) | 94.4 (92.9-95.9) | 25.86 | 0.46 | 56.0 (30.3-111.2) | 93.0 (91.4-94.6) | 0.919 (0.893-0.945) |
| Multi-FibroMeter$^{V2G}$ | 0.748 | 0.603 (0.527-0.680) | 60.0 (51.0-69.0) | 96.7 (95.5-97.8) | 69.7 (60.6-78.7) | 95.0 (93.5-96.4) | 17.94 | 0.41 | 43.4 (27.4-74.8) | 92.5 (90.9-94.1) | 0.929 (0.910-0.949) |

AUROC: area under the receiver operating characteristic.
$^a$Diagnostic cut-offs of blood tests were fixed a posteriori in this derivation population (maximum Youden index (= maximum accuracy) for significant fibrosis and maximum accuracy for cirrhosis).
$^b$Kappa index reflecting agreement with liver specimen (all p < 0.001).
$^c$AUROC is independent of diagnostic cut-off.

TABLE 5

Comparison of AUROCs for cirrhosis of multi-targeted FibroMeters and mono-targeted FibroMeters in the CHC derivation population (1012 patients in Table 3) by Delong test.

|  | FM$^{2G}$ | CM$^{2G}$ | MFMF$^{2G}$ | FM$^{3G}$ | CM$^{3G}$ | MFMF$^{3G}$ |
| --- | --- | --- | --- | --- | --- | --- |
| FibroMeter$^{V2G}$ | — | 0.2316 | 8.10$^{-6}$ | 0.0039 | 0.6764 | 0.0594 |
| CirrhoMeter$^{V2G}$ |  | — | 0.2419 | 0.0280 | 0.0978 | 0.9864 |
| Multi-FibroMeter$^{V2G}$ |  |  | — | 4.10$^{-8}$ | 0.0459 | 0.0342 |
| FibroMeter$^{V3G}$ |  |  |  | — | 0.0945 | 2.10$^{-6}$ |
| CirrhoMeter$^{V3G}$ |  |  |  |  | — | 0.3800 |
| Multi-FibroMeter$^{V3G}$ |  |  |  |  |  | — |

FM$^{2G}$: FibroMeter$^{V2G}$, CM$^{2G}$: CirrhoMeter$^{V2G}$, MFM$^{2G}$: multi-targeted FibroMeter$^{V2G}$, FM$^{3G}$: FibroMeter$^{V3G}$, CM$^{3G}$: CirrhoMeter$^{V3G}$, MFM$^{3G}$: multi-targeted FibroMeter$^{V3G}$
Significant differences are indicated in bold.

TABLE 6

Comparison of Obuchowski indices of multi-targeted FibroMeters and mono-targeted FibroMeters in the CHC derivation population (1012 patients in Table 3) by z test.

| | $FM^{2G}$ | $CM^{2G}$ | $MFMF^{2G}$ | $FM^{3G}$ | $CM^{3G}$ | $MFMF^{3G}$ |
|---|---|---|---|---|---|---|
| FibroMeter$^{v2G}$ | — | 0.0005 | 1.10$^{-5}$ | 0.0344 | 0.0003 | 0.0152 |
| CirrhoMeter$^{v2G}$ | | — | 4.10$^{-7}$ | 0.0068 | 0.6657 | 1.10$^{-5}$ |
| Multi-FibroMeter$^{v2G}$ | | | — | 2.10$^{-7}$ | 4.10$^{-7}$ | 0.0574 |
| FibroMeter$^{v3G}$ | | | | — | 0.0017 | 1.10$^{-6}$ |
| CirrhoMeter$^{v3G}$ | | | | | — | 3.10$^{-6}$ |
| Multi-FibroMeter$^{v3G}$ | | | | | | — |

$FM^{2G}$: FibroMeter$^{v2G}$, $CM^{2G}$: CirrhoMeter$^{v2G}$, $MFM^{2G}$: multi-targeted FibroMeter$^{v2G}$, $FM^{3G}$: FibroMeter$^{v3G}$, $CM^{3G}$: CirrhoMeter$^{v3G}$, $MFM^{3G}$: multi-targeted FibroMeter$^{v3G}$
Significant differences are indicated in bold.

CHC Validation Population

Multi-FibroMeters were compared to 10 other single tests in this population of 641 CHC where optimism bias was excluded (Table 7 below). Combined Elasto-FibroMeters were considered apart in this comparison due to optimism bias. Again, Multi-FibroMeter$^{v2G}$ ranked first for Obuchowski indexes.

TABLE 7

AUROCs for all diagnostic targets and Obuchowski indices for Metavir fibrosis (F) stages of all tests in the CHC validation population (641 patients). p values of pair comparisons are reported in Tables 8 and 9.

| | AUROC | | | | Obuchowski index | |
|---|---|---|---|---|---|---|
| | F ≥ 1 | F ≥ 2 | F ≥ 3 | F = 4 | Value | Rank |
| FibroMeter$^{v2G}$ | 0.827 | 0.812 | 0.830 | 0.863 | 0.797 | 2 |
| CirrhoMeter$^{v2G}$ | 0.783 | 0.785 | 0.816 | 0.858 | 0.770 | 5 |
| Multi-FibroMeter$^{v2G}$ | 0.822 | 0.808 | 0.838 | 0.880 | 0.798 | 1 |
| FibroMeter$^{v3G}$ | 0.819 | 0.798 | 0.816 | 0.844 | 0.785 | 4 |
| CirrhoMeter$^{v3G}$ | 0.769 | 0.771 | 0.796 | 0.840 | 0.756 | 7 |
| Multi-FibroMeter$^{v3G}$ | 0.818 | 0.804 | 0.826 | 0.868 | 0.792 | 3 |
| APRI | 0.769 | 0.751 | 0.768 | 0.814 | 0.742 | 10 |
| Fib4 | 0.757 | 0.762 | 0.773 | 0.802 | 0.741 | 11 |
| Fibrotest | 0.797 | 0.769 | 0.800 | 0.822 | 0.762 | 6 |
| Hepascore | 0.750 | 0.776 | 0.804 | 0.849 | 0.752 | 9 |
| Zeng score | 0.740 | 0.757 | 0.791 | 0.810 | 0.734 | 12 |
| VCTE | 0.704 | 0.788 | 0.839 | 0.897 | 0.754 | 8 |
| Elasto-FibroMeter$^{v2G}$ | 0.795 | 0.843 | 0.878 | 0.922 | 0.812 | ND [a] |
| Elasto-FibroMeter$^{v3G}$ | 0.795 | 0.842 | 0.877 | 0.922 | 0.812 | ND [a] |

VCTE: vibration controlled transient elastography (by Fibroscan).
[a] ND: not done due to optimism bias.

TABLE 8

Comparison of AUROCs for cirrhosis of all test pairs in the CHC validation population (641 patients, Table 7) by Delong test.

| | $FM^{2G}$ | $CM^{2G}$ | $MFMF^{2G}$ | $FM^{3G}$ | $CM^{3G}$ | $MFMF^{3G}$ | APRI | Fib4 | FT | HS | Zeng | VCTE | $EFM^{2G}$ | $EFM^{3G}$ |
|---|---|---|---|---|---|---|---|---|---|---|---|---|---|---|
| $FM^{2G}$ | — | 0.773 | 0.038 | 0.012 | 0.204 | 0.625 | 0.005 | 0.004 | 0.010 | 0.381 | 0.005 | 0.087 | <0.001 | <0.001 |
| $CM^{2G}$ | | — | 0.059 | 0.431 | 0.017 | 0.510 | 0.045 | 0.007 | 0.128 | 0.671 | 0.031 | 0.103 | <0.001 | <0.001 |
| $MFMF^{2G}$ | | | — | <0.001 | 0.003 | 0.081 | <0.001 | <0.001 | <0.001 | 0.025 | <0.001 | 0.380 | <0.001 | <0.001 |
| $FM^{3G}$ | | | | — | 0.824 | 0.004 | 0.102 | 0.031 | 0.148 | 0.779 | 0.097 | 0.017 | <0.001 | <0.001 |
| $CM^{3G}$ | | | | | — | 0.036 | 0 248 | 0.037 | 0.446 | 0.710 | 0.216 | 0.029 | <0.001 | <0.001 |
| $MFMF^{3G}$ | | | | | | — | 0.004 | <0.001 | 0.008 | 0.342 | 0.010 | 0.190 | <0.001 | <0.001 |
| APRI | | | | | | | — | 0.503 | 0.779 | 0.169 | 0.869 | <0.001 | <0.001 | <0.001 |
| Fib4 | | | | | | | | — | 0.504 | 0.110 | 0.782 | 0.001 | <0.001 | <0.001 |
| Fibrotest | | | | | | | | | — | 0.101 | 0.598 | 0.001 | <0.001 | <0.001 |

TABLE 8-continued

Comparison of AUROCs for cirrhosis of all test pairs in the CHC validation population (641 patients, Table 7) by Delong test.

| | $FM^{2G}$ | $CM^{2G}$ | $MFMF^{2G}$ | $FM^{3G}$ | $CM^{3G}$ | $MFMF^{3G}$ | APRI | Fib4 | FT | HS | Zeng | VCTE | $EFM^{2G}$ | $EFM^{3G}$ |
|---|---|---|---|---|---|---|---|---|---|---|---|---|---|---|
| Hepascore | | | | | | | | | | — | 0.016 | 0.019 | <0.001 | <0.001 |
| Zeng | | | | | | | | | | | — | <0.001 | <0.001 | <0.001 |
| VCTE | | | | | | | | | | | | — | 0.024 | 0.028 |
| $EFM^{2G\ a}$ | | | | | | | | | | | | | — | 0.856 |
| $EFM^{3G\ a}$ | | | | | | | | | | | | | | — |

$FM^{2G}$: FibroMeter$^{V2G}$, $CM^{2G}$: CirrhoMeter$^{V2G}$, $MFM^{2G}$: multi-targeted FibroMeter$^{V2G}$, $FM^{3G}$: FibroMeter$^{V3G}$, $CM^{3G}$: CirrhoMeter$^{V2G}$, $MFM^{3G}$: multi-targeted FibroMeterV$^{3G}$, FT: Fibrotest, HS: Hepascore, VCTE: vibration controlled transient elastography (by Fibroscan), $EFM^{2G}$: Elasto-FibroMeterV$^{2G}$, $EFM^{3G}$: Elasto-FibroMeterV$^{3G}$.
Significant differences are shown in bold.
[a] Optimism bias Pairwise comparisons for cirrhosis AUROCs are detailed in Table 8 hereinabove. AUROCs of Multi-FibroMeters were significantly improved vs. FibroMeters or CirrhoMeters (borderline significance between multi-FibroMeter$^{V2G}$ and CirrhoMeter$^{V2G}$) which was beyond the objective and reinforced the results observed in the derivation population. In addition, AUROCs of Multi-FibroMeters were significantly superior to all other single blood tests (except between Multi-FibroMeter$^{V3G}$ and Hepascore), but not vs. VCTE. Considering significant improvements brought by Multi-FibroMeters, it should be underlined that Multi-FibroMeter$^{V2G}$ had new advantages of significant superiority vs. Fibrotest (p<0.001) or Hepascore (p=0.025) which was not the case previously for CirrhoMeter$^{V2G}$ (p=0.128 or p=0.671, respectively). The new advantages were more marked for Multi-FibroMeter$^{V3G}$ since the differences became significant vs. APRI, Fibrotest and Zeng score whereas the AUROCs for cirrhosis of these last 3 tests were not significantly different with FibroMeter$^{V2G}$ and even CirrhoMeter$^{V3G}$. Concerning VCTE, AUROCs for cirrhosis of Multi-FibroMeter$^{V3G}$ became not significantly different from that of VCTE whereas this latter was significantly higher than those of FibroMeter$^{V3G}$ or CirrhoMeter$^{V3G}$. In other words, Multi-FibroMeter$^{V3}$G deleted the superiority of VCTE over its corresponding mono-targeted tests.

Pairwise comparisons for Obuchowski indexes are detailed in Table 9 below. Obuchowski indexes of Multi-FibroMeters were significantly improved vs. FibroMeters or CirrhoMeters (except between Multi-FibroMeter$^{V2G}$ and FibroMeter$^{V2G}$). Obuchowski indexes of Multi-FibroMeters were significantly higher than all those of other blood tests. This was a new advantage mainly between multi-FibroMeter$^{V3G}$ and Hepascore. There was also the occurrence of significant superiority of Multi-FibroMeters vs. all single blood tests at the difference of CirrhoMeters but this improvement had less clinical interest since CirrhoMeters are only used for cirrhosis diagnosis. Concerning comparison between Multi-FibroMeters and VCTE, the differences remained not significant as for FibroMeters or CirrhoMeters. Concerning comparison between Multi-FibroMeter$^{V3G}$ and Elasto-FibroMeters, despite an optimism bias favoring Elasto-FibroMeters, the differences became not significant contrary to FibroMeter$^{V3G}$ or CirrhoMeter$^{V3G}$. In other words, Multi-FibroMeter$^{V3G}$ deleted the superiority of Elasto-FibroMeters over corresponding mono-targeted blood tests.

TABLE 9

Comparison of Obuchowski indices of all test pairs in the CHC validation population (641 patients, Table 7) by z test.

| | $FM^{2G}$ | $CM^{2G}$ | $MFMF^{2G}$ | $FM^{3G}$ | $CM^{3G}$ | $MFMF^{3G}$ | APRI | Fib4 | FT | HS | Zeng | VCTE | $EFM^{2G}$ | $EFM^{3G}$ |
|---|---|---|---|---|---|---|---|---|---|---|---|---|---|---|
| $FM^{2G}$ | — | 0.003 | 0.995 | 0.002 | <0.001 | 0.237 | <0.001 | <0.001 | 0.002 | 0.004 | <0.001 | 0.096 | 0.244 | 0.241 |
| $CM^{2G}$ | | — | 0.004 | 0.148 | 0.003 | 0.032 | 0.146 | 0.073 | 0.562 | 0.306 | 0.081 | 0.576 | 0.012 | 0.011 |
| $MFMF^{2G}$ | | | — | <0.001 | <0.001 | 0.040 | 0.001 | <0.001 | 0.001 | 0.004 | <0.001 | 0.090 | 0.233 | 0.229 |
| $FM^{3G}$ | | | | — | 0.001 | 0.035 | 0.013 | 0.002 | 0.039 | 0.053 | 0.004 | 0.242 | 0.041 | 0.036 |
| $CM^{3G}$ | | | | | — | <0.001 | 0.494 | 0.336 | 0.660 | 0.853 | 0.322 | 0.962 | 0.001 | <0.001 |
| $MFMF^{3G}$ | | | | | | — | 0.004 | <0.001 | 0.008 | 0.022 | 0.002 | 0.158 | 0.118 | 0.109 |
| APRI | | | | | | | — | 0.958 | 0.312 | 0.678 | 0.719 | 0.678 | <0.001 | <0.001 |
| Fib4 | | | | | | | | — | 0.242 | 0.668 | 0.722 | 0.680 | <0.001 | <0.001 |
| Fibrotest | | | | | | | | | — | 0.487 | 0.117 | 0.747 | <0.001 | <0.001 |
| Hepascore | | | | | | | | | | — | 0.307 | 0.914 | <0.001 | <0.001 |
| Zeng | | | | | | | | | | | — | 0.393 | <0.001 | <0.001 |
| VCTE | | | | | | | | | | | | — | <0.001 | <0.001 |
| $EFM^{2G\ a}$ | | | | | | | | | | | | | — | 0.884 |
| $EFM^{3G\ a}$ | | | | | | | | | | | | | | — |

$FM^{2G}$: FibroMeter$^{V2G}$, $CM^{2G}$: CirrhoMeter$^{V2G}$, $MFM^{2G}$: multi-targeted FibroMeter$^{V2G}$, $FM^{3G}$: FibroMeter$^{V3G}$, $CM^{3G}$: CirrhoMeter$^{V2G}$, $MFM^{3G}$: multi-targeted FibroMeterV$^{3G}$, FT: Fibrotest, HS: Hepascore, VCTE: vibration controlled transient elastography (by Fibroscan), $EFM^{2G}$: Elasto-FibroMeter$^{V2G}$, $EFM^{3G}$: Elasto-FibroMeter$^{V3G}$.
Significant differences are shown in bold.
[a] Optimism bias Non-CHC Validation Populations AUROC for cirrhosis and Obuchowski indices were compared in 11 to 17 fibrosis tests in 4 other etiologies in Table 10 below. Multi-FibroMeters had higher Obuchowski indices than corresponding mono-targeted blood tests (except in ALD). As there was a few variations of diagnostic indices between all etiologies for most tests (i.e., no significant difference of Obuchowski indices compared to those of CHC validation population, results not shown), etiologies were pooled resulting in a non-CHC population of 935 patients in Table 11 below.

Pairwise comparisons for cirrhosis AUROCs are detailed in Table 12 below. AUROCs of Multi-FibroMeters were significantly improved vs. FibroMeters but not vs. CirrhoMeters which fitted with objectives. AUROCs of Multi-FibroMeters were significantly superior to several single blood tests: APRI, Fib4 and Fibrotest (except for multi-FibroMeter$^{V3G}$), this last difference being a new advantage of multi-FibroMeter$^{V2G}$ vs. FibroMeter$^{V2G}$. Considering Multi-FibroMeter$^{V3G}$, the significant inferiority observed between Hepascore and the corresponding FibroMeter$^{V3G}$ was deleted to become non-significant.

Pairwise comparisons for Obuchowski indexes are detailed in Table 13 below. Obuchowski indexes were significantly improved vs. FibroMeters or CirrhoMeters. Obuchowski indexes of Multi-FibroMeters were significantly superior to all other single blood tests (except with Hepascore). Other new (minor) advantages were the significant superiority of Multi-FibroMeter$^{V3G}$ over APRI, Fibrotest or Zeng score at the difference of CirrhoMeters.

Comparisons with the 3 tests including VCTE were performed in a subset of 376 patients (Table 14 below).

TABLE 10

AUROC for cirrhosis and Obuchowski indices of all tests in the CHB (n = 152), HIV/CHC (n = 444), NAFLD (n = 224) and ALD (n = 115) validation populations.

|  | CHB | | HIV/CHC | | NAFLD | | ALD | |
| --- | --- | --- | --- | --- | --- | --- | --- | --- |
|  | AUROC F = 4 | Obuchowski | AUROC F = 4 | Obuchowski | AUROC F = 4 | Obuchowski | AUROC F = 4 | Obuchowski |
| FibroMeter$^{V2G}$ | 0.918 | 0.789 | 0.785 | 0.760 | 0.836 | 0.773 | 0.903 | 0.758 |
| CirrhoMeter$^{V2G}$ | 0940 | 0.768 | 0.832 | 0.737 | 0.857 | 0.750 | 0.900 | 9.772 |
| Multi-FibroMeter$^{V2G}$ | 0.942 | 0.802 | 0.823 | 0.766 | 0.850 | 0.783 | 0.905 | 0.770 |
| FibroMeter$^{V3G}$ | 0.909 | 0.781 | 0.758 | 0.749 | 0.793 | 0.749 | 0.819 | 0.715 |
| CirrhoMeter$^{V3G}$ | 0.940 | 0.761 | 0.809 | 0.727 | 0.898 | 0.723 | 0.849 | 0,738 |
| Multi-FibroMeter$^{V3G}$ | 0.942 | 0.793 | 0.794 | 0.756 | 0.803 | 0.759 | 0.847 | 0.728 |
| APRI | 0.810 | 0.727 | 0.678 | 0.712 | 0.679 | 0.680 | 0.527 | 0.532 |
| Fib4 | 0.890 | 0.731 | 0.743 | 0.699 | 0.691 | 0.691 | 0.707 | 0.625 |
| Fibrotest | 0.887 | 0.767 | 0.793 | 0.733 | 0.697 | 0.670 | — | — |
| Hepascore | 0.912 | 0.781 | 0.819 | 0.723 | 0.920 | 0.780 | 0.920 | 0.780 |
| Zeng score | 0.921 | 0.783 | 0.790 | 0.711 | 0.920 | 0.785 | 0.871 | 0.772 |
| VCTE | 0.906 | 0.746 | — | — | 0.951 | 0.808 | — | — |
| Elasto-FibroMeter$^{V2G}$ | 0.951 | 0.815 | — | — | 0.960 | 0.846 | — | — |
| Elasto-FibroMeter$^{V3G}$ | 0.947 | 0.812 | — | — | 0.953 | 0.840 | — | — |
| FibroMeter$^{NAFLD}$ | — | — | — | — | 0.819 | 0.714 | — | — |
| NAFLD fibrosis score | — | — | — | — | 0.775 | 0.673 | — | — |
| FibroMeter$^{ALD2G}$ | 0.915 | 0.758 | 0.830 | 0.728 | 0.949 | 0.803 | 0.929 $^a$ | 0.794 $^a$ |

VCTE: vibration controlled transient elastography (by Fibroscan)
$^a$ Optimism bias

TABLE 11

AUROCs for all diagnostic targets and Obuchowski indices Metavir fibrosis (F) stages of 12 blood tests in the non-CHC validation populations (935 patients).

|  | AUROC | | | | Obuchowski index | |
| --- | --- | --- | --- | --- | --- | --- |
|  | F ≥ 1 | F ≥ 2 | F ≥ 3 | F = 4 | Value | Rank |
| FibroMeter$^{V2G}$ | 0.797 | 0.829 | 0.849 | 0.874 | 0.780 | 2 |
| CirrhoMeter$^{V2G}$ | 0.748 | 0.792 | 0.855 | 0.892 | 0.754 | 7 |
| Multi-FibroMeter$^{V2G}$ | 0.793 | 0.829 | 0.859 | 0.895 | 0.786 | 1 |
| FibroMeter$^{V3G}$ | 0.774 | 0.814 | 0.827 | 0.838 | 0.763 | 6 |
| CirrhoMeter$^{V3G}$ | 0.718 | 0.770 | 0.829 | 0.862 | 0.731 | 9 |
| Multi-FibroMeter$^{V3G}$ | 0.779 | 0.817 | 0.837 | 0.862 | 0.773 | 3 |
| APRI | 0.733 | 0.729 | 0.710 | 0.676 | 0.712 | 11 |
| Fib4 | 0.684 | 0.734 | 0.767 | 0.788 | 0.694 | 12 |
| Fibrotest | 0.731 | 0.764 | 0.763 | 0.809 | 0.729 | 10 |
| Hepascore | 0.789 | 0.819 | 0.849 | 0.902 | 0.772 | 4 |
| Zeng score | 0.738 | 0.789 | 0.829 | 0.876 | 0.741 | 8 |
| FibroMeter$^{ALD2G}$ | 0.769 | 0.817 | 0.872 | 0.912 | 0.771 | 5 |

TABLE 12

Comparison of AUROC for cirrhosis of 12 blood test pairs in the non-CHC validation populations (935 patients in Table 11) by z test.

|  | FM$^{2G}$ | CM$^{2G}$ | MFMF$^{2G}$ | FM$^{3G}$ | CM$^{3G}$ | MFMF$^{3G}$ | APRI | Fib4 | FT | HS | Zeng | FMA |
| --- | --- | --- | --- | --- | --- | --- | --- | --- | --- | --- | --- | --- |
| FM$^{2G}$ | — | 0.0008 | 7.10$^{-6}$ | 0.0015 | 0.8941 | 0.9017 | 1.10$^{-6}$ | 0.0004 | 0.1142 | 0.0868 | 0.8031 | 0.0140 |
| CM$^{2G}$ |  | — | 0.8683 | 0.0001 | 0.0022 | 0.0153 | 1.10$^{-7}$ | 2.10$^{-6}$ | 0.0079 | 0.7685 | 0.1311 | 0.5144 |

TABLE 12-continued

Comparison of AUROC for cirrhosis of 12 blood test pairs in the non-CHC validation populations (935 patients in Table 11) by z test.

| | $FM^{2G}$ | $CM^{2G}$ | $MFMF^{2G}$ | $FM^{3G}$ | $CM^{3G}$ | $MFMF^{3G}$ | APRI | Fib4 | FT | HS | Zeng | FMA |
|---|---|---|---|---|---|---|---|---|---|---|---|---|
| $MFMF^{2G}$ | | — | $1.10^{-7}$ | 0.0253 | 0.0005 | $2.10^{-9}$ | $4.10^{-7}$ | 0.0033 | 0.8201 | 0.0793 | 0.4726 |
| $FM^{3G}$ | | | — | 0.0492 | 0.0012 | 0.0002 | 0.0276 | 0.8840 | 0.0099 | 0.3337 | 0.0016 |
| $CM^{3G}$ | | | | — | 0.9363 | $2.10^{-5}$ | 0.0007 | 0.2013 | 0.2955 | 0.7893 | 0.0531 |
| $MFMF^{3G}$ | | | | | — | $3.10^{-7}$ | 0.0002 | 0.1475 | 0.2356 | 0.7913 | 0.0473 |
| APRI | | | | | | — | 0.0222 | 0.0035 | $1.10^{-6}$ | 0.0002 | $1.10^{-7}$ |
| Fib4 | | | | | | | — | 0.1938 | $9.10^{-5}$ | 0.0074 | $2.10^{-5}$ |
| Fibrotest | | | | | | | | — | 0.0088 | 0.2941 | 0.0076 |
| Hepascore | | | | | | | | | — | 0.0624 | 0.3011 |
| Zeng | | | | | | | | | | — | 0.0207 |
| FMA | | | | | | | | | | | — |

$FM^{2G}$: FibroMeter$^{V2G}$, $CM^{2G}$: CirrhoMeter$^{V2G}$, $MFM^{2G}$: multi-targeted FibroMeter$^{V2G}$, $FM^{3G}$: FibroMeter$^{V3G}$, $CM^{3G}$: CirrhoMeter$^{V3G}$, $MFM^{3G}$: multi-targeted FibroMeter$^{V3G}$, FT: Fibrotest, HS: Hepascore, FMA: FibroMeter$^{ALD2G}$. Significant differences are shown in bold.

TABLE 13

Comparison of Obuchowski indices of 12 blood test pairs in the non-CHC validation population (935 patients in Table 11) by z test.

| | $FM^{2G}$ | $CM^{2G}$ | $MFMF^{2G}$ | $FM^{3G}$ | $CM^{3G}$ | $MFMF^{3G}$ | APRI | Fib4 | FT | HS | Zeng | FMA |
|---|---|---|---|---|---|---|---|---|---|---|---|---|
| $FM^{2G}$ | — | $4.10^{-6}$ | 0.0250 | $8.10^{-8}$ | $2.10^{-11}$ | 0.0576 | $2.10^{-9}$ | $6.10^{-15}$ | $8.10^{-9}$ | 0.3588 | 0.0001 | 0.3211 |
| $CM^{2G}$ | | — | $2.10^{-7}$ | 0.1723 | $2.10^{-9}$ | 0.0040 | 0.0017 | $7.10^{-7}$ | 0.0304 | 0.094 | 0.3256 | 0.0360 |
| $MFMF^{2G}$ | | | — | $8.10^{-12}$ | $2.10^{-16}$ | $7.10^{-7}$ | $2.10^{-11}$ | 0 | $2.10^{-10}$ | 0.1430 | $7.10^{-6}$ | 0.1159 |
| $FM^{3G}$ | | | | — | $1.10^{-6}$ | 0.009 | $7.10^{-6}$ | $9.10^{-11}$ | $5.10^{-6}$ | 0.4128 | 0.0268 | 0.4538 |
| $CM^{3G}$ | | | | | — | $8.10^{-12}$ | 0.1495 | 0.0009 | 0.8425 | 0.0013 | 0.4686 | 0.0001 |
| $MFMF^{3G}$ | | | | | | — | $2.10^{-8}$ | $4.10^{-14}$ | $2.10^{-6}$ | 0.9348 | 0.0036 | 0.8732 |
| APRI | | | | | | | — | 0.0837 | 0.2373 | $5.10^{-6}$ | 0.0468 | 0.0001 |
| Fib4 | | | | | | | | — | 0.0132 | $2.10^{-7}$ | 0.0003 | $5.10^{-7}$ |
| Fibrotest | | | | | | | | | — | $1.10^{-6}$ | 0.2858 | 0.0012 |
| Hepascore | | | | | | | | | | — | 0.0036 | 0.9319 |
| Zeng | | | | | | | | | | | — | 0.0115 |
| FMA | | | | | | | | | | | | — |

$FM^{2G}$: FibroMeter$^{V2G}$, $CM^{2G}$: CirrhoMeter$^{V2G}$, $MFM^{2G}$: multi-targeted FibroMeter$^{V2G}$, $FM^{3G}$: FibroMeter$^{V3G}$, $CM^{3G}$: CirrhoMeter$^{V3G}$, $MFM^{3G}$: multi-targeted FibroMeter$^{V3G}$, FT: Fibrotest, HS: Hepascore, FMA: FibroMeter$^{ALD2G}$. Significant differences are shown in bold.

TABLE 14

AUROCs for all diagnostic targets and Obuchowski indices of blood tests (FibroMeter family), VCTE and FibroMeter + VCTE combined tests in the non-CHC validation populations (376 patients).

| | AUROC | | | | Obuchowski index | |
|---|---|---|---|---|---|---|
| | $F \geq 1$ | $F \geq 2$ | $F \geq 3$ | $F = 4$ | Value | Rank |
| FibroMeter$^{V2G}$ | 0.744 | 0.852 | 0.833 | 0.884 | 0.789 | 4 |
| CirrhoMeter$^{V2G}$ | 0.688 | 0.809 | 0.829 | 0.902 | 0.764 | 6 |
| Multi-FibroMeter$^{V2G}$ | 0.731 | 0.859 | 0.854 | 0.904 | 0.797 | 3 |
| FibroMeter$^{V3G}$ | 0.712 | 0.836 | 0.829 | 0.862 | 0.771 | 7 |
| CirrhoMeter$^{V3G}$ | 0.661 | 0.796 | 0.821 | 0.880 | 0.747 | 9 |
| Multi-FibroMeter$^{V3G}$ | 0.718 | 0.847 | 0.840 | 0.880 | 0.783 | 5 |
| VCTE | 0.705 | 0.794 | 0.861 | 0.880 | 0.766 | 8 |
| Elasto-FibroMeter$^{V2G}$ | 0.772 | 0.881 | 0.915 | 0.940 | 0.833 | 1 |
| Elasto-FibroMeter$^{V3G}$ | 0.765 | 0.878 | 0.913 | 0.935 | 0.829 | 2 |

Comparisons of the Multi-FibroMeters to VCTE were also performed in the combined validation populations #1 to #6 (1746 patients). AUROC for significant fibrosis (F≥2) and for cirrhosis (F=4), Obuchowski index and rate of correctly classified patients were compared. The Multi-FibroMeter$^{V2G}$ displayed the best results in terms of Obuchowski index (OI=0.777) and rate of correctly classified patients (83%). VCTE displayed an Obuchowski index of 0.755 and a rate of correctly classified patients of 80%. The Multi-FibroMeter$^{V3G}$ also displayed better results than VCTE in terms of Obuchowski index (OI=0.759) and rate of correctly classified patients (82.7%). AUROC for significant fibrosis (F≥2) was 0.786 for VCTE vs. 0.817 for MFM$^{V2G}$ and 0.804 for MFM$^{V3G}$. AUROC for cirrhosis (F=4) were equivalent between the MFM$^{V2G}$ (0.885) or MFM$^{V3G}$ (0.860) and VCTE (0.898).

Overall Population

As shown in Table 15 below, the diagnostic performance of the Multi-FibroMeters was also evaluated in the overall population (3809 patients) since there was no optimism bias in statistical comparisons within the FibroMeter family. The MFM$^{V2G}$ displayed the best results in terms of AUROC for significant fibrosis, AUROC for severe fibrosis, AUROC for cirrhosis, and Obuchowski index. The MFM$^{V2G}$ also displayed a very high rate of correctly classified patients, only second to that of the MFM$^{V3G}$.

TABLE 15

Diagnostic performance in the overall population (3809 patients).

| | AUROC | | | | Obuchowski index | | Classification | |
|---|---|---|---|---|---|---|---|---|
| | $F \geq 1$ | $F \geq 2$ | $F \geq 3$ | $F = 4$ | Value | Rank | Rate | Rank |
| FibroMeter$^{V2G}$ | 0.788 | 0.832 | 0.849 | 0.878 | 0.791 | 2 | 82.1 | 3 |
| CirrhoMeter$^{V2G}$ | 0.747 | 0.800 | 0.846 | 0.897 | 0.769 | 5 | 81.8 | 4 |
| Multi-FibroMeter$^{V2G}$ | 0.778 | 0.833 | 0.863 | 0.906 | 0.795 | 1 | 86.0 | 2 |
| FibroMeter$^{V3G}$ | 0.767 | 0.823 | 0.837 | 0.855 | 0.776 | 4 | 79.5 | 6 |
| CirrhoMeter$^{V3G}$ | 0.722 | 0.790 | 0.835 | 0.879 | 0.754 | 6 | 80.8 | 5 |
| Multi-FibroMeter$^{V3G}$ | 0.764 | 0.823 | 0.849 | 0.886 | 0.782 | 3 | 86.1 | 1 |

The best result per diagnostic target is indicated in bold.

Fibrosis Staging

Classifications of FibroMeters [20], CirrhoMeters [15] and Multi-FibroMeters included 6 to 7 fibrosis classes reflecting Metavir staging. The new classes developed for Multi-FibroMeters were: F0/1, F1/2, F2±1, F3±1, F3/4 and F4. The rate of correctly classified patients ranked in the same order for the 6 tests as a function of the 3 populations: the derivation population (1012 CHC patients), the validation population #1 (676 CHC patients) and the combined validation populations #2 to #5 (936 non-CHC patients) (Table 16 below). These rates were significantly higher (p<0.001) in Multi-FibroMeters vs. corresponding FibroMeter$^{V2/3G}$ or CirrhoMeter$^{V2/3G}$ in the 3 populations. These rates were not significantly different between both Multi-FibroMeters$^{V2/3G}$.

Figure 4:
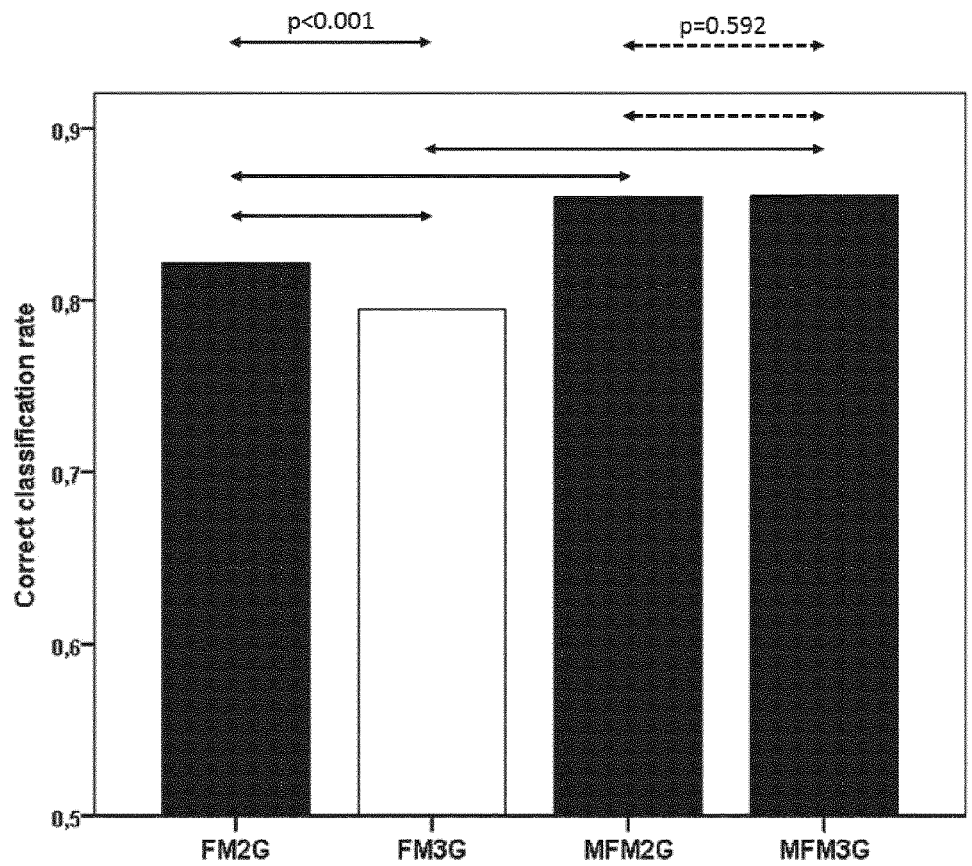
FIG. 4 is a graph showing the rate of correctly classified patients obtained with FibroMeter$^{V2G}$ (FM2G), FibroMeter$^{V3G}$ (FM3G), Multi-FibroMeter$^{V2G}$ (MFM2G) and Multi-FibroMeter$^{V3G}$ (MFM3G) in the overall population of 3809 patients. The arrows indicate the p value associated with the pairwise comparisons of the rate of correctly classified patients. Solid lines indicate a significant difference whereas dashed lines indicate a non-significant difference.

As shown in FIG. 4, similar results were obtained in the overall population (3809 patients), with the rates of correctly classified patients significantly higher (p<0.001) in Multi-FibroMeters vs. corresponding FibroMeter$^{V2/3G}$ or CirrhoMeter$^{V2/3G}$, but not significantly different between both Multi-FibroMeters$^{V2/3G}$.

Advantages of the Multi-Targeted FibroMeter (MFMs)

The primary objective of the study was to construct multi-targeted FibroMeters displaying a significant increase in diagnostic performance when compared to mono-targeted tests of the FibroMeter family. The accuracy between Multi-FibroMeters and FibroMeters or CirrhoMeters was thus compared through the assessment of five judgement criteria: 1) whether the AUROC for cirrhosis of the MFM was superior to that of the FibroMeter, 2) whether the Obuchowski index of the MFM was superior to that of the FibroMeter, 3) whether the AUROC for significant fibrosis of the MFM was equal or superior to that of the FibroMeter, 4) whether the rate of correctly classified patients (also called "classification metric") of the MFM was superior to that of the FibroMeter, and 5) whether the AUROC for cirrhosis of the MFM was equal or superior to that of the CirrhoMeter.

The second objective of the study was to construct multi-targeted FibroMeters, as obtained for the primary objective, displaying an improved diagnostic performance when compared to other fibrosis tests not belonging to the FibroMeter family, in particular Fibrotest, Hepascore, Zeng score and VCTE. The accuracy between Multi-FibroMeters and said fibrosis tests was thus compared through the assessment of three, in some cases four, judgement criteria: 1) whether the AUROC for cirrhosis of the MFM was superior to that of Fibrotest, Hepascore, and Zeng score; and equivalent to that of VCTE, 2) whether the Obuchowski index of the MFM was superior to that of the other fibrosis tests, 3) whether the AUROC for significant fibrosis of the MFM was superior to that of the other fibrosis tests, and 4) whether the rate of correctly classified patients (also called "classification metric") of the MFM was superior to that of the Fibrotest and of VCTE.

Table 17 below presents a summary of the diagnostic performance of both MFM$^{V2G}$ and MFM$^{V3G}$ when assessed

TABLE 16

Rate of correctly classified patients by fibrosis stagings of multi-targeted FibroMeters vs. published mono-targeted FibroMeters in the 3 main populations.

| | CHC derivation (1012 patients) | | | | | | | CHC validation (676 patients) $^a$ | | Non-CHC validation (935 patient) | |
|---|---|---|---|---|---|---|---|---|---|---|---|
| | F0 | F1 | F2 | F3 | F4 | All F | Rank | All F | Rank | All F | Rmk |
| FibroMete$^{V2G}$ | 56.8 | 92.2 | 88.9 | 80.0 | 87.7 | 81.6 | 3 | 83.6 | 3 | 77.9 | 3 |
| CirrhoMetet$^{V2G}$ | 43.2 | 89.7 | 91.1 | 82.9 | 93.0 | 81.5 | 4 | 82.5 | 4 | 76.3 | 4 |
| Multi-FibroMeter$^{V2G}$ | 50.0 | 92.9 | 96.3 | 97.9 | 90.4 | 92.3 $^b$ | 2 | 88.0 $^b$ | 2 | 81.3 $^b$ | 2 |
| FibroMeter$^{V3G}$ | 43.2 | 91.3 | 94.1 | 83.6 | 73.7 | 86.9 | 6 | 81.4 | 5 | 69.4 | 6 |
| CirrhoMeter$^{V3G}$ | 45.5 | 95.0 | 90.0 | 77.1 | 79.8 | 87.3 | 5 | 81.1 | 6 | 75.7 | 5 |
| Multi-FibroMeter$^{V3G}$ | 50.0 | 94.1 | 97.8 | 97.1 | 87.7 | 92.8 $^{b\,c}$ | 1 | 88.5 $^{b\,c}$ | 1 | 81.4 $^{b\,c}$ | 1 |
| p $^d$ | 0.266 | <0.001 | <0.001 | <0.001 | <0.001 | <0.001 | — | <0.001 | — | <0.001 | — |

Best result per diagnostic target is indicated in bold.
$^a$ more patients were available with these 6 tests than in the core population
$^b$ p < 0.001 vs. corresponding FibroMeter$^{v2/3G}$ or CirrhoMeter$^{v2/3G}$ by paired Wilcoxon test
$^c$ vs. Multi-FibroMeter$^{v2G}$ by paired Wilcoxon test: p = 0.443 in CHC derivation, p = 0.439 in CHC validation, p = 1 in non-CHC validation populations
$^d$ by paired Cochran test as described above, through comparison with mono-targeted tests of the FibroMeter family and with Fibrotest, Hepascore, Zeng score and VCTE.

TABLE 17

Diagnostic performance of Multi-FibroMeters when compared to the indicated tests in combined populations of maximum size[a].

| Judgment criteria | Test compared | Criteria fulfilled by Multi-FibroMeter | |
|---|---|---|---|
| | | V2G | V3G |
| Primary objective: | | | |
| AUROC cirrhosis > | FibroMeter | Yes | Yes |
| Obuchowski index > | | Yes [b] | Yes |
| AUROC significant F ≥ | | Yes | Yes |
| Classification metric > | | Yes | Yes |
| AUROC cirrhosis ≥ | CirrhoMeter | Yes | Yes [b] |
| Secondary objectives: | | | |
| AUROC cirrhosis > | Fibrotest | Yes | Yes |
| Obuchowski index > | | Yes | Yes |
| AUROC significant F > | | Yes | Yes |
| Classification metric > | | Yes | Yes |
| AUROC cirrhosis > | Hepascore | Yes | No [c] |
| Obuchowski index > | | Yes | No [c] |
| AUROC significant F > | | Yes | Yes |
| AUROC cirrhosis > | Zeng score | Yes | No [c] |
| Obuchowski index > | | Yes | Yes |
| AUROC significant F > | | Yes | Yes |
| AUROC cirrhosis ≈ | VCTE | Yes | No [d] |
| Obuchowski index > | | Yes | No [c] |
| AUROC significant F > | | Yes | No [c] |
| Classification metric > | | Yes | Yes |

VCTE: vibration controlled transient elastography (by Fibroscan), F: fibrosis. Results indicated in bold depict a significant difference. Results indicated in italics depict a statistical advantage of the Multi-FibroMeter over the test compared, in comparison with the FibroMeter or CirrhoMeter compared to the same test.
[a] Combined population: overall population for primary objective (3809 patients) and combination of populations #1 to #6 for secondary objectives (2796 patients except for Fibrotest: 1461 patients and VCTE: 1746 patients) to avoid optimism bias in comparisons. "Yes" and "no" indicate whether the criterion was reached or not with the following precision:
[b] Borderline significance
[c] Non-significant superior value of Multi-FibroMeter
[d] Significant inferior value of Multi-FibroMeter The primary objective was fulfilled, with both $MFM^{V2G}$ and $MFM^{V3G}$ displaying a significant increase in diagnostic performance when compared to the corresponding FibroMeter. Thus, all of five judgement criteria were positively met by the Multi-FibroMeters. In particular, AUROCs for cirrhosis of Multi-FibroMeters were significantly increased when compared to the corresponding FibroMeter. It should be noted that for cirrhosis diagnosis the most relevant comparator of Multi-FibroMeter is FibroMeter and not CirrhoMeter since FibroMeter (like other blood tests) is the classical test used whatever the target diagnostic. In other words, the objective was that Multi-FibroMeters added the diagnostic performance for cirrhosis of CirrhoMeter to FibroMeter. Considering discrimination of Metavir fibrosis stages, the performance of Multi-FibroMeters, evaluated by Obuchowski index, was significantly increased compared to FibroMeter. Regarding fibrosis classification reflecting Metavir stages, i.e., the rate of correctly classified patients, Multi-FibroMeters had significantly higher accuracy than FibroMeters.

Concerning the secondary objective, the judgement criteria were all positively met by the $MFM^{V2G}$ when compared to the other fibrosis tests, and only partially met by the $MFM^{V3G}$. It should be noted that the usual reference for non-invasive diagnosis of cirrhosis is VCTE. The results showed that AUROC for cirrhosis of VCTE and Multi-FibroMeter$^{V2G}$ were equivalent. AUROC for significant fibrosis and Obuchowski index were significantly increased in Multi-FibroMeter$^{V2G}$. This last result was confirmed by the rate of correctly classified patients.

In conclusion, using multi-targeted FibroMeters significantly improves the fibrosis staging accuracy compared to classical single-target blood tests or VCTE (also known as Fibroscan), especially when the underlying cause of the liver lesion is chronic hepatitis C.

For the diagnosis of cirrhosis, Multi-targeted FibroMeters are even matching VCTE, usually considered as the reference for non-invasive diagnosis of cirrhosis.

With the use of a single non-invasive test, the multi-targeted FibroMeter, it is thus now possible to accurately diagnose either significant fibrosis or cirrhosis. Multi-targeted FibroMeters thus provide unique non-invasive tests for the accurate diagnostic of the presence and severity of fibrosis, including cirrhosis.

Importantly, the present diagnostic method, i.e., the construction of a multi-targeted diagnostic test, can be applied to any non-invasive diagnostic test based on a semi-quantitative (ordinal) reference, e.g., a severity score in radiology.

REFERENCES

1 Oberti F, Valsesia E, Pilette C, Rousselet M C, Bedossa P, Aube C, et al. Noninvasive diagnosis of hepatic fibrosis or cirrhosis. Gastroenterology 1997; 113:1609-1616.
2 Chou R, Wasson N. Blood tests to diagnose fibrosis or cirrhosis in patients with chronic hepatitis C virus infection: a systematic review. Annals of internal medicine 2013; 158:807-820.
3 Boursier J, Bacq Y, Halfon P, Leroy V, de Ledinghen V, de Muret A, et al. Improved diagnostic accuracy of blood tests for severe fibrosis and cirrhosis in chronic hepatitis C. Eur J Gastroenterol Hepatol 2009; 21:28-38.
4 Cales P, de Ledinghen V, Halfon P, Bacq Y, Leroy V, Boursier J, et al. Evaluating the accuracy and increasing the reliable diagnosis rate of blood tests for liver fibrosis in chronic hepatitis C. Liver Int 2008; 28:1352-1362.
5 Boursier J, de Ledinghen V, Zarski J P, Fouchard-Hubert I, Gallois Y, Oberti F, et al. Comparison of eight diagnostic algorithms for liver fibrosis in hepatitis C: new algorithms are more precise and entirely noninvasive. Hepatology 2012; 55:58-67.
6 Boursier J, de Ledinghen V, Zarski J P, Rousselet M C, Sturm N, Foucher J, et al. A new combination of blood test and fibroscan for accurate non-invasive diagnosis of liver fibrosis stages in chronic hepatitis C. Am J Gastroenterol 2011; 106:1255-1263.
7 Leroy V, Sturm N, Faure P, Trocme C, Marlu A, Hilleret M N, et al. Prospective evaluation of FibroTest®, FibroMeter®, and HepaScore® for staging liver fibrosis in chronic hepatitis B: comparison with hepatitis C. J Hepatol 2014; 61:28-34.
8 Calès P, Halfon P, Batisse D, Carrat F, Perré P, Penaranda G, et al. Comparison of liver fibrosis blood tests developed for HCV with new specific tests in HIV/HCV co-infection J Hepatol 2010; 52:238-244.
9 Cales P, Oberti F, Michalak S, Hubert-Fouchard I, Rousselet M C, Konate A, et al. A novel panel of blood markers to assess the degree of liver fibrosis. Hepatology 2005; 42:1373-1381.

10 Intraobserver and interobserver variations in liver biopsy interpretation in patients with chronic hepatitis C. The French METAVIR Cooperative Study Group. Hepatology 1994; 20:15-20.

11 Zarski J P, Sturm N, Guechot J, Paris A, Zafrani E S, Asselah T, et al. Comparison of nine blood tests and transient elastography for liver fibrosis in chronic hepatitis C: The ANRS HCEP-23 study. J Hepatol 2012; 56:55-62.

12 Cales P, Boursier J, Bertrais S, Oberti F, Gallois Y, Fouchard-Hubert I, et al. Optimization and robustness of blood tests for liver fibrosis and cirrhosis. Clin Biochem 2010; 43:1315-1322.

13 Cales P, Boursier J, Oberti F, Hubert I, Gallois Y, Rousselet M C, et al. FibroMeters: a family of blood tests for liver fibrosis. Gastroenterol Clin Biol 2008; 32:40-51.

14 Boursier J, Bertrais S, Oberti F, Gallois Y, Fouchard-Hubert I, Rousselet M C, et al. Comparison of accuracy of fibrosis degree classifications by liver biopsy and non-invasive tests in chronic hepatitis C. BMC Gastroenterol 2011; 11:132.

15 Cales P, Boursier J, Oberti F, Bardou D, Zarski J P, de Ledinghen V. Cirrhosis Diagnosis and Liver Fibrosis Staging: Transient Elastometry Versus Cirrhosis Blood Test. J Clin Gastroenterol 2015; 49:512-519.

16 Castera L, Vergniol J, Foucher J, Le Bail B, Chanteloup E, Haaser M, et al. Prospective comparison of transient elastography, Fibrotest, APRI, and liver biopsy for the assessment of fibrosis in chronic hepatitis C. Gastroenterology 2005; 128:343-350.

17 Adams L A, Bulsara M, Rossi E, DeBoer B, Speers D, George J, et al. Hepascore: an accurate validated predictor of liver fibrosis in chronic hepatitis C infection. Clin Chem 2005; 51:1867-1873.

18 Sterling R K, Lissen E, Clumeck N, Sola R, Correa M C, Montaner J, et al. Development of a simple noninvasive index to predict significant fibrosis in patients with HIV/HCV coinfection. Hepatology 2006; 43:1317-1325.

19 Wai C T, Greenson J K, Fontana R J, Kalbfleisch J D, Marrero J A, Conjeevaram H S, et al. A simple noninvasive index can predict both significant fibrosis and cirrhosis in patients with chronic hepatitis C. Hepatology 2003; 38:518-526.

20 Leroy V, Halfon P, Bacq Y, Boursier J, Rousselet M C, Bourliere M, et al. Diagnostic accuracy, reproducibility and robustness of fibrosis blood tests in chronic hepatitis C: a meta-analysis with individual data. Clin Biochem 2008; 41:1368-1376.

21 Zeng M D, Lu L G, Mao Y M, Qiu D K, Li J Q, Wan M B, et al. Prediction of significant fibrosis in HBeAg-positive patients with chronic hepatitis B by a noninvasive model. Hepatology 2005; 42:1437-1445.

22 Cales P, Laine F, Boursier J, Deugnier Y, Moal V, Oberti F, et al., Comparison of blood tests for liver fibrosis specific or not to NAFLD. J Hepatol 2009; 50:165-173.

23 Angulo P, Hui J M, Marchesini G, Bugianesi E, George J, Farrell G C, et al. The NAFLD fibrosis score: a noninvasive system that identifies liver fibrosis in patients with NAFLD. Hepatology 2007; 45:846-854.

24 Castera L, Forns X, Alberti A. Non-invasive evaluation of liver fibrosis using transient elastography. J Hepatol 2008; 48:835-847.

25 Lambert J, Halfon P, Penaranda G, Bedossa P, Cacoub P, Carrat F. How to measure the diagnostic accuracy of noninvasive liver fibrosis indices: the area under the ROC curve revisited. Clin Chem 2008; 54:1372-1378.

26 Thein H H, Yi Q, Dore G J, Krahn M D. Estimation of stage-specific fibrosis progression rates in chronic hepatitis C virus infection: a meta-analysis and meta-regression. Hepatology 2008; 48:418-431.

27 Bossuyt P M, Reitsma J B, Bruns D E, Gatsonis C A, Glasziou P P, Irwig L M, et al., The STARD statement for reporting studies of diagnostic accuracy: explanation and elaboration. Clin Chem 2003; 49:7-18.

28 Boursier J, de Ledinghen V, Poynard T, Guechot J, Carrat F, Leroy V, et al., An extension of STARD statements for reporting diagnostic accuracy studies on liver fibrosis tests: The Liver-FibroSTARD standards. J Hepatol 2014.

29 Cales P, Boursier J, Ducancelle A, Oberti F, Hubert I, Hunault G, et al., Improved fibrosis staging by elastometry and blood test in chronic hepatitis C. Liver Int 2014; 34:907-917.

30 Boursier J, Zarski J P, de Ledinghen V, Rousselet M C, Sturm N, Lebail B, et al., Determination of reliability criteria for liver stiffness evaluation by transient elastography. Hepatology 2013; 57:1182-1191.

Example 2: Multi-Targeted FibroMeter Constructed for Multi-Target Classification (MFMc)

Patients and Methods

Populations

A total of 3901 patients were included in the present study: the multi-target diagnostic algorithm was developed using data from 1012 patients (derivation population), and an external validation was performed in 1330 patients (validation populations #1, #2 and #3). The prognostic relevance of the fibrosis classification resulting from this new diagnostic system was also assessed in a prospective cohort of 1559 patients (validation population #4).

Derivation Population

The derivation population included 1012 patients with chronic hepatitis C (CHC) (5). Thus, individual patient data were available from five centers, independent for study design, patient recruitment, biological marker determination and liver histology interpretation by an expert pathologist.

Validation Populations

Diagnostic populations—The validation population #1 included 676 patients with CHC (6, 7). The validation population #2 included 450 patients with CHC and HIV infection prospectively included from April 1997 to August 2007 if they had anti-HCV (hepatitis C virus) and anti-HIV (human immunodeficiency virus) antibodies, and HCV RNA in serum (8). The validation population #3 for chronic hepatitis B (CHB) was extracted from a previously published database (9) and included 204 patients all with chronic hepatitis (30.4% HBe Ag positive); inactive carriers of HBs Ag were excluded.

Prognostic population—All subjects over 18 years of age who were received for consultation or hospitalized for a chronic liver disease in the Department of Hepatology at the University Hospital of Angers from January 2005 to December 2009 were invited to join a study cohort (validation population #4), whatever the severity or etiology of their disease (viral hepatitis, alcoholic liver disease, non-alcoholic fatty liver disease (NAFLD), other causes). The resulting 1559 patients were then followed until death, liver transplantation or Jan. 1, 2011. The study was approved by an Institutional Review Board (AC-2012-1507) and informed consent was obtained from all patients.

Diagnostic Methods

Histological Assessment

Liver biopsies were performed using Menghini's technique with a 1.4-1.6 mm diameter needle. Biopsy specimens were fixed in a formalin-alcohol-acetic solution and embedded in paraffin; 5 μm thick sections were then cut and stained with hematoxylin-eosin-saffron. Liver fibrosis was evaluated according to Metavir fibrosis (F) stages (10) by two senior experts with a consensus reading in case of discordance in Angers and in the Fibrostar study (11) (part of validation population #1), and by a senior expert in other centers. The area of porto-septal fibrosis was centrally measured by automated morphometry as recently described (12) in the validation population #1.

FibroMeter Variables

Biological markers were those previously used in various blood tests carried out to diagnose different lesions in chronic viral hepatitis (13, 14). The following biological markers were included: platelets, aspartate aminotransferase (AST), hyaluronate, urea, prothrombin index, alpha2-macroglobulin as used in FibroMeter$^{V2G}$ (5, 13) plus gamma-glutamyl transpeptidase (GGT) (used in FibroMeter$^{V3G}$ (14) and QuantiMeterV targeted for area of fibrosis (13)), bilirubin (used in QuantiMeterV) and alanine aminotransferase (ALT) (used in InflaMeter targeted for liver activity (15)). Clinical markers were also included (age and sex as used in FibroMeter$^{V2G}$). Thus, with the addition of the AST/ALT ratio, 12 variables were available. Reference blood tests for comparison with the new test were FibroMeter$^{V2G}$, targeted for significant fibrosis (F≥2), and CirrhoMeter$^{V2G}$, targeted for cirrhosis, with previously calculated classifications (FIG. 1) (3, 4).

Liver Elastometry

Vibration-controlled transient elastometry or (Fibroscan, Echosens, Paris, France) was performed by an experienced observer (>50 examinations before the study), blinded for patient data. Examination conditions were those recommended by the manufacturer (16). VCTE examination was stopped when 10 valid measurements were recorded. Results (kPa) were expressed as the median and the interquartile range (IQR) of all valid measurements. The 6-class fibrosis classification recently developed in CHC was used here for VCTE (FIG. 1) (4).

Test Construction

The construction of the multi-target classification system was performed in four progressive steps, summarized in FIG. 2. The statistical details are provided in the supplemental material.

Step 1: Single-target test construction—These tests were built using a conventional binary logistic regression (BLR) approach, using as many diagnostic targets as possible by the five Metavir F stages. These targets were: fibrosis (F≥1), significant fibrosis (F≥2), severe fibrosis (F≥3), and cirrhosis (F=4). Four single-target tests were thus obtained, called FMF≥1, FMF≥2, FMF≥3 and FMF=4, respectively.

Step 2: Single-target test selection—Significant fibrosis was independently predicted by the FMF≥2 test (p<0.001) and the FMF=4 test (p<0.001) with a significant one-way interaction (p=0.001), whereas cirrhosis was independently diagnosed by the FMF≥1 test (p<0.003) and the FMF=4 test (p=0.038). Thus, three of the independent single-target tests were considered relevant for multi-target staging.

Step 3: Single-target test classifications—The test scores (range: 0 to 1) were transformed into fibrosis classifications including several classes of predicted F stages according to a previously described segmentation method (17). Three classifications for FMF≥1, FMF≥2 and FMF=4 tests were thus obtained. Here, "class" refers to fibrosis classification (staging) by non-invasive tests.

Step 4: Multi-target test classification—Briefly, each of the most accurate parts of the three retained test classifications (FIG. 2B) were progressively combined. These 3 combined parts resulted in a classification including 6 fibrosis classes (FIG. 1). This new test was called multi-target FibroMeter (MFM).

Step 5: this optional step is a multiple linear regression with the Metavir reference as dependent variable (or diagnostic target) on multi-target test classification. The score obtained can been normalized either before the regression being applied to the normalized Metavir score or after the regression normalization being applied to the regression score. If necessary, the final score is fully normalized (range 0 to 1) by bounding the extreme values (0 and 1).

Statistics

Quantitative variables were expressed as mean±standard deviation. The discriminative ability of each test was expressed as the area under the receiver operating characteristic curve (AUROC) and the overall accuracy as assessed by the rate of well-classified patients according to Metavir F. In classification calculations, test classes were used with their median value, e.g., 1.5 for F1/2. By definition, optimism bias maximizes performance in the population where test classifications are constructed: this affected FibroMeter$^{V2G}$, CirrhoMeter$^{V2G}$ and MFM in the derivation population and VCTE in the validation population #1. Data were reported according to STARD (18) and Liver FibroSTARD statements (19), and analyzed on an intention to diagnose basis. Survival curves were estimated by the Kaplan-Meier method and were compared using the log-rank test. The main statistical analyses were performed under the control of professional statisticians (SB, GH) using SPSS version 18.0 (IBM, Armonk, N.Y., USA) and SAS 9.2 (SAS Institute Inc., Cary, N.C., USA).

Results

Population Characteristics

The main characteristics of the studied populations are depicted in Table 18 below. In the prognostic population, median follow-up was 2.8 years (IQR: 1.7-3.9). During follow-up, there were 262 deaths (16.8%), of which 115 (7.4%) were liver-related.

TABLE 18

Characteristics of the populations.

| | Population | | | | |
|---|---|---|---|---|---|
| | | Validation | | | |
| | Derivation | #1 | #2 | #3 | #4 |
| Patients (n) | 1012 | 676 | 450 | 204 | 1559 |
| Male (%) | 59.6 | 60.1 | 68.9 | 77.0 | 68.9 |
| Age (years) | 45.4 ± 21.2 | 51.6 ± 11.2 | 40.5 ± 5.8 | 39.6 ± 12.1 | 54.6 ± 14.9 |

TABLE 18-continued

Characteristics of the populations.

| | Population | | | | |
|---|---|---|---|---|---|
| | | Validation | | | |
| | Derivation | #1 | #2 | #3 | #4 |
| Cause (%): | | | | | |
| Virus | 100 (HCV) | 100 (HCV) | 100 (HCV/HIV) | 100 (HBV) | 30.5 |
| Alcohol | — | — | — | — | 41.2 |
| NAFLD | — | — | — | — | 20.0 |
| Other | — | — | — | — | 8.3 |
| Metavir (%): | | | | | |
| F0 | 4.3 | 4.0 | 5.8 | 14.7 | F0/1 [a]: 15.1 |
| F1 | 43.4 | 37.6 | 24.7 | 44.1 | F1: 3.4, F1/2: 29.4 |
| F2 | 27.0 | 25.7 | 36.4 | 26.5 | F2 ± 1: 10.8 |
| F3 | 12.9 | 18.2 | 19.6 | 5.9 | F3 ± 1: 19.8, F3/4: 13.5 |
| F4 | 11.4 | 14.5 | 13.6 | 8.8 | F4: 8.0 |
| Significant fibrosis (%) | 52.3 | 58.4 | 69.6 | 41.2 | 52.1 [a] |
| Biopsy length (mm) | 21.2 ± 7.9 | 24.3 ± 9.0 | NA | 22.8 ± 7.9 | — |

NA: not available.
[a] According to FibroMeter$^{V2G}$ classification

Multi-Target Test Characteristics (Derivation Population)

Test Accuracy

Single-target test accuracy—The discriminative ability of the new single-target tests (FMF≥1, FMF≥2, FMF≥3, FMF=4) compared to previously published tests (FibroMeter$^{V2G}$, CirrhoMeter$^{V2G}$) can be summarized as follows. First, the highest AUROCs were observed with the new tests. Second, for each of the new single-target tests, the highest AUROC was observed at the diagnostic target for which the test was constructed, as expected.

Fibrosis classification accuracy—Table 19 below shows the overall fibrosis classification accuracy (as assessed by correct classification rate) of published tests (FibroMeter$^{V2G}$: 87.6%, CirrhoMeter$^{V2G}$: 87.5%) compared to the new multi-target test (MFM: 92.7%, p<0.001) in the derivation population. The accuracy was only fair in Metavir F0 for all tests. The gain in Metavir F1 for the new MFM was only moderate as the published tests already have high accuracy in this stage. In contrast, the MFM provided substantial gains in Metavir F2 and especially in F3, where it increased accuracy by 16.3% and 22.8% (p<0.001), respectively in the derivation population and validation population #1, compared to CirrhoMeter$^{V2G}$.

MFM increased accuracy in most fibrosis classes, e.g., in F4 class: MFM: 96.0%, CirrhoMeter$^{V2G}$: 88.0%, FibroMeter$^{V2G}$: 79.2% (details in Table 20 below). The comparison of classical diagnostic indices for a single diagnostic target was performed between MFM and FibroMeter$^{V2G}$ for severe fibrosis (Table 21 below); overall accuracies were 83.0% and 80.4%, respectively, p<0.010.

TABLE 19

Classification accuracy (rate of correctly-classified patients, %) of published single-target tests and the new multi-target test (MFM) as a function of Metavir fibrosis (F) stages in the derivation population and the validation populations #1, #2 and #3.

| | | Test | | | |
|---|---|---|---|---|---|
| Population/F | n | FibroMeter$^{V2G}$ | CirrhoMeter$^{V2G}$ | MFM | p [a] |
| Derivation: | | | | | |
| F0 | 44 | 56.8 | 43.2 | 54.5 | 0.212 |
| F1 | 439 | 92.3 | 89.7 | 92.5 | 0.010 |
| F2 | 273 | 89.0 | 91.2 | 96.3 | <0.001 |
| F3 | 141 | 80.1 | <u>83.0</u> | <u>99.3</u> | <0.001 |
| F4 | 115 | 87.7 | 93.0 | 91.3 | 0.174 |
| Overall | 1012 | 87.6 | 87.5 | 92.7 | <0.001 |
| Validation #1: | | | | | |
| F0 | 27 | 29.6 | 37.0 | 25.9 | 0.247 |
| F1 | 254 | 85.0 | 85.8 | 87.0 | 0.562 |
| F2 | 174 | 91.4 | 89.7 | 95.4 | 0.048 |
| F3 | 123 | 80.5 | <u>74.8</u> | <u>97.6</u> | <0.001 |
| F4 | 98 | 84.7 | 83.7 | 83.7 | 0.895 |
| Overall | 676 | 83.6 | 82.5 | 88.2 | <0.001 |

TABLE 19-continued

Classification accuracy (rate of correctly-classified patients, %) of published single-target tests and the new multi-target test (MFM) as a function of Metavir fibrosis (F) stages in the derivation population and the validation populations #1, #2 and #3.

| Population/F | n | FibroMeter$^{V2G}$ | CirrhoMeter$^{V2G}$ | MFM | p [a] |
|---|---|---|---|---|---|
| Validation #2: | | | | | |
| F0 | 26 | 15.4 | 19.2 | 23.1 | 0.549 |
| F1 | 111 | 78.4 | 73.9 | 79.3 | 0.161 |
| F2 | 164 | 84.8 | 86.6 | 92.7 | 0.004 |
| F3 | 88 | 83.0 | 85.2 | 96.6 | 0.001 |
| F4 | 61 | 80.3 | 85.2 | 82.0 | 0.417 |
| Overall | 450 | 78.2 | 79.1 | 84.7 | <0.001 |
| Validation #3: | | | | | |
| Overall [b] | 204 | 81.4 | 76.5 | 82.8 | 0.021 |

MFM: multi-target FibroMeter, n: number of patients. Bold figures indicate the highest accuracy per stage and population. Underlined accuracies show a noteworthy improvement brought about by MFM compared to the previously published CirrhoMeter$^{V2G}$ test.
[a] by paired Cochran test between all tests
[b] no result per F stage due to small sample size

TABLE 20

Classification accuracy (rate of correctly-classified patients) of published single-target tests and new multi-target test (MFM) as a function of their specific fibrosis classes in the derivation population and the validation population #1.

| | Classes | | | | | | | | | | | |
|---|---|---|---|---|---|---|---|---|---|---|---|---|
| | Derivation population | | | | | | Validation population #1 [a] | | | | | |
| | FM2G | | CM2G | | MFM | | FM2G | | CM2G | | MFM | |
| | n | DA (%) | n | DA (%) | n | DA (%) | n | DA (%) | n | DA (%) | n | DA (%) |
| F0/1 | 152 | 92.8 | 126 | 88.1 | 125 | 96.0 | 40 | 90.0 | 58 | 77.6 | 42 | 90.5 |
| F1 | 50 | 80.0 | — | — | — | — | 19 | 78.9 | — | — | — | — |
| F1/2 | 380 | 88.4 | 405 | 89.6 | 56 | 85.7 | 231 | 83.5 | 240 | 80.8 | 24 | 75.0 |
| F2 ± 1 | 126 | 91.3 | 152 | 95.4 | 531 | 95.7 | 118 | 88.1 | 117 | 91.5 | 371 | 91.9 |
| F3 ± 1 | 203 | 86.2 | 203 | 80.8 | 224 | 86.6 | 187 | 84.0 | 182 | 81.9 | 197 | 84.3 |
| F3/4 | 76 | 78.9 | 76 | 78.9 | 51 | 86.3 | 68 | 75.0 | 51 | 74.5 | 26 | 76.9 |
| F4 | 25 | 79.2 | 50 | 88.0 | 25 | 96.0 | 13 | 69.2 | 28 | 89.3 | 16 | 81.3 |
| Overall | 1012 | 87.6 | 1012 | 87.5 | 1012 | 92.7 | 676 | 83.6 | 676 | 82.5 | 676 | 88.2 |

FM2G: FibroMeter$^{V2G}$, CM2G: CirrhoMeter$^{V2G}$, MFM: multi-target FibroMeter, n: number of patients, DA: diagnostic accuracy. Bold figures indicate the highest accuracy per class and population.
[a] No results in the validation populations #2 and #3 due to small sample sizes

TABLE 21

Comparison of classical diagnostic indices between FibroMeter$^{V2G}$ and the multi-target test (MFM) for severe fibrosis (Metavir F ≥ 3).

| Test | Cut-off | Sensitivity (%) | Specificity (%) | PPV (%) | NPV (%) | Accuracy (%) | LR+ | LR− |
|---|---|---|---|---|---|---|---|---|
| FibroMeter$^{V2G}$ | 0.6275 [a] | 83.6 | 79.4 | 57.8 | 93.5 | 80.4 | 4.05 | 0.21 |
| MFM | ≥F3 ± 1 [b] | 75.0 | 85.7 | 64.0 | 91.0 | 83.0 | 5.25 | 0.29 |

PPV: positive predictive value, NPV: negative predictive value, LR: likelihood ratio, MFM: multi-target FibroMeter
[a] Maximum Youden index
[b] i.e., between classes F2 ± 1 and F3 ± 1

Cirrhosis

Cirrhosis diagnosis—Cirrhosis is an important diagnostic target. Fibrosis classification by MFM compared favorably to the other tests, especially with CirrhoMeter$^{V2G}$: the sensitivity for cirrhosis of fibrosis classes including F4 was 91.3% vs. 93.0%, respectively; the positive predictive value (PPV) for cirrhosis of the F4 class was 96.0% vs. 88.0% respectively.

Cirrhosis classification—Areas of porto-septal fibrosis (median (IQR)) were, in Metavir staging: F3: 2.7% (2.2), F4: 5.2% (6.5); and in MFM classes: F3±1: 2.3% (3.9), F3/4: 3.2% (3.9), F4: 7.3% (4.3). Thus, MFM was able to distinguish early (F3/4) and definitive (F4) cirrhosis.

Classification Precision and Refinement

Precision evaluates the capability of a fibrosis test classification to precisely reflect Metavir F stage. The mean F scores varied from 1.84±1.08 to 2.13±0.84 among test classifications (p<0.001). This showed that the classification precision had differed from one test to another. Therefore, the precision was comprehensively evaluated using four criteria: agreement, difference and linearity of test classification with Metavir F staging, and dispersion of Metavir F stages within test classes. Briefly, MFM classification had satisfactory precision criteria among the new tests (details in Table 22 below).

racy of the simplified MFM fibrosis classification was decreased to 80.4% (vs. 92.7% p<0.001 for the exhaustive MFM classification including up to three F stages per class).

Multi-Target Test Validation

Classification Accuracy in Validation Populations.

Comparison between blood tests—As expected, due to loss of optimism bias, there was an accuracy decrease (from −4.0% to −5.0%) in fibrosis classifications of FibroMeter$^{V2G}$, CirrhoMeter$^{V2G}$ and MFM in the CHC validation population #1 compared to the derivation population (Table 19). However, the overall accuracy of MFM was still significantly higher than those of FibroMeter$^{V2G}$ or CirrhoMeter$^{V2G}$ in validation populations #1 (CHC), #2 (HIV/CHC) and #3 (CHB).

Comparison with VCTE—VCTEs were available in 647 patients from population #1 and 152 patients from population #3. MFM accuracy was not significantly different from VCTE accuracy (Table 24 below). Other diagnostic indices were close between MFM and VCTE, especially for cirrhosis diagnosis despite an optimism bias in favor of VCTE. For example, in population #1, the sensitivities for cirrhosis of fibrosis classes including F4 were 86.0% and 81.7%, respectively for MFM and VCTE; the PPVs for cirrhosis of the F4 class were 80.0% and 76.7%, respectively.

TABLE 22

Fibrosis classification precision: agreement, exactness, dispersion and linearity.
Derivation population (1012 patients).

|  | Metavir F | FM ≥ 1 | FM ≥ 2 | FM2G | FMF ≥ 1/ FMF ≥ 2 | FM = 4 | CM2G | MFM | Simplified MFM |
|---|---|---|---|---|---|---|---|---|---|
| General characteristics: |  |  |  |  |  |  |  |  |  |
| Class number | 5 | 4 | 6 | 7 | 6 | 6 | 6 | 6 | 6 |
| F score (mean ± SD) | 1.84 ± 1.08 | 1.99 ± 0.70 | 1.91 ± 0.93 | 1.90 ± 0.97 | 2.07 ± 0.80 | 2.05 ± 0.86 | 2.02 ± 0.97 | 2.13 ± 0.84 | 1.82 ± 1.08 |
| p vs Metavir $^a$ | — | <0.001 | 0.014 | 0.037 | <0.001 | <0.001 | <0.001 | <0.001 | 0.267 |
| Agreement with Metavir F: |  |  |  |  |  |  |  |  |  |
| Weighted kappa | — | 0.471 | 0.600 | 0.664 | 0.529 | 0.534 | 0.641 | 0.563 | 0.703 |
| Intra-class correlation coefficient | — | 0.671 | 0.775 | 0.806 | 0.746 | 0.746 | 0.804 | 0.780 | 0.826 |
| Exactness (F difference with Metavir): |  |  |  |  |  |  |  |  |  |
| Absolute difference $^b$ | — | 0.73 ± 0.55 | 0.68 ± 0.55 | 0.65 ± 0.51 | 0.70 ± 0.55 | 0.70 ± 0.57 | 0.66 ± 0.54 | 0.68 ± 0.54 | 0.65 ± 0.52 |
| Raw difference | — | 0.14 ± 0.91 | 0.07 ± 0.87 | 0.05 ± 0.83 | 0.22 ± 0.86 | 0.20 ± 0.88 | 0.18 ± 0.84 | 0.29 ± 0.82 | 0.03 ± 0.83 |
| Dispersion (mean number of F stages/fibrosis class) | 1 | 2.83 ± 0.38 | 2.63 ± 0.53 | 2.25 ± 0.58 | 2.75 ± 0.49 | 2.70 ± 0.51 | 2.30 ± 0.56 | 2.72 ± 0.50 | 1.84 ± 0.36 |
| Linearity (correlation $^c$ with) |  |  |  |  |  |  |  |  |  |
| Metavir F | — | 0.554 | 0.640 | 0.680 | 0.623 | 0.612 | 0.676 | 0.661 | 0.703 |
| Porto-septal fibrosis area $^d$ | 0.550 | 0.238 | 0.288 | 0.326 | 0.197 | 0.329 | 0.356 | 0.226 | 0.354 |

FM2G: FibroMeter$^{V2G}$, CM2G: CirrhoMeter$^{V2G}$, FMF: single-target test, MFM: multi-target FibroMeter, n: number of patients. Best results between non-invasive tests are depicted in bold (Metavir F is excluded)

$^a$ Paired t test for F score between blood test and Metavir $^b$ Absolute difference in F score between test classification and Metavir stage (mean ± SD), i.e., deletion of minus sign in negative difference $^c$ Pearson correlation $^d$ Results obtained in validation population #1 (676 patients)

However, the MFM classification had two imprecise classes including three F stages (i.e., large dispersion). Therefore, a simplified MFM classification having a maximum of two F stages per fibrosis class was developed (FIG. 1, details in Table 23 below). The simplified MFM fibrosis classification had the best precision criteria, and particularly it was the only test with no significant difference in mean F score with Metavir staging. As expected, the overall accu- Validation of Fibrosis Classes Diagnostic population—The MFM fibrosis classification was validated by good correlations with other liver fibrosis descriptors, namely histological Metavir F, porto-septal fibrosis area, and liver stiffness measured by VCTE. More importantly, these liver fibrosis descriptors were significantly different between adjacent fibrosis classes of the MFM test.

TABLE 23

Simplified classification of multi-target test (MFM). The cut-offs of this classification and those of the exhaustive classification are different; thus, two new classes of the simplified classification (F1 and F2/3) lie across two classes of the exhaustive classification. x denotes the predominant F stages per fibrosis class. Fine dashed lines delineate the employed parts of the single-target tests (left column); coarse dashed lines delineate fibrosis classes of the multi-target test (right columns). Derivation population (1012 patients).

| Single-target test | | Metavir F stage | | | | | Multi-target test | |
|---|---|---|---|---|---|---|---|---|
| Test name | Cut-off | 0 | 1 | 2 | 3 | 4 | Class | Accuracy (%) |
| FMF ≥ 1 | 0 to ≤0.92 | x | x | — | — | — | F0/1 | 89.7 |
|  | >0.92 to MFM [a] | — | x | — | — | — | F1 | 73.4 |
| FMF ≥ 2 | MFM [a] to ≤0.28 |  |  |  |  |  |  |  |
|  | >0.28 to ≤0.758 | — | x | x | — | — | F1/2 | 86.6 |
|  | >0.758 to MFM [a] | — | — | x | x | — | F2/3 | 70.7 |
| FMF = 4 | MFM [a] to ≤0.135 |  |  |  |  |  |  |  |
|  | >0.135 to ≤0.71 | — | — | — | x | x | F3/4 | 65.8 |
|  | >0.71 to 1 | — | — | — | — | x | F4 | 86.0 |
| Accuracy (%) | — | 72.7 | 90.4 | 71.4 | 70.9 | 78.3 | — | 80.4[b] | x denotes predominant Metavir F stage
[a] MFM cut-offs (see FIG. 2B in main text).
[b] Overall accuracy in the whole population

TABLE 24

Overall accuracy (OA in %) of blood tests and VCTE (Fibroscan) classifications in two validation populations.

| Population | MFM OA | FibroMeter$^{V2G}$ OA | FibroMeter$^{V2G}$ p[a] | CirrhoMeter$^{V2G}$ OA | CirrhoMeter$^{V2G}$ p[a] | VCTE OA | VCTE p[a] | p[b] |
|---|---|---|---|---|---|---|---|---|
| #1 | 88.6 | 84.1 | <0.001 | 83.0 | <0.001 | 87.8 | 0.691 | 0.009 |
| #3 | 80.9 | 80.3 | 1 | 74.3 | 0.031 | 80.9 | 1 | 0.121 |

MFM: multi-target FibroMeter, VCTE: vibration-controlled transient elastography
Bold figures indicate significant differences.
[a] Comparison vs. MFM by paired McNemar test
[b] Comparison of VCTE vs. CirrhoMeter$^{V2G}$ by paired McNemar test Prognostic Population Population Characteristics All subjects over 18 years of age who were received for consultation or hospitalized for a chronic liver disease in the Department of Hepatology at the University Hospital of Angers from January 2005 to December 2009 were invited to join a study cohort, whatever the severity or etiology of their disease (viral hepatitis, alcoholic liver disease, non-alcoholic fatty liver disease (NAFLD), other causes). The resulting 1559 patients were then followed until death, liver transplantation or Jan. 1, 2011. The study was approved by an Institutional Review Board (AC-2012-1507) and informed consent was obtained from all patients.

Results

Figure 3C:
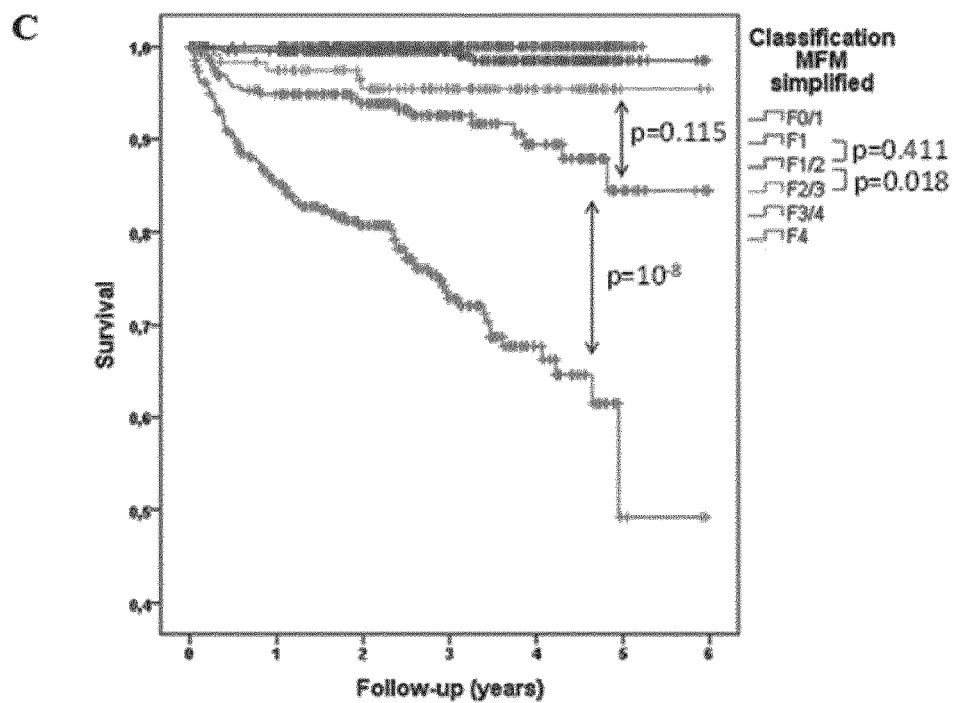
FIG. 3 is a combination of graphs showing Kaplan-Meier plots of liver-related death rates in miscellaneous causes of chronic liver disease by test classifications (validation population #4: 1559 patients): (A) FibroMeter$^{V2G}$, (B) exhaustive multi-target FibroMeter (MFMc), (C) simplified multi-target FibroMeter (MFMc). Vertical dashes indicate censored patients.

The MFMc fibrosis classification was validated for prognostic ability of liver-related death (p<0.001 by log rank test). FIG. 3 shows that the survival curves were significantly different between the following four classes of FibroMeter$^{V2G}$ and MFMc: F2±1, F3±1, F3/4 and F4. The difference in survival curves between the F3/4 and F4 classes was more pronounced in the MFMc classification (p=3.10-4) than in the FibroMeter$^{V2G}$ classification (p=3.10-3). Finally, the simplified MFMc classification was validated by a good prognostic value for liver-related death (p<0.001 by log rank test). Moreover, the discrimination between the F3/4 and F4 classes was better in the simplified MFMc classification (p=10-8) (FIG. 3C) compared to the exhaustive MFMc classification (p=3.10-4) (FIG. 3B).

The MFMc classification offered good prognostic discrimination, especially between four fibrosis classes: F2±1, F3±1, F3/4 and F4. The prognostic discrimination between the F3/4 and F4 classes was improved compared to FibroMeter$^{V2G}$ (FIG. 3). It was recently shown that the combination of FibroMeter$^{V2G}$ and CirrhoMeter$^{V2G}$ was synergistic for prognosis in another cohort (20); in that study, like here, there was a significant interaction between tests targeted for significant fibrosis or cirrhosis. A simplified classification was developed, with a maximum of two F stages per class, which improved prognostication and precision.

These results will raise the question as to whether a simplified or exhaustive classification should be used. An exhaustive classification (up to three F per class) has the apparent advantage of better accuracy compared to a simplified classification (up to two F per class). However, the latter offers better precision and prognostication. Thus, a simplified classification seems sufficient for clinical practice. The lack of interest of an exhaustive classification can be attributed to the sources of misclassification by histological staging (sample size and observer reading). This is reinforced by the better prognostication by non-invasive tests than by histological staging (21). Finally, prognostication is significantly altered only by F2±1 or even F2/3 class, and thus the minimal classification can be described into four classes: F0/1 (non-significant fibrosis), F2/3 (significant fibrosis), F3/4 (early cirrhosis) and F4 (definitive cirrhosis).

REFERENCES

1. Oberti F, Valsesia E, Pilette C, et al. Noninvasive diagnosis of hepatic fibrosis or cirrhosis. Gastroenterology 1997; 113:1609-16.
2. Chou R, Wasson N. Blood tests to diagnose fibrosis or cirrhosis in patients with chronic hepatitis C virus infection: a systematic review. Annals of internal medicine 2013; 158:807-20.
3. Boursier J, Bertrais S, Oberti F, et al. Comparison of accuracy of fibrosis degree classifications by liver biopsy and non-invasive tests in chronic hepatitis C. BMC Gastroenterol 2011; 11:132.
4. Cales P, Boursier J, Oberti F, et al. Cirrhosis Diagnosis and Liver Fibrosis Staging: Transient Elastometry Versus Cirrhosis Blood Test. Journal of clinical gastroenterology 2014.
5. Cales P, de Ledinghen V, Halfon P, et al. Evaluating the accuracy and increasing the reliable diagnosis rate of blood tests for liver fibrosis in chronic hepatitis C. Liver Int 2008; 28:1352-62.
6. Boursier J, de Ledinghen V, Zarski J P, et al. Comparison of eight diagnostic algorithms for liver fibrosis in hepatitis C: new algorithms are more precise and entirely noninvasive. Hepatology 2012; 55:58-67.
7. Boursier J, de Ledinghen V, Zarski J P, et al. A new combination of blood test and fibroscan for accurate non-invasive diagnosis of liver fibrosis stages in chronic hepatitis C. Am J Gastroenterol 2011; 106:1255-63.
8. Calès P, Halfon P, Batisse D, et al. Comparison of liver fibrosis blood tests developed for HCV with new specific tests in HIV/HCV co-infection J Hepatol 2010; 52:238-44.
9. Leroy V, Sturm N, Faure P, et al. Prospective evaluation of FibroTest®, FibroMeter®, and HepaScore® for staging liver fibrosis in chronic hepatitis B: comparison with hepatitis C. J Hepatol 2014; 61:28-34.
10. Intraobserver and interobserver variations in liver biopsy interpretation in patients with chronic hepatitis C. The French METAVIR Cooperative Study Group. Hepatology 1994; 20:15-20.
11. Zarski J P, Sturm N, Guechot J, et al. Comparison of nine blood tests and transient elastography for liver fibrosis in chronic hepatitis C: The ANRS HCEP-23 study. J Hepatol 2012; 56:55-62.
12. Sandrini J, Boursier J, Chaigneau J, et al. Quantification of portal-bridging fibrosis area more accurately reflects fibrosis stage and liver stiffness than whole fibrosis or perisinusoidal fibrosis areas in chronic hepatitis C. Mod Pathol 2014; 27:1035-45.
13. Cales P, Oberti F, Michalak S, et al. A novel panel of blood markers to assess the degree of liver fibrosis. Hepatology 2005; 42:1373-81.
14. Cales P, Boursier J, Bertrais S, et al. Optimization and robustness of blood tests for liver fibrosis and cirrhosis. Clin Biochem 2010; 43:1315-22.
15. Cales P, Boursier J, Oberti F, et al. FibroMeters: a family of blood tests for liver fibrosis. Gastroenterol Clin Biol 2008; 32:40-51.
16. Castera L, Forns X, Alberti A. Non-invasive evaluation of liver fibrosis using transient elastography. J Hepatol 2008; 48:835-47.
17. Leroy V, Halfon P, Bacq Y, et al. Diagnostic accuracy, reproducibility and robustness of fibrosis blood tests in chronic hepatitis C: a meta-analysis with individual data. Clin Biochem 2008; 41:1368-76.
18. Bossuyt P M, Reitsma J B, Bruns D E, et al. The STARD statement for reporting studies of diagnostic accuracy: explanation and elaboration. Clin Chem 2003; 49:7-18.
19. Boursier J, de Ledinghen V, Poynard T, et al. An extension of STARD statements for reporting diagnostic accuracy studies on liver fibrosis tests: The Liver-Fibro-STARD standards. J Hepatol 2014.
20. Boursier J, Brochard C, Bertrais S, et al. Combination of blood tests for significant fibrosis and cirrhosis improves the assessment of liver-prognosis in chronic hepatitis C. Alimentary pharmacology & therapeutics 2014; 40:178-88.
21. Naveau S, Gaude G, Asnacios A, et al. Diagnostic and prognostic values of noninvasive biomarkers of fibrosis in patients with alcoholic liver disease. Hepatology 2009; 49:97-105.
22. Cales P, Boursier J, Ducancelle A, et al. Improved fibrosis staging by elastometry and blood test in chronic hepatitis C. Liver international 2014; 34:907-17.
23. Boursier J, Zarski J P, de Ledinghen V, et al. Determination of reliability criteria for liver stiffness evaluation by transient elastography. Hepatology 2013; 57:1182-91.

Example 3: Construction of the Multi-Targeted Classification in the MFMc

The objective was to select and combine the most accurate parts of the three retained test classifications (FIG. 1). The principles were as follows. The rate of correctly classified patients (or accuracy) was compared between two adjacent retained single-target tests. The limits of the fibrosis classes retained were determined by those of the corresponding test score. The aim was to find the best cut-off maximizing the global accuracy rate including the two tests. Note that the three tests were used expressed either in score (for cut-off determination) or classification (for accuracy determination). Secondarily, two test classifications were generated: FMF≥1/FMF≥2 classification (intermediate classification) and FMF≥1/FMF≥2/FMF=4 (final classification).

Figure 2A:
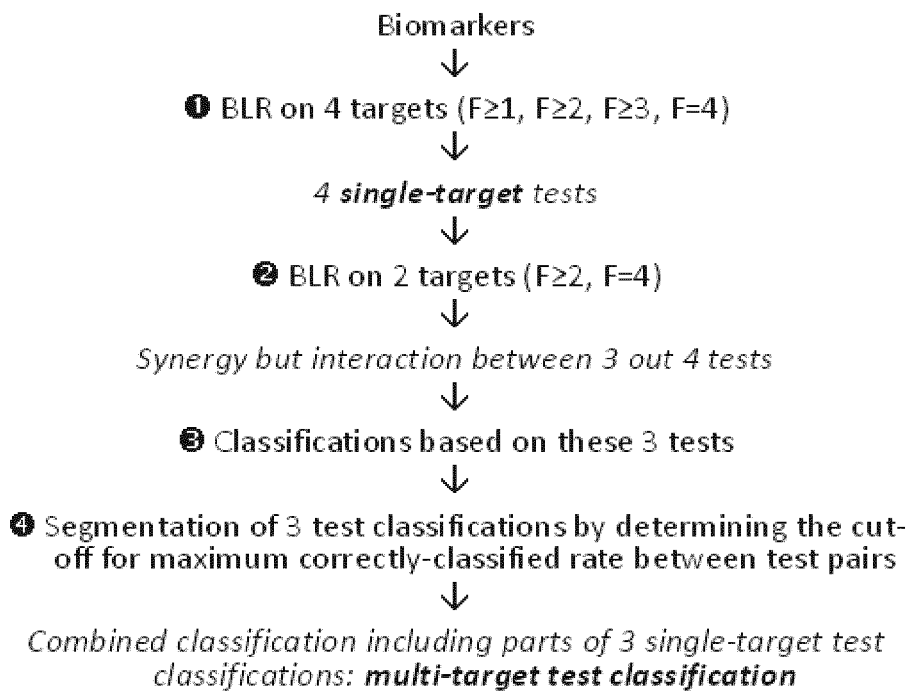
FIG. 2 is a combination of diagrams illustrating the construction of the Multi-FibroMeter (MFMc). Panel A shows the four different statistical steps; BLR: binary logistic regression: step 1 describes an example with 4 single-targeted tests called FMF≥1, FMF≥2, FMF≥3 and FMF=4. Panel B shows details on the construction of step 4 of panel A, which provided the final combined classification of the multi-target test by incorporating parts of single-target test classifications. It included 4 statistical sub-steps as indicated: 1) accuracy comparison between parts of FMF≥1 and FMF≥2 classifications; 2) combination of parts of FMF≥1 and FMF≥2 classifications; 3) accuracy comparison between parts of FMF≥1 plus FMF≥2 classification and of FMF=4 classification; 4) combination of parts of FMF≥1 plus FMF≥2 classification and of FMF=4 classification (i.e., multi-target test classification). Figures indicate score cut-offs of single-target tests.

Practically, the analysis was first started with the early F stages (FIG. 2A). Thus, the accuracy was the sum of correctly classified patients with FMF≥1 classification below the cut-off of FMF≥1 score and by the FMF≥2 classification beyond this cut-off; this calculation was repeated, from low to high score values, to find the best cut-off among increasing values of FMF≥1 score maximizing the global accuracy (Table 25). "Global accuracy" means the sum of two accuracies.

The same calculation was then repeated to determine the best cut-off of FMF≥2 score (Table 2, FIG. 2A). Two combined classifications were thus obtained with cut-offs determined either by the first or the second FMF test (Tables 25 and 26). The choice between the two combined classifications was determined mainly by the maximum global accuracy obtained and then by the maximum population size remaining available with the second test (FMF≥2) for the next calculation including FMF=4 test. We thus obtained a combined FMF≥1/FMF≥2 classification with a cut-off determined by FMF≥2 score at 0.27 (Table 26).

Figure 2B:
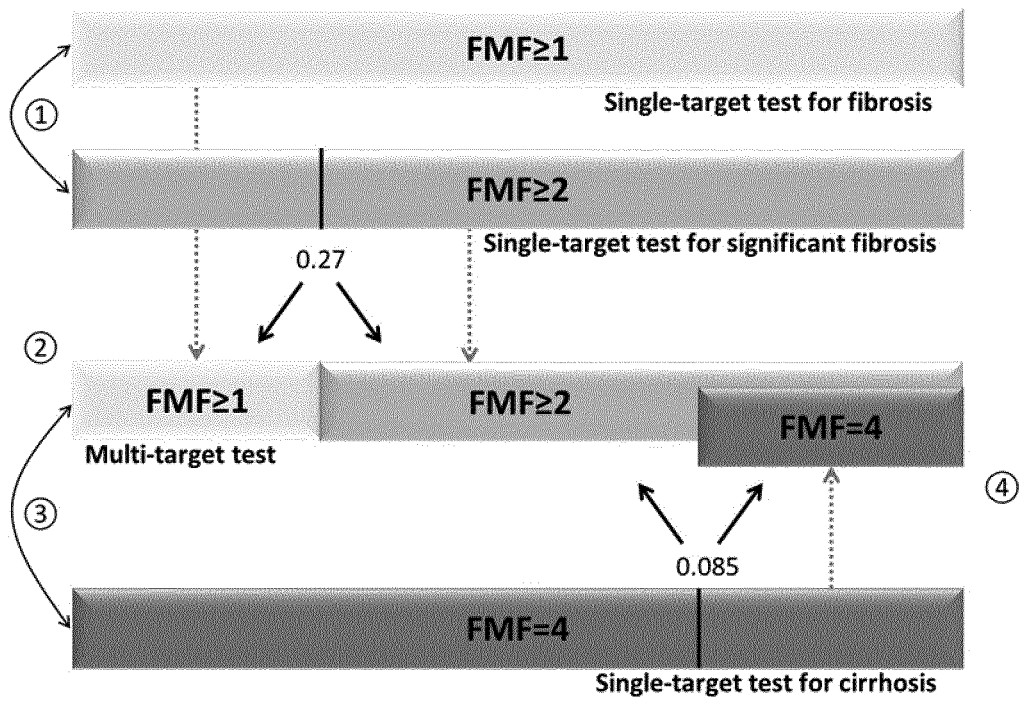

The same calculations were then repeated to compare the FMF≥1/FMF≥2 classification to the FMF=4 classification (Tables 27 and 28, FIG. 2B). The best combined FMF≥1/FMF≥2/FMF=4 classification was finally determined with the incorporation of the FMF4 score cut-off at 0.085 by using the following classifications: FMF≥1/FMF≥2 below this cut-off and FMF=4 beyond this cut-off (Table 28). This last choice was determined by the best discrimination of F4 stage.

The relationship between the 3 scores included and their 3 respective parts retained is shown in FIG. 3. These 3 combined parts resulted in a MFMc classification including 6 fibrosis classes with a simplified version including less fibrosis stages per fibrosis class (FIG. 4). FIG. 5 shows that some fibrosis classes of the double-target FMF≥1/FMF≥2 test could be provided by two different classifications of a single-target test. In other words, the final 6-class classification was not a simple juxtaposition of fibrosis classes belonging to the same single-target classification.

TABLE 25

Comparison of correctly classified patients (%) between FMF ≥ 1 and FMF ≥ 2 scores as a function of growing FMF ≥ 1 cut-off.

| FMF ≥ 1 Cut-off | Correctly classified patients (%) by | | | | | | |
|---|---|---|---|---|---|---|---|
| | FMF ≥ 1 | | | FMF ≥ 2 | | | Both |
| | < [a] | ≥ [b] | p | < [a] | ≥ [b] | p | < + ≥ [c] |
| 0.7 | 100 | 91.5 | <0.001 | 100 | 90.5 | <0.001 | 90.6% |
| 0.8 | 100 | 91.2 | <0.001 | 100 | 90.2 | <0.001 | 90.6% |
| 0.85 | 98.7 | 91 | <0.001 | 98.7 | 89.9 | <0.001 | 90.6% |
| 0.9 | 92.9 | 91.4 | 0.526 | 91 | 90.5 | 0.8969 | 90.9% |
| 0.95 | 93.5 | 90.9 | 0.188 | 89.9 | 90.9 | 0.613 | 91.6% |
| 0.96 | 93.9 | 90.6 | 0.054 | 90.7 | 90.6 | 0.929 | 91.6% |
| 0.97 | 94.7 | 89.7 | 0.006 | 91.5 | 90.1 | 0.438 | 91.8% |
| 0.98 | 94.3 | 89.6 | 0.007 | 91.3 | 90.1 | 0.511 | 91.9% |
| 0.99 | 94.1 | 88.9 | 0.003 | 91.2 | 90 | 0.492 | 92.1% [d] |
| 0.995 | 93.9 | 88.1 | 0.001 | 91.6 | 89.1 | 0.168 | 92.0% |
| 0.997 | 93.8 | 87.6 | 0.001 | 91.5 | 89 | 0.208 | 92.1% |
| 0.999 | 92 | 90.3 | 0.391 | 91 | 89.5 | 0.491 | 91.4% |
| 0.9995 | 91.7 | 91 | 0.751 | 90.9 | 89.6 | 0.565 | 91.3% |
| 0.9998 | 91.4 | 92.6 | 0.53 | 90.8 | 89.4 | 0.605 | 91.1% |

[a] Correctly classified patients (%) below the FMF ≥ 1 cut-off.
[b] Correctly classified patients (%) beyond the FMF ≥ 1 cut-off.
[c] Sum of correctly classified patients (%) below the FMF ≥ 1 cut-off by FMF ≥ 1 plus correctly classified patients (%) by FMF ≥ 2 beyond the FMF ≥ 1 cut-off.
[d] Maximum rate deteimining the cut-off choice.

TABLE 26

Comparison of correctly classified patients (%) between FMF ≥ 1 and FMF ≥ 2 scores as a function of growing FMF ≥ 2 cut-off.

| FMF ≥ 2 Cut-off | Correctly classified patients (%) by | | | | | | |
|---|---|---|---|---|---|---|---|
| | FMF ≥ 1 | | | FMF ≥ 2 | | | Both |
| | < [a] | ≥ [b] | p | < [a] | ≥ [b] | p | <+≥ [c] |
| 0.1 | 100 | 91.2 | <0.001 | 100 | 90.2 | <0.001 | 90.6% |
| 0.2 | 93.9 | 91 | 0.142 | 90.9 | 90.5 | 0.873 | 91.2% |
| 0.21 | 94.4 | 90.9 | 0.06 | 90.7 | 90.6 | 0.981 | 91.4% |
| 0.22 | 94.3 | 90.8 | 0.058 | 89.6 | 91.2 | 0.277 | 91.9% |
| 0.23 | 93.5 | 91 | 0.177 | 87.9 | 91.5 | 0.116 | 92.0% |
| 0.25 | 93.8 | 90.8 | 0.096 | 88.3 | 91.5 | 0.154 | 92.1% |
| 0.26 | 93.6 | 90.8 | 0.128 | 88.3 | 91.5 | 0.136 | 92.1% |
| 0.27 | 93.9 | 90.7 | 0.074 | 88.7 | 91.4 | 0.215 | 92.1% [d] |
| 0.28 | 93.7 | 90.8 | 0.091 | 88.7 | 91.4 | 0.184 | 92.1% |
| 0.29 | 93.3 | 90.8 | 0.165 | 88.5 | 91.5 | 0.149 | 92.1% |
| 0.3 | 93.6 | 90.7 | 0.101 | 89 | 91.4 | 0.231 | 92.1% |
| 0.35 | 94 | 90.1 | 0.021 | 90.4 | 90.7 | 0.85 | 92.0% |
| 0.4 | 94.2 | 89.7 | 0.009 | 90.9 | 90.4 | 0.797 | 92.0% |
| 0.5 | 94.5 | 88.7 | 0.001 | 91.7 | 89.5 | 0.221 | 92.0% |
| 0.6 | 95.1 | 86.7 | <0.001 | 92.7 | 87.6 | 0.009 | 92.0% |
| 0.7 | 94.4 | 86.1 | <0.001 | 92.5 | 87 | 0.008 | 91.9% |
| 0.8 | 93.2 | 87.3 | 0.008 | 91.7 | 87.6 | 0.068 | 91.7% |
| 0.9 | 92 | 89.5 | 0.313 | 90.8 | 89.5 | 0.592 | 91.6% |

[a] Correctly classified patients (%) below the FMF ≥ 2 cut-off.
[b] Correctly classified patients (%) beyond the FMF ≥ 2 cut-off.
[c] Sum of correctly classified patients (%) below the FMF ≥ 2cut-off by FMF ≥ 1 plus correctly classified patients (%) by FMF ≥ 2 beyond the FMF ≥ 2 cut-off.
[d] Maximum rate determining the cut-off choice.

TABLE 27

Comparison of correctly classified patients (%) between FMF ≥ 1/FMF ≥ 2 classification and FMF = 4 score as a function of growing FMF ≥ 2 cut-off.

| | Correctly classified patients (%) by | | | | | | |
|---|---|---|---|---|---|---|---|
| FMF ≥ 2 Cut-off | FMF ≥ 1/FMF ≥ 2 | | | FMF = 4 | | | Both |
| | < [a] | ≥ [b] | p | < [a] | ≥ [b] | p | < + ≥ [c] |
| 0.2 | 93.9 | 91.6 | | 92.9 | 90.8 | | 91.4% |
| 0.3 | 93.6 | 91.4 | 0.213 | 91.4 | 91.1 | 0.873 | 91.9% |
| 0.33 | 94.1 | 91 | 0.065 | 91.6 | 91 | 0.721 | 92.1% |
| 0.35 | 94.3 | 90.7 | 0.033 | 91.9 | 90.7 | 0.508 | 92.1% |
| 0.37 | 94.1 | 90.79 | 0.049 | 91.8 | 90.79 | 0.563 | 92.1% |
| 0.38 | 94.2 | 90.65 | 0.033 | 92 | 90.65 | 0.448 | 92.1% |
| 0.39 | 94.3 | 90.54 | 0.024 | 92.1 | 90.54 | 0.369 | 92.1% |
| 0.4 | 94.4 | 90.4 | 0.016 | 92.1 | 90.6 | 0.408 | 92.2% |
| 0.5 | 94.7 | 89.5 | 0.002 | 92.5 | 89.9 | 0.139 | 92.3% |
| 0.55 | 95 | 88.5 | <0.001 | 92.7 | 89.4 | 0.071 | 92.5% |
| 0.6 | 95.3 | 87.6 | <0.001 | 92.7 | 89.1 | 0.043 | 92.7% |
| 0.63 | 95.3 | 87.2 | <0.001 | 92.7 | 88.9 | 0.049 | 92.8% |
| 0.64 | 95.2 | 87.2 | <0.001 | 92.6 | 89 | 0.059 | 92.8% |
| 0.65 | 95.1 | 87.1 | <0.001 | 92.4 | 89.2 | 0.091 | 92.9% |
| 0.66 | 95.1 | 86.9 | <0.001 | 92.5 | 89 | 0.072 | 92.9% |
| 0.67 | 95.2 | 86.6 | <0.001 | 92.4 | 89.1 | 0.088 | 93.0% [d] |
| 0.68 | 95.1 | 86.8 | <0.001 | 92.4 | 89 | 0.078 | 92.9% |
| 0.69 | 94.7 | 87.3 | <0.001 | 92.4 | 89 | 0.079 | 92.7% |
| 0.7 | 94.7 | 87 | <0.001 | 92.5 | 88.7 | 0.045 | 92.6% |
| 0.8 | 93.8 | 87.6 | 0.005 | 92.4 | 88 | 0.045 | 92.2% |
| 0.9 | 92.6 | 89.5 | 0.212 | 91.6 | 89.5 | 0.413 | 92.1% |
| 0.95 | 92.5 | 88.7 | 0.237 | 91.1 | 91.5 | 0.906 | 92.4% |
| 0.97 | 92.5 | 86.3 | 0.136 | 91.4 | 89 | 0.54 | 92.2% |

[a] Correctly classified patient (%) below the FMF ≥ 2 cut-off.
[b] Correctly classified patients (%) beyond the FMF ≥ 2 cut-off.
[c] Sum of correctly classified patients (%) below the FMF ≥ 2 cut-off by FMF ≥ 1/FMF ≥ 2 plus correctly classified patients (%) by FMF = 4 beyond the FMF ≥ 2 cut-off.
[d] Maximum rate determining the cut-off choice.

TABLE 28

Comparison of correctly classified patients (%) between FMF ≥ 1/FMF ≥ 2 classification and FMF = 4 score as a function of growing FMF = 4 cut-off

| | Correctly classified patients (%) by | | | | | | |
|---|---|---|---|---|---|---|---|
| FMF = 4 Cut-off | FMF ≥ 1/FMF ≥ 2 | | | FMF = 4 | | | Both |
| | < [a] | ≥ [b] | p | < [a] | ≥ [b] | p | < + ≥ [c] |
| 0.005 | 93.7 | 91.8 | 0.373 | 88.7 | 91.7 | 0.267 | 92.0% |
| 0.006 | 94.8 | 91.5 | 0.182 | 90.2 | 91.5 | 0.583 | 92.1% |
| 0.007 | 94.1 | 91.6 | 0.073 | 89.5 | 91.7 | 0.343 | 92.2% |
| 0.01 | 93.3 | 91.6 | 0.35 | 89.8 | 91.8 | 0.342 | 92.2% |
| 0.02 | 94.3 | 90.3 | 0.016 | 91.2 | 91.2 | 0.982 | 92.6% |
| 0.03 | 94.9 | 88.9 | 0.001 | 92.5 | 89.7 | 0.127 | 92.5% |
| 0.04 | 94.6 | 88.3 | 0.001 | 92.8 | 88.8 | 0.037 | 92.3% |
| 0.05 | 94.7 | 87.1 | 0.001 | 93.1 | 87.6 | 0.008 | 92.3% |
| 0.08 | 94.8 | 85.2 | 0.001 | 92.9 | 87 | 0.008 | 92.6% |
| 0.085 | 94.9 | 84.7 | <0.001 | 92.8 | 86.9 | 0.009 | 92.7% [d] |
| 0.09 | 94.8 | 84.6 | <0.001 | 92.8 | 86.8 | 0.009 | 92.7% |
| 0.095 | 94.7 | 84.4 | <0.001 | 92.7 | 86.8 | 0.011 | 92.7% |
| 0.1 | 94.6 | 84.5 | <0.001 | 92.8 | 86.5 | 0.008 | 92.6% |
| 0.15 | 93.3 | 87 | 0.015 | 92 | 88 | 0.122 | 92.3% |
| 0.2 | 92.8 | 88.5 | 0.115 | 91.4 | 90.4 | 0.704 | 92.4% |

[a] Correctly classified patient (%) below the FMF = 4 cut-off.
[b] Correctly classified patients (%) beyond the FMF = 4 cut-off.
[c] Sum of correctly classified patients (%) below the FMF = 4 cut-off by FMF ≥ 1/FMF ≥ 2 plus correctly classified patients (%) by FMF = 4 beyond the FMF = 4 cut-off.
[d] Maximum rate determining the cut-off choice.

The invention claimed is:

1. A method for treating an individual suffering from a liver fibrosis, comprising:
    determining in the individual the presence and severity of a liver fibrosis by:
    1) performing at least 3 binary logistic regressions, or at least 3 other statistical analyses selected from linear discriminant analyses and multivariate analyses, on at least one variable, wherein the binary logistic regressions, or other statistical analyses, are performed on the same variable(s) but are each directed to a different single diagnostic target, thereby obtaining at least 3 scores;
    2) combining the at least 3 scores obtained in step 1) in a multiple linear regression to obtain a new multi-targeted score, thereby determining the presence and severity of a liver fibrosis in the individual; and implementing an adapted patient care depending on the severity of the liver fibrosis, comprising:
monitoring the individual by assessing the liver fibrosis severity at regular intervals,
administering without delay at least one therapeutic agent to the individual, wherein said at least one therapeutic agent is an antifibrotic agent selected from the group consisting of simtuzumab, GR-MD-02, stem cell transplantation, *Phyllanthus urinaria*, Fuzheng Huayu, S-adenosyl-L-methionine, S-nitrosol-N-acetylcystein, silymarin, phosphatidylcholine, N-acetylcysteine, resveratrol, vitamin E, losartan, telmisartan, naltrexone, RF260330, sorafenib, imatinib mesylate, nilotinib, INT747, FG-3019, oltipraz, pirfenidone, halofuginone, polaorezin, gliotoxin, sulfasalazine, rimonabant, and combinations thereof, or
wherein said at least one therapeutic agent is for treating the underlying cause responsible for the liver fibrosis, and/or
starting a complication screening program for applying early prophylactic or curative treatment.

2. The method according to claim 1, wherein determining in the individual the presence and severity of a liver fibrosis further comprises a third step of sorting the multi-targeted score obtained in step 2) in a classification of liver fibrosis stages, thereby determining to which liver fibrosis stage the individual belongs based on his/her multi-targeted score.

3. The method according to claim 1, wherein determining in the individual the presence and severity of a liver fibrosis is carried out by:
1) performing at least 3 binary logistic regressions, or at least 3 other statistical analyses selected from linear discriminant analyses and multivariate analyses, on at least one variable, wherein the binary logistic regressions, or other statistical analyses, are performed on the same variable(s) but are each directed to a different single diagnostic target, thereby obtaining at least 3 scores;
1a) performing at least another binary logistic regression including the at least 3 scores obtained at step 1), wherein the diagnostic target of said binary logistic regression is a clinically relevant binary target, thereby identifying the significant single-targeted scores among those obtained by the binary logistic regressions, or other statistical analyses, of step 1), said significant single-targeted scores being independently associated with said clinically relevant binary diagnostic target;
1b) deriving a classification of liver fibrosis stages for each of the single-targeted binary logistic regressions, or other statistical analyses, found significant in step 1a);
1c) combining the classifications of step 1b) into a multi-targeted classification of liver fibrosis stages; and
2) combining the significant scores identified in step 1a) in a multiple linear regression to obtain a single multi-targeted score, thereby determining the presence and severity of a liver fibrosis in the individual.

4. The method according to claim 1, wherein step 1) comprises performing at least 3 binary logistic regressions.

5. The method according to claim 1, wherein step 1) comprises performing 4 binary logistic regressions, each targeting a different Metavir fibrosis stage corresponding to F1, F2, F3, and F4 stages.

6. The method according to claim 1, wherein step 1) comprises performing 7 binary logistic regressions, each with a different fibrosis target corresponding to Metavir fibrosis stages F≥1 (F≥1 vs. F0), F≥2 (F≥2 vs. F≤1), F≥3 (F≥3 vs. F≤2), F4 (F4 vs. F≤3), F1 vs. F0+F2+F3+F4, F2 vs. F0+F1+F3+F4, and F3 vs. F0+F1+F2+F4.

7. The method according to claim 1, wherein step 1) comprises performing 10 binary logistic regressions, each with a different fibrosis target corresponding to Metavir fibrosis stages F≥1 vs. F=0, F≥2 vs. F≤1, F≥3 vs. F≤2, F=4 vs. F≤3, F1 vs. F0+F2+F3+F4, F2 vs. F0+F1+F3+F4, F3 vs. F0+F1+F2+F4, F1+F2 vs. F0+F3+F4, F2+F3 vs. F0+F1+F4, and F1+F2+F3 vs. F0+F4.

8. The method according to claim 1, wherein the binary logistic regressions of step 1) are performed on at least one variable selected from biomarkers, clinical markers, qualitative markers, data obtained by a physical method of diagnosis, scores of fibrosis tests, descriptors of at least one image of the liver tissue of the individual previously obtained by an imaging method, and mathematical combinations thereof.

9. The method according to claim 8, wherein the binary logistic regressions of step 1) are performed on at least two descriptors of at least one image of the liver tissue of the individual previously obtained by an imaging method, said descriptors being selected from the group consisting of linearity percentage of the edges, mean of percentage of fibrosis around areas, area of stellar fibrosis among the total surface of the liver biopsy specimen, number of bridges, bridges thickness, mean area of porto-septal regions, bridges perimeter, ratio of bridges among the porto-septal areas, area of fibrosis in the bridges, fractal dimension of peri-sinusoidal fibrosis, perimeter of the organ, tissue or fragment thereof, fractal dimension of porto-septal fibrosis, ratio of peri-sinusoidal fibrosis among the whole fibrosis, length of the organ, tissue or fragment thereof, anfractuosity descriptors including native perimeter, smoothed perimeter and ratio between both perimeters, fractal dimension of fibrosis, interquartile range of total density, Arantius furrow thickness, mean native liver perimeter, mean total spleen perimeter, ratio spleen surface to liver surface, and mathematic combinations thereof.

10. The method according to claim 8, wherein the binary logistic regressions of step 1) are performed on at least one data obtained by a physical method of diagnosis, said physical method of diagnosis being an elastography method selected from Vibration Controlled Transient Elastography (VCTE) also known as Fibroscan, Acoustic Radiation Force Impulse (ARFI) imaging, supersonic shear imaging (SSI) elastometry, and NMR/MRI (nuclear magnetic resonance/magnetic resonance imaging) elastography.

11. The method according to claim 8, wherein the binary logistic regressions of step 1) are performed on at least one data obtained by a physical method of diagnosis, said physical method of diagnosis being a radiography method selected from X-ray, ultrasonography, computerized scanner, magnetic resonance imaging (MRI), functional magnetic resonance imaging, tomography, computed axial tomography, proton emission tomography (PET), single photon emission computed tomography, and tomodensitometry.

12. The method according to claim 8, wherein the binary logistic regressions of step 1) are performed on at least one score of fibrosis test obtained with a fibrosis test selected from APRI, FIB4, Fibrotest, ELF score, FibroMeter, Fibrospect, Hepascore, Zeng score, and NAFLD fibrosis score, wherein said fibrosis test comprises the combination in a simple mathematical function or a binary logistic regression of markers selected from biological markers and/or clinical markers.

13. The method according to claim 1, wherein the binary logistic regressions of step 1) correspond to a fibrosis test selected from the FibroMeter family of fibrosis tests and combinations thereof with Vibration Controlled Transient Elastography (VCTE) also known as Fibroscan.

14. The method according to claim 1, wherein the individual suffers from a liver condition selected from the group consisting of a liver impairment, a chronic liver disease, a hepatitis viral infection especially an infection caused by hepatitis B, C or D virus, a hepatotoxicity, a liver cancer, a steatosis, a non-alcoholic fatty liver disease (NAFLD), a non-alcoholic steato-hepatitis (NASH), an autoimmune disease, a metabolic liver disease, and a disease with secondary involvement of the liver.

* * * * *